US008263558B2

(12) United States Patent
Holzman et al.

(10) Patent No.: US 8,263,558 B2
(45) Date of Patent: Sep. 11, 2012

(54) METHODS OF PREPARATION OF RECOMBINANT FORMS OF HUMAN BETA-AMYLOID PROTEIN AND USES OF THESE PROTEINS

(75) Inventors: Thomas F. Holzman, Libertyville, IL (US); John E. Harlan, Lake Zurich, IL (US); Rohinton P. Edalji, Wadsworth, IL (US); Edward T. Olejniczak, Grayslake, IL (US); Ana Pereda-Lopez, Mundelein, IL (US); Boris Labkovsky, Wales, MA (US); Liping Yu, Libertyville, IL (US); Heinz Hillen, Hassloch (DE); Stefan Barghorn, Mannheim (DE); Ulrich M. Ebert, Mannheim (DE)

(73) Assignees: Abbott Laboratories, Abbott Park, IL (US); Abbott GmbH & Co. KG, Wiesbaden-Delkenheim (DE)

( * ) Notice: Subject to any disclaimer, the term of this patent is extended or adjusted under 35 U.S.C. 154(b) by 377 days.

(21) Appl. No.: 11/574,844

(22) PCT Filed: Nov. 30, 2006

(86) PCT No.: PCT/US2006/046043
§ 371 (c)(1),
(2), (4) Date: Sep. 30, 2008

(87) PCT Pub. No.: WO2007/064917
PCT Pub. Date: Jun. 7, 2007

(65) Prior Publication Data
US 2009/0214515 A1 Aug. 27, 2009

(51) Int. Cl.
*A61K 38/16* (2006.01)
*A61K 39/00* (2006.01)
*C07K 14/435* (2006.01)
*C07H 21/00* (2006.01)
*C12P 21/06* (2006.01)
*C12N 15/09* (2006.01)
*C12N 15/12* (2006.01)
*C12N 15/63* (2006.01)

(52) U.S. Cl. ..... 514/17.8; 514/21.3; 530/324; 536/23.5; 435/69.1; 435/69.3; 435/320.1

(58) Field of Classification Search ........................ None
See application file for complete search history.

(56) References Cited

U.S. PATENT DOCUMENTS

| 5,455,169 | A | * | 10/1995 | Mullan | 435/325 |
| 6,218,506 | B1 | | 4/2001 | Krafft et al. | |
| 2005/0112543 | A1 | | 5/2005 | Bush et al. | |

FOREIGN PATENT DOCUMENTS

| EP | 0 341 491 | | 11/1989 |
| WO | 99/09150 | | 2/1999 |
| WO | 01/10900 | | 2/2001 |
| WO | 02/03911 | A2 | 1/2002 |
| WO | 03/014329 | | 2/2003 |
| WO | 2004/031400 | * | 4/2004 |
| WO | 2004/067561 | | 8/2004 |
| WO | 2005/028511 | | 3/2005 |
| WO | 2005/041650 | A | 5/2005 |
| WO | 2005/123775 | | 12/2005 |
| WO | 2006/121656 | | 11/2006 |
| WO | 2006/128163 | | 11/2006 |

OTHER PUBLICATIONS

Myagkova 2001 (Bulletin of Experimental Biology and Medicine 131:156-159).*
Vickers (2002. Drugs Aging 19:487-494).*
Arispe, N., et al., "Alzheimer Disease Amyloid βProtein Forms Calcium Channels in Bilayer Membranes: Blockade by Tromethamine and Aluminum", PNAS, vol. 90, p. 567-571, 1993.
Armstrong, J., et al., "Familial Alzheimer disease associated with A713T mutation in *App*", Neurosci. Ltrs., vol. 370, pp. 241-243, 2004.
Barghorn, S., et al., "Globular amyloid β-peptide$_{1-42}$ oligomer—a homogenous and stable neuropathological protein in Alzheimer's disease", J Neurochem, vol. 95, No. 3, pp. 834-847, 2005.
Bitan, G.,et al., "Amyloid β-protein (Aβ) assembly: Aβ40 and Aβ42 oligomerize through distinct pathways", PNAS, vol. 100, No. 1, pp. 330-335, 2003.
Boyd-Kimball, D., et al., "Neurotoxicity and oxidative stress in D1M-substituted Alzheimer's Aβ(1-42): relevance to N-terminal methionine chemistry in small model peptides", Peptides, vol. 26, pp. 665-673, 2005.
Brunger et al., "*Crystallography & NMR System*: A New Software Suite for Macromolecular Structure Determination", Acta Crystallogr. D54 (Pt5), 905-21 (1998).
Carter, D.A., et al., "More missense in amyloid gene", Nat Genet, vol. 2, No. 4, pp. 255-256, Dec. 1992.
Chromy, B.A., et al., "Self-Assembly of Aβ$_{1-42}$ into Globular Neurotoxins", Biochem., vol. 42, pp. 12749-12760, 2003.
Dickson, D.W., et al., "Correlations of synaptic and pathological markers with cognition of the elderly", Neurobiol Aging, vol. 16, pp. 285-298, 1995.
Forsell, C. & Lannfelt, L., "Amyloid presursor protein mutation at codon 713 (Ala→Val) does not cause schizophrenia: non-pathogenic variant found at codon 705 (silent)", Neurosci. Ltrs., vol. 184, pp. 90-93, 1995.
Grabowski, T.J., et al., "Novel amyloid precursor protein mutation in an Iowa family with dementia and severe cerebral amyloid angiopathy", Ann Neurol, vol. 49, No. 6, pp. 697-705, Jun. 2001.

(Continued)

Primary Examiner — Elizabeth C Kemmerer
Assistant Examiner — Kimberly A Ballard
(74) Attorney, Agent, or Firm — Lisa V. Mueller; Michael Best & Friedrich LLP

(57) ABSTRACT

The subject invention relates to the cloning, expression and isolation of recombinant forms of beta-amyloid protein containing a N-terminal methionine (or one or more amino acids) as well as to methods of using this recombinant protein in the production of therapeutic antibodies, in the identification of therapeutic small molecules, and in the performance of diagnostic assays.

14 Claims, 47 Drawing Sheets

OTHER PUBLICATIONS

Helisalmi, S., et al., "Screening for amyloid beta precursor rotein codon 665, 670/671 and 717 mutations in Finnish patients with Alzheimer's disease", Neurosci. Ltrs., vol. 205, pp. 68-70, 1996.

Janssen, J.C., et al., "Early onset familial Alzheimer's Disease: Mutation frequency in 31 families", Neurology, vol. 60, No. 2, pp. 235-239, Jan. 2003.

Jones, C.T., et al., "Mutation in codon 713 of the βamyloid precursor protein gene presenting with schizophrenia", Nat Genet, vol. 1, No. 4, pp. 306-309, Jul. 1992.

Kakio, A., et al., "Interactions of Amyloid β-Protein with Various Gangliosides in Raft-Like Membranes: Importance of GM1 Ganglioside-Bound Form as an Endogenous Seed fr Alzheimer Amyloid", Biochem., vol. 41, pp. 7385-7390, 2002.

Kamino, K., et al., "Linkage and Mutational Analysis of Familial Alzheimer Disease Kndreds for the APP Gene Region", Am J Hum Genet, vol. 51, No. 5, pp. 998-1014, 1992.

Kumar-Singh, S., et al., "Dense-Core Senile Plaques in the Flemish Variant of Alzheimer's Disease Are Vasocentric", Am J Pathol, vol. 161, No. 2, pp. 507-520, 2002.

Lambert, M.P., et al., "Diffusible, nonfibrillar ligands derived from $A\beta_{1-42}$ are potent central nervous system neurotoxins", PNAS, vol. 95, No. 11, pp. 6448-6453, 1998.

Lashuel, H.A., et al., "Neurodegenerative disease: Amyloid pores from pathogenic mutations", Nature, vol. 418, No. 6895, pp. 291, 2002.

Lee, E.B., et al., "Secretion and Intracellular Generation of Truncated Aβ in β-Site Amyloid-β Precursor Protein-cleaving Enzyme Expressing Human Neurons", Journal of Biological Chemistry, vol. 278, pp. 4458-4466, 2003.

Lue, L.-F., et al., "Soluble Amyloid β Peptide Concentration as a Predictor of Synaptic Change in Alzheimer's Disease", Am J Pathol, vol. 155, No. 3, pp. 853-862, 1999.

Lührs, T., et al., "3D structure of Alzheimer's amyloid-β (1-42) fibrils", PNAS, vol. 102, No. 48, pp. 17342-17347, 2005.

Masters, C.L., et al., "Amyloid Plaque Core Protein in Alzheimer Disease and Down Syndrome", PNAS, vol. 82, pp. 4245-4249, 1985.

McLean, C.A., et al., "Soluble pool of Aβ amyloid as a determinant of severity of neurodegeneration in Alzheimer's disease", Ann Neurol, vol. 46, pp. 860-866, 1999.

Mullan, M., et al., "A pathogenic mutation for probable Alzheimer's disease in the APP gene at the N-terminus of β-amyloid", Nat Genet, vol. 1, No. 5, pp. 345-347, Aug. 1992.

Näslund, J., et al., "Relative Abundance of Alzheimer Aβ Amyloid Peptide Variants in Alzheimer Disease and Normal Aging", PNAS, vol. 91, No. 18, pp. 8378-8382, 1994.

Peacock, M.L., et al., "Novel amyloid precursor protein gene mutation (codon 665Asp) in a patient with late-onset Alzheimer's disease", Ann Neurol, vol. 35, No. 4, pp. 432-438, Apr. 1994.

Peacock, M.L., et al., "Novel polymorphism in the A4 region of the amyloid precursor protein gene in a patient without Alzheimer's disease", Neurology, vol. 43, No. 6, pp. 1254-1256, Jun. 1993.

Rangachari, V., et al., "Secondary Structure and Interfacial Aggregatoin of Amyloidβ(1-40) on Sodium Dodecyl Sulfate Micelles", Biochem., vol. 45, pp. 8639-8648, 2006.

Rossi, G., et al., "A family with Alzheimer disease and strokes associated with A713T mutation of the APP gene", Neurology, vol. 63, No. 5, pp. 910-912, 2004.

Russo, C., et al., "Neurobiology: Presenilin-1 mutations in Alzheimer's disease", Nature, vol. 405, No. 6786, pp. 531-532, 2000.

Saido, T.C., et al., "Dominant and differential deposition of distinct β-amyloid peptide species, $A\beta_{N3(pE)}$, in senile plaques", Neuron, vol. 14, pp. 457-466, 1995.

Sciaretta et al., "Aβ40-Lactam (D23/K28) Models a Conformatoin Highly Favorable for Nucleation of Amlyoid", Biochemistry 2005, 44: 6003-6014.

Selkoe, D.J., "Clearing the Brain's Amyloid Cobwebs", Neuron, vol. 32, pp. 177-180, 2001.

Sergeant, N., et al., "Truncated beta-amyloid peptide species in preclinical Alzheimer's disease as new targets for the vaccination approach", J of Neurochemistry, vol. 85, No. 6, pp. 1581-1591, 2003.

Terry, R.D., et al., "Physical basis of cognitive alterations in alzheimer's disease: Synapse loss is the major correlate of cognitive impairment", Ann Neurol, vol. 30, pp. 572-580, 1991.

Tsubuki, S., et al., "Dutch, Flemish, Italian, and Arctic mutations of APP and resistance of Aβ to physiologically relevant proteolytic degradation", Lancet, vol. 361, No. 9373, pp. 1957-1958, Jun. 7, 2003.

Van Broeckhoven, et al., "Amyloid beta protein precursor gene and hereditary cerebral hemorrhage with amyloidosis (Dutch)", Science, vol. 248, No. 4959, pp. 1120-1122, Jun. 1, 1990.

Wakutani, Y., et al., "Novel amyloid precursor protein gene missense mutation (D678N) in probable familial Alzheimer's disease", J Neurol Neurosurg Psychiatry, vol. 75, No. 7, pp. 1039-1042, Jul. 2004.

Wurth, C., et al., "Mutations that Reduce Aggregation of the Alzheimer's Aβ42 Peptide: an Unbiased Search for the Sequence Detrminants of Aβ Amyloidogenesis", J. Mol. Biol., vol. 319, pp. 1279-1290, 2002.

Yamamoto, N., et al., "Environment- and mutation-dependent aggregation behavior of Alzheimer amyloid β-protein", J. of Neurochem., vol. 90, pp. 62-69, 2004.

* cited by examiner

```
NdeI
CATATGGATG CGGAATTTCG CCATGATAGC GGCTATGAAG TGCATCATCA GAAACTGGTG TTTTCGCGG AAGATGTGGG CAGCAACAAA GGCGCGATTA
GTATACCTAC GCCTTAAAGC GGTACTATCG CCGATACTTC ACGTAGTAGT CTTTGACCAC AAAAGCGCC TTCTACACCC GTCGTTGTTT CCGCGCTAAT
                                              XhoI
                                              -----
                                                AvaI
                                                -----
TTGGCCTGAT GGTGGGTGGT GTGGTGATTG CGTGATCGAG
AACCGGACTA CCACCCACCA CACCACTAAC GCACTAGCTC
```

FIG.1-A

1 DAEFRHDSG YEVHHQKLVF FAEDVGSNKG AIIGLMVGGV VIA*

FIG.1-B

Full-length Amyloid Sequences
1-39: MDAEFRHDSG YEVHHQKLVF FAEDVGSNKG AIIGLMVGGV
1-40: MDAEFRHDSG YEVHHQKLVF FAEDVGSNKG AIIGLMVGGV V
1-41: MDAEFRHDSG YEVHHQKLVF FAEDVGSNKG AIIGLMVGGV VI
1-42: MDAEFRHDSG YEVHHQKLVF FAEDVGSNKG AIIGLMVGGV VIA
1-43: MDAEFRHDSG YEVHHQKLVF FAEDVGSNKG AIIGLMVGGV VIAT Truncated Amyloid Sequence from Thermolysin Cleavage
20-42: ........................ FAEDVGSNKG AIIGLMVGGV VIA

Dissolve lyophilized peptide in HFIP
- HFIP removed by lyophilization
- Dissolve in DMSO Dilute into PBS
- Add SDS to 0.2%, incubate several hours at 37°C.

Dilute 4X with water
- Final SDS = 0.05%, incubate overnight at 37°C.

Remove SDS by Dialysis

The beta-sheet globulomer is described in Figure 20.

The beta-sheet globulomer is described in Figure 20.

| ATOM | 1 | HA | GLN | 15 | 89.898 | 71.968 | 50.323 | 1.00 | 0.00 |
|---|---|---|---|---|---|---|---|---|---|
| ATOM | 2 | CB | GLN | 15 | 91.447 | 73.251 | 51.060 | 1.00 | 0.00 |
| ATOM | 3 | HB1 | GLN | 15 | 91.396 | 73.714 | 50.085 | 1.00 | 0.00 |
| ATOM | 4 | HB2 | GLN | 15 | 92.314 | 72.609 | 51.099 | 1.00 | 0.00 |
| ATOM | 5 | CG | GLN | 15 | 91.618 | 74.347 | 52.099 | 1.00 | 0.00 |
| ATOM | 6 | HG1 | GLN | 15 | 90.822 | 74.266 | 52.824 | 1.00 | 0.00 |
| ATOM | 7 | HG2 | GLN | 15 | 91.558 | 75.306 | 51.606 | 1.00 | 0.00 |
| ATOM | 8 | CD | GLN | 15 | 92.946 | 74.259 | 52.825 | 1.00 | 0.00 |
| ATOM | 9 | OE1 | GLN | 15 | 94.010 | 74.338 | 52.210 | 1.00 | 0.00 |
| ATOM | 10 | NE2 | GLN | 15 | 92.891 | 74.095 | 54.142 | 1.00 | 0.00 |
| ATOM | 11 | HE21 | GLN | 15 | 92.008 | 74.040 | 54.564 | 1.00 | 0.00 |
| ATOM | 12 | HE22 | GLN | 15 | 93.734 | 74.035 | 54.636 | 1.00 | 0.00 |
| ATOM | 13 | C | GLN | 15 | 90.490 | 71.273 | 52.251 | 1.00 | 0.00 |
| ATOM | 14 | O | GLN | 15 | 91.429 | 70.500 | 52.057 | 1.00 | 0.00 |
| ATOM | 15 | N | GLN | 15 | 89.074 | 73.248 | 51.758 | 1.00 | 0.00 |
| ATOM | 16 | HT1 | GLN | 15 | 88.836 | 72.993 | 52.738 | 1.00 | 0.00 |
| ATOM | 17 | HT2 | GLN | 15 | 88.234 | 73.111 | 51.162 | 1.00 | 0.00 |
| ATOM | 18 | HT3 | GLN | 15 | 89.347 | 74.251 | 51.729 | 1.00 | 0.00 |
| ATOM | 19 | CA | GLN | 15 | 90.192 | 72.400 | 51.269 | 1.00 | 0.00 |
| ATOM | 20 | N | LYS | 16 | 89.686 | 71.184 | 53.305 | 1.00 | 0.00 |
| ATOM | 21 | HN | LYS | 16 | 88.955 | 71.829 | 53.404 | 1.00 | 0.00 |
| ATOM | 22 | CA | LYS | 16 | 89.863 | 70.150 | 54.317 | 1.00 | 0.00 |
| ATOM | 23 | HA | LYS | 16 | 90.871 | 69.770 | 54.230 | 1.00 | 0.00 |
| ATOM | 24 | CB | LYS | 16 | 89.673 | 70.738 | 55.716 | 1.00 | 0.00 |
| ATOM | 25 | HB1 | LYS | 16 | 90.466 | 70.381 | 56.356 | 1.00 | 0.00 |
| ATOM | 26 | HB2 | LYS | 16 | 88.725 | 70.401 | 56.110 | 1.00 | 0.00 |
| ATOM | 27 | CG | LYS | 16 | 89.687 | 72.258 | 55.744 | 1.00 | 0.00 |
| ATOM | 28 | HG1 | LYS | 16 | 88.738 | 72.623 | 55.379 | 1.00 | 0.00 |
| ATOM | 29 | HG2 | LYS | 16 | 90.481 | 72.613 | 55.105 | 1.00 | 0.00 |
| ATOM | 30 | CD | LYS | 16 | 89.913 | 72.788 | 57.151 | 1.00 | 0.00 |
| ATOM | 31 | HD1 | LYS | 16 | 89.988 | 73.865 | 57.111 | 1.00 | 0.00 |
| ATOM | 32 | HD2 | LYS | 16 | 90.833 | 72.375 | 57.537 | 1.00 | 0.00 |
| ATOM | 33 | CE | LYS | 16 | 88.773 | 72.405 | 58.080 | 1.00 | 0.00 |
| ATOM | 34 | HE1 | LYS | 16 | 88.751 | 73.099 | 58.907 | 1.00 | 0.00 |
| ATOM | 35 | HE2 | LYS | 16 | 88.948 | 71.407 | 58.453 | 1.00 | 0.00 |
| ATOM | 36 | NZ | LYS | 16 | 87.456 | 72.437 | 57.386 | 1.00 | 0.00 |
| ATOM | 37 | HZ1 | LYS | 16 | 86.702 | 72.677 | 58.061 | 1.00 | 0.00 |
| ATOM | 38 | HZ2 | LYS | 16 | 87.249 | 71.508 | 56.968 | 1.00 | 0.00 |
| ATOM | 39 | HZ3 | LYS | 16 | 87.468 | 73.150 | 56.629 | 1.00 | 0.00 |
| ATOM | 40 | C | LYS | 16 | 88.885 | 69.001 | 54.099 | 1.00 | 0.00 |

FIG.24-A

| ATOM | 41 | O    | LYS | 16 | 88.409 | 68.781 | 52.985 | 1.00 | 0.00 |
| ATOM | 42 | N    | LEU | 17 | 88.588 | 68.271 | 55.169 | 1.00 | 0.00 |
| ATOM | 43 | HN   | LEU | 17 | 88.999 | 68.494 | 56.029 | 1.00 | 0.00 |
| ATOM | 44 | CA   | LEU | 17 | 87.665 | 67.144 | 55.092 | 1.00 | 0.00 |
| ATOM | 45 | HA   | LEU | 17 | 87.232 | 67.138 | 54.103 | 1.00 | 0.00 |
| ATOM | 46 | CB   | LEU | 17 | 88.413 | 65.829 | 55.316 | 1.00 | 0.00 |
| ATOM | 47 | HB1  | LEU | 17 | 87.847 | 65.231 | 56.014 | 1.00 | 0.00 |
| ATOM | 48 | HB2  | LEU | 17 | 89.373 | 66.055 | 55.757 | 1.00 | 0.00 |
| ATOM | 49 | CG   | LEU | 17 | 88.647 | 64.996 | 54.054 | 1.00 | 0.00 |
| ATOM | 50 | HG   | LEU | 17 | 89.097 | 64.054 | 54.330 | 1.00 | 0.00 |
| ATOM | 51 | CD1  | LEU | 17 | 87.327 | 64.701 | 53.358 | 1.00 | 0.00 |
| ATOM | 52 | HD11 | LEU | 17 | 86.512 | 64.859 | 54.049 | 1.00 | 0.00 |
| ATOM | 53 | HD12 | LEU | 17 | 87.320 | 63.675 | 53.020 | 1.00 | 0.00 |
| ATOM | 54 | HD13 | LEU | 17 | 87.213 | 65.360 | 52.510 | 1.00 | 0.00 |
| ATOM | 55 | CD2  | LEU | 17 | 89.599 | 65.716 | 53.112 | 1.00 | 0.00 |
| ATOM | 56 | HD21 | LEU | 17 | 90.565 | 65.817 | 53.584 | 1.00 | 0.00 |
| ATOM | 57 | HD22 | LEU | 17 | 89.207 | 66.696 | 52.882 | 1.00 | 0.00 |
| ATOM | 58 | HD23 | LEU | 17 | 89.702 | 65.147 | 52.200 | 1.00 | 0.00 |
| ATOM | 59 | C    | LEU | 17 | 86.545 | 67.288 | 56.118 | 1.00 | 0.00 |
| ATOM | 60 | O    | LEU | 17 | 86.333 | 68.366 | 56.672 | 1.00 | 0.00 |
| ATOM | 61 | N    | VAL | 18 | 85.831 | 66.194 | 56.365 | 1.00 | 0.00 |
| ATOM | 62 | HN   | VAL | 18 | 86.049 | 65.364 | 55.892 | 1.00 | 0.00 |
| ATOM | 63 | CA   | VAL | 18 | 84.733 | 66.201 | 57.323 | 1.00 | 0.00 |
| ATOM | 64 | HA   | VAL | 18 | 84.713 | 67.170 | 57.801 | 1.00 | 0.00 |
| ATOM | 65 | CB   | VAL | 18 | 83.378 | 65.980 | 56.625 | 1.00 | 0.00 |
| ATOM | 66 | HB   | VAL | 18 | 82.813 | 65.261 | 57.199 | 1.00 | 0.00 |
| ATOM | 67 | CG1  | VAL | 18 | 82.584 | 67.276 | 56.574 | 1.00 | 0.00 |
| ATOM | 68 | HG11 | VAL | 18 | 82.422 | 67.638 | 57.578 | 1.00 | 0.00 |
| ATOM | 69 | HG12 | VAL | 18 | 81.632 | 67.097 | 56.097 | 1.00 | 0.00 |
| ATOM | 70 | HG13 | VAL | 18 | 83.136 | 68.014 | 56.010 | 1.00 | 0.00 |
| ATOM | 71 | CG2  | VAL | 18 | 83.583 | 65.417 | 55.226 | 1.00 | 0.00 |
| ATOM | 72 | HG21 | VAL | 18 | 83.752 | 64.352 | 55.288 | 1.00 | 0.00 |
| ATOM | 73 | HG22 | VAL | 18 | 84.439 | 65.891 | 54.769 | 1.00 | 0.00 |
| ATOM | 74 | HG23 | VAL | 18 | 82.704 | 65.608 | 54.629 | 1.00 | 0.00 |
| ATOM | 75 | C    | VAL | 18 | 84.922 | 65.128 | 58.390 | 1.00 | 0.00 |
| ATOM | 76 | O    | VAL | 18 | 84.084 | 64.239 | 58.545 | 1.00 | 0.00 |
| ATOM | 77 | N    | PHE | 19 | 86.027 | 65.216 | 59.124 | 1.00 | 0.00 |
| ATOM | 78 | HN   | PHE | 19 | 86.660 | 65.943 | 58.949 | 1.00 | 0.00 |
| ATOM | 79 | CA   | PHE | 19 | 86.321 | 64.254 | 60.179 | 1.00 | 0.00 |
| ATOM | 80 | HA   | PHE | 19 | 85.726 | 63.371 | 59.998 | 1.00 | 0.00 |

FIG.24-B

| ATOM | 81 | CB | PHE | 19 | 87.802 | 63.870 | 60.151 | 1.00 | 0.00 |
|------|-----|-----|-----|----|--------|--------|--------|------|------|
| ATOM | 82 | HB1 | PHE | 19 | 88.398 | 64.769 | 60.107 | 1.00 | 0.00 |
| ATOM | 83 | HB2 | PHE | 19 | 87.995 | 63.273 | 59.273 | 1.00 | 0.00 |
| ATOM | 84 | CG | PHE | 19 | 88.237 | 63.079 | 61.353 | 1.00 | 0.00 |
| ATOM | 85 | CD1 | PHE | 19 | 89.266 | 63.532 | 62.165 | 1.00 | 0.00 |
| ATOM | 86 | HD1 | PHE | 19 | 89.758 | 64.464 | 61.930 | 1.00 | 0.00 |
| ATOM | 87 | CD2 | PHE | 19 | 87.616 | 61.882 | 61.669 | 1.00 | 0.00 |
| ATOM | 88 | HD2 | PHE | 19 | 86.814 | 61.520 | 61.043 | 1.00 | 0.00 |
| ATOM | 89 | CE1 | PHE | 19 | 89.666 | 62.804 | 63.270 | 1.00 | 0.00 |
| ATOM | 90 | HE1 | PHE | 19 | 90.468 | 63.166 | 63.895 | 1.00 | 0.00 |
| ATOM | 91 | CE2 | PHE | 19 | 88.012 | 61.150 | 62.773 | 1.00 | 0.00 |
| ATOM | 92 | HE2 | PHE | 19 | 87.520 | 60.218 | 63.008 | 1.00 | 0.00 |
| ATOM | 93 | CZ | PHE | 19 | 89.038 | 61.611 | 63.574 | 1.00 | 0.00 |
| ATOM | 94 | HZ | PHE | 19 | 89.348 | 61.041 | 64.437 | 1.00 | 0.00 |
| ATOM | 95 | C | PHE | 19 | 85.958 | 64.821 | 61.547 | 1.00 | 0.00 |
| ATOM | 96 | O | PHE | 19 | 86.705 | 65.612 | 62.122 | 1.00 | 0.00 |
| ATOM | 97 | N | PHE | 20 | 84.805 | 64.409 | 62.064 | 1.00 | 0.00 |
| ATOM | 98 | HN | PHE | 20 | 84.254 | 63.777 | 61.558 | 1.00 | 0.00 |
| ATOM | 99 | CA | PHE | 20 | 84.339 | 64.876 | 63.364 | 1.00 | 0.00 |
| ATOM | 100 | HA | PHE | 20 | 84.872 | 65.785 | 63.601 | 1.00 | 0.00 |
| ATOM | 101 | CB | PHE | 20 | 82.840 | 65.177 | 63.314 | 1.00 | 0.00 |
| ATOM | 102 | HB1 | PHE | 20 | 82.360 | 64.466 | 62.658 | 1.00 | 0.00 |
| ATOM | 103 | HB2 | PHE | 20 | 82.694 | 66.174 | 62.924 | 1.00 | 0.00 |
| ATOM | 104 | CG | PHE | 20 | 82.166 | 65.103 | 64.654 | 1.00 | 0.00 |
| ATOM | 105 | CD1 | PHE | 20 | 81.305 | 64.059 | 64.957 | 1.00 | 0.00 |
| ATOM | 106 | HD1 | PHE | 20 | 81.120 | 63.292 | 64.219 | 1.00 | 0.00 |
| ATOM | 107 | CD2 | PHE | 20 | 82.393 | 66.078 | 65.613 | 1.00 | 0.00 |
| ATOM | 108 | HD2 | PHE | 20 | 83.061 | 66.896 | 65.388 | 1.00 | 0.00 |
| ATOM | 109 | CE1 | PHE | 20 | 80.684 | 63.990 | 66.189 | 1.00 | 0.00 |
| ATOM | 110 | HE1 | PHE | 20 | 80.015 | 63.171 | 66.413 | 1.00 | 0.00 |
| ATOM | 111 | CE2 | PHE | 20 | 81.775 | 66.013 | 66.847 | 1.00 | 0.00 |
| ATOM | 112 | HE2 | PHE | 20 | 81.960 | 66.780 | 67.585 | 1.00 | 0.00 |
| ATOM | 113 | CZ | PHE | 20 | 80.919 | 64.968 | 67.136 | 1.00 | 0.00 |
| ATOM | 114 | HZ | PHE | 20 | 80.435 | 64.916 | 68.099 | 1.00 | 0.00 |
| ATOM | 115 | C | PHE | 20 | 84.625 | 63.842 | 64.448 | 1.00 | 0.00 |
| ATOM | 116 | O | PHE | 20 | 84.096 | 62.731 | 64.416 | 1.00 | 0.00 |
| ATOM | 117 | N | ALA | 21 | 85.466 | 64.216 | 65.407 | 1.00 | 0.00 |
| ATOM | 118 | HN | ALA | 21 | 85.856 | 65.114 | 65.379 | 1.00 | 0.00 |
| ATOM | 119 | CA | ALA | 21 | 85.822 | 63.321 | 66.501 | 1.00 | 0.00 |
| ATOM | 120 | HA | ALA | 21 | 85.257 | 62.408 | 66.383 | 1.00 | 0.00 |

FIG.24-C

| | | | | | | | | | |
|---|---|---|---|---|---|---|---|---|---|
| ATOM | 121 | CB  | ALA | 21 | 87.302 | 62.972 | 66.437 | 1.00 | 0.00 |
| ATOM | 122 | HB1 | ALA | 21 | 87.559 | 62.337 | 67.271 | 1.00 | 0.00 |
| ATOM | 123 | HB2 | ALA | 21 | 87.887 | 63.879 | 66.480 | 1.00 | 0.00 |
| ATOM | 124 | HB3 | ALA | 21 | 87.509 | 62.454 | 65.512 | 1.00 | 0.00 |
| ATOM | 125 | C   | ALA | 21 | 85.481 | 63.942 | 67.852 | 1.00 | 0.00 |
| ATOM | 126 | O   | ALA | 21 | 86.025 | 64.982 | 68.224 | 1.00 | 0.00 |
| ATOM | 127 | N   | GLU | 22 | 84.576 | 63.296 | 68.581 | 1.00 | 0.00 |
| ATOM | 128 | HN  | GLU | 22 | 84.178 | 62.473 | 68.229 | 1.00 | 0.00 |
| ATOM | 129 | CA  | GLU | 22 | 84.159 | 63.784 | 69.891 | 1.00 | 0.00 |
| ATOM | 130 | HA  | GLU | 22 | 84.479 | 64.810 | 69.980 | 1.00 | 0.00 |
| ATOM | 131 | CB  | GLU | 22 | 82.636 | 63.725 | 70.018 | 1.00 | 0.00 |
| ATOM | 132 | HB1 | GLU | 22 | 82.216 | 64.627 | 69.597 | 1.00 | 0.00 |
| ATOM | 133 | HB2 | GLU | 22 | 82.375 | 63.673 | 71.065 | 1.00 | 0.00 |
| ATOM | 134 | CG  | GLU | 22 | 82.011 | 62.534 | 69.312 | 1.00 | 0.00 |
| ATOM | 135 | HG1 | GLU | 22 | 82.602 | 61.655 | 69.525 | 1.00 | 0.00 |
| ATOM | 136 | HG2 | GLU | 22 | 82.015 | 62.719 | 68.248 | 1.00 | 0.00 |
| ATOM | 137 | CD  | GLU | 22 | 80.583 | 62.278 | 69.752 | 1.00 | 0.00 |
| ATOM | 138 | OE1 | GLU | 22 | 80.183 | 62.813 | 70.807 | 1.00 | 0.00 |
| ATOM | 139 | OE2 | GLU | 22 | 79.865 | 61.543 | 69.042 | 1.00 | 0.00 |
| ATOM | 140 | C   | GLU | 22 | 84.805 | 62.967 | 71.006 | 1.00 | 0.00 |
| ATOM | 141 | O   | GLU | 22 | 84.118 | 62.445 | 71.884 | 1.00 | 0.00 |
| ATOM | 142 | N   | ASP | 23 | 86.129 | 62.862 | 70.967 | 1.00 | 0.00 |
| ATOM | 143 | HN  | ASP | 23 | 86.622 | 63.301 | 70.242 | 1.00 | 0.00 |
| ATOM | 144 | CA  | ASP | 23 | 86.867 | 62.109 | 71.975 | 1.00 | 0.00 |
| ATOM | 145 | HA  | ASP | 23 | 86.161 | 61.489 | 72.506 | 1.00 | 0.00 |
| ATOM | 146 | CB  | ASP | 23 | 87.913 | 61.214 | 71.309 | 1.00 | 0.00 |
| ATOM | 147 | HB1 | ASP | 23 | 88.898 | 61.607 | 71.515 | 1.00 | 0.00 |
| ATOM | 148 | HB2 | ASP | 23 | 87.748 | 61.210 | 70.242 | 1.00 | 0.00 |
| ATOM | 149 | CG  | ASP | 23 | 87.852 | 59.783 | 71.808 | 1.00 | 0.00 |
| ATOM | 150 | OD1 | ASP | 23 | 86.732 | 59.242 | 71.923 | 1.00 | 0.00 |
| ATOM | 151 | OD2 | ASP | 23 | 88.924 | 59.204 | 72.083 | 1.00 | 0.00 |
| ATOM | 152 | C   | ASP | 23 | 87.543 | 63.048 | 72.969 | 1.00 | 0.00 |
| ATOM | 153 | O   | ASP | 23 | 88.582 | 63.638 | 72.674 | 1.00 | 0.00 |
| ATOM | 154 | N   | VAL | 24 | 86.949 | 63.177 | 74.151 | 1.00 | 0.00 |
| ATOM | 155 | HN  | VAL | 24 | 86.125 | 62.677 | 74.330 | 1.00 | 0.00 |
| ATOM | 156 | CA  | VAL | 24 | 87.493 | 64.044 | 75.188 | 1.00 | 0.00 |
| ATOM | 157 | HA  | VAL | 24 | 88.160 | 64.751 | 74.716 | 1.00 | 0.00 |
| ATOM | 158 | CB  | VAL | 24 | 86.380 | 64.834 | 75.902 | 1.00 | 0.00 |
| ATOM | 159 | HB  | VAL | 24 | 86.801 | 65.290 | 76.786 | 1.00 | 0.00 |
| ATOM | 160 | CG1 | VAL | 24 | 85.849 | 65.939 | 75.004 | 1.00 | 0.00 |

FIG.24-D

| ATOM | 161 | HG11 | VAL | 24 | 86.622 | 66.676 | 74.843 | 1.00 | 0.00 |
|------|-----|------|-----|----|--------|--------|--------|------|------|
| ATOM | 162 | HG12 | VAL | 24 | 84.998 | 66.409 | 75.475 | 1.00 | 0.00 |
| ATOM | 163 | HG13 | VAL | 24 | 85.548 | 65.519 | 74.055 | 1.00 | 0.00 |
| ATOM | 164 | CG2  | VAL | 24 | 85.258 | 63.902 | 76.335 | 1.00 | 0.00 |
| ATOM | 165 | HG21 | VAL | 24 | 85.092 | 64.007 | 77.396 | 1.00 | 0.00 |
| ATOM | 166 | HG22 | VAL | 24 | 85.532 | 62.881 | 76.113 | 1.00 | 0.00 |
| ATOM | 167 | HG23 | VAL | 24 | 84.354 | 64.156 | 75.802 | 1.00 | 0.00 |
| ATOM | 168 | C    | VAL | 24 | 88.275 | 63.242 | 76.223 | 1.00 | 0.00 |
| ATOM | 169 | O    | VAL | 24 | 88.224 | 63.534 | 77.417 | 1.00 | 0.00 |
| ATOM | 170 | N    | GLY | 25 | 88.997 | 62.230 | 75.755 | 1.00 | 0.00 |
| ATOM | 171 | HN   | GLY | 25 | 88.997 | 62.043 | 74.793 | 1.00 | 0.00 |
| ATOM | 172 | CA   | GLY | 25 | 89.782 | 61.401 | 76.651 | 1.00 | 0.00 |
| ATOM | 173 | HA1  | GLY | 25 | 89.633 | 60.364 | 76.389 | 1.00 | 0.00 |
| ATOM | 174 | HA2  | GLY | 25 | 89.439 | 61.559 | 77.663 | 1.00 | 0.00 |
| ATOM | 175 | C    | GLY | 25 | 91.263 | 61.717 | 76.580 | 1.00 | 0.00 |
| ATOM | 176 | O    | GLY | 25 | 92.039 | 61.282 | 77.430 | 1.00 | 0.00 |
| ATOM | 177 | N    | SER | 26 | 91.654 | 62.477 | 75.562 | 1.00 | 0.00 |
| ATOM | 178 | HN   | SER | 26 | 90.986 | 62.792 | 74.917 | 1.00 | 0.00 |
| ATOM | 179 | CA   | SER | 26 | 93.051 | 62.853 | 75.380 | 1.00 | 0.00 |
| ATOM | 180 | HA   | SER | 26 | 93.495 | 62.961 | 76.358 | 1.00 | 0.00 |
| ATOM | 181 | CB   | SER | 26 | 93.799 | 61.763 | 74.611 | 1.00 | 0.00 |
| ATOM | 182 | HB1  | SER | 26 | 93.813 | 62.011 | 73.560 | 1.00 | 0.00 |
| ATOM | 183 | HB2  | SER | 26 | 93.296 | 60.817 | 74.751 | 1.00 | 0.00 |
| ATOM | 184 | OG   | SER | 26 | 95.134 | 61.640 | 75.069 | 1.00 | 0.00 |
| ATOM | 185 | HG   | SER | 26 | 95.464 | 62.503 | 75.330 | 1.00 | 0.00 |
| ATOM | 186 | C    | SER | 26 | 93.163 | 64.182 | 74.639 | 1.00 | 0.00 |
| ATOM | 187 | O    | SER | 26 | 93.453 | 65.216 | 75.240 | 1.00 | 0.00 |
| ATOM | 188 | N    | ASN | 27 | 92.930 | 64.145 | 73.331 | 1.00 | 0.00 |
| ATOM | 189 | HN   | ASN | 27 | 92.702 | 63.290 | 72.910 | 1.00 | 0.00 |
| ATOM | 190 | CA   | ASN | 27 | 93.004 | 65.346 | 72.507 | 1.00 | 0.00 |
| ATOM | 191 | HA   | ASN | 27 | 92.415 | 66.114 | 72.986 | 1.00 | 0.00 |
| ATOM | 192 | CB   | ASN | 27 | 94.453 | 65.826 | 72.397 | 1.00 | 0.00 |
| ATOM | 193 | HB1  | ASN | 27 | 94.961 | 65.247 | 71.640 | 1.00 | 0.00 |
| ATOM | 194 | HB2  | ASN | 27 | 94.946 | 65.682 | 73.347 | 1.00 | 0.00 |
| ATOM | 195 | CG   | ASN | 27 | 94.550 | 67.293 | 72.026 | 1.00 | 0.00 |
| ATOM | 196 | OD1  | ASN | 27 | 94.503 | 68.169 | 72.889 | 1.00 | 0.00 |
| ATOM | 197 | ND2  | ASN | 27 | 94.684 | 67.568 | 70.733 | 1.00 | 0.00 |
| ATOM | 198 | HD21 | ASN | 27 | 94.713 | 66.820 | 70.101 | 1.00 | 0.00 |
| ATOM | 199 | HD22 | ASN | 27 | 94.750 | 68.508 | 70.465 | 1.00 | 0.00 |
| ATOM | 200 | C    | ASN | 27 | 92.436 | 65.087 | 71.115 | 1.00 | 0.00 |

FIG.24-E

| | | | | | | | | | |
|---|---|---|---|---|---|---|---|---|---|
| ATOM | 201 | O | ASN | 27 | 93.083 | 65.374 | 70.107 | 1.00 | 0.00 |
| ATOM | 202 | N | LYS | 28 | 91.224 | 64.544 | 71.066 | 1.00 | 0.00 |
| ATOM | 203 | HN | LYS | 28 | 90.757 | 64.341 | 71.903 | 1.00 | 0.00 |
| ATOM | 204 | CA | LYS | 28 | 90.571 | 64.246 | 69.798 | 1.00 | 0.00 |
| ATOM | 205 | HA | LYS | 28 | 91.032 | 64.857 | 69.036 | 1.00 | 0.00 |
| ATOM | 206 | CB | LYS | 28 | 90.759 | 62.772 | 69.436 | 1.00 | 0.00 |
| ATOM | 207 | HB1 | LYS | 28 | 89.790 | 62.296 | 69.399 | 1.00 | 0.00 |
| ATOM | 208 | HB2 | LYS | 28 | 91.354 | 62.298 | 70.203 | 1.00 | 0.00 |
| ATOM | 209 | CG | LYS | 28 | 91.447 | 62.556 | 68.098 | 1.00 | 0.00 |
| ATOM | 210 | HG1 | LYS | 28 | 90.979 | 63.189 | 67.358 | 1.00 | 0.00 |
| ATOM | 211 | HG2 | LYS | 28 | 91.337 | 61.521 | 67.810 | 1.00 | 0.00 |
| ATOM | 212 | CD | LYS | 28 | 92.927 | 62.892 | 68.172 | 1.00 | 0.00 |
| ATOM | 213 | HD1 | LYS | 28 | 93.106 | 63.494 | 69.051 | 1.00 | 0.00 |
| ATOM | 214 | HD2 | LYS | 28 | 93.205 | 63.448 | 67.290 | 1.00 | 0.00 |
| ATOM | 215 | CE | LYS | 28 | 93.780 | 61.636 | 68.252 | 1.00 | 0.00 |
| ATOM | 216 | HE1 | LYS | 28 | 94.752 | 61.900 | 68.641 | 1.00 | 0.00 |
| ATOM | 217 | HE2 | LYS | 28 | 93.890 | 61.227 | 67.258 | 1.00 | 0.00 |
| ATOM | 218 | NZ | LYS | 28 | 93.168 | 60.604 | 69.134 | 1.00 | 0.00 |
| ATOM | 219 | HZ1 | LYS | 28 | 92.412 | 60.102 | 68.626 | 1.00 | 0.00 |
| ATOM | 220 | HZ2 | LYS | 28 | 92.763 | 61.052 | 69.981 | 1.00 | 0.00 |
| ATOM | 221 | HZ3 | LYS | 28 | 93.888 | 59.915 | 69.431 | 1.00 | 0.0 |
| ATOM | 222 | C | LYS | 28 | 89.085 | 64.580 | 69.864 | 1.00 | 0.00 |
| ATOM | 223 | O | LYS | 28 | 88.268 | 63.959 | 69.185 | 1.00 | 0.00 |
| ATOM | 224 | N | GLY | 29 | 88.741 | 65.564 | 70.689 | 1.00 | 0.00 |
| ATOM | 225 | HN | GLY | 29 | 89.436 | 66.023 | 71.206 | 1.00 | 0.00 |
| ATOM | 226 | CA | GLY | 29 | 87.354 | 65.963 | 70.829 | 1.00 | 0.00 |
| ATOM | 227 | HA1 | GLY | 29 | 87.135 | 66.103 | 71.878 | 1.00 | 0.00 |
| ATOM | 228 | HA2 | GLY | 29 | 86.724 | 65.176 | 70.443 | 1.00 | 0.00 |
| ATOM | 229 | C | GLY | 29 | 87.043 | 67.248 | 70.088 | 1.00 | 0.00 |
| ATOM | 230 | O | GLY | 29 | 86.464 | 68.175 | 70.654 | 1.00 | 0.00 |
| ATOM | 231 | N | ALA | 30 | 87.428 | 67.302 | 68.818 | 1.00 | 0.00 |
| ATOM | 232 | HN | ALA | 30 | 87.881 | 66.527 | 68.422 | 1.00 | 0.00 |
| ATOM | 233 | CA | ALA | 30 | 87.190 | 68.483 | 67.997 | 1.00 | 0.00 |
| ATOM | 234 | HA | ALA | 30 | 86.389 | 69.048 | 68.452 | 1.00 | 0.00 |
| ATOM | 235 | CB | ALA | 30 | 88.431 | 69.362 | 67.967 | 1.00 | 0.00 |
| ATOM | 236 | HB1 | ALA | 30 | 88.713 | 69.622 | 68.977 | 1.00 | 0.00 |
| ATOM | 237 | HB2 | ALA | 30 | 88.220 | 70.263 | 67.409 | 1.00 | 0.00 |
| ATOM | 238 | HB3 | ALA | 30 | 89.240 | 68.827 | 67.494 | 1.00 | 0.00 |
| ATOM | 239 | C | ALA | 30 | 86.778 | 68.097 | 66.581 | 1.00 | 0.00 |
| ATOM | 240 | O | ALA | 30 | 86.543 | 66.925 | 66.289 | 1.00 | 0.00 |

FIG.24-F

| ATOM | 241 | N    | ILE | 31 | 86.694 | 69.093 | 65.704 | 1.00 | 0.00 |
|------|-----|------|-----|----|--------|--------|--------|------|------|
| ATOM | 242 | HN   | ILE | 31 | 86.893 | 70.006 | 65.998 | 1.00 | 0.00 |
| ATOM | 243 | CA   | ILE | 31 | 86.314 | 68.861 | 64.316 | 1.00 | 0.00 |
| ATOM | 244 | HA   | ILE | 31 | 86.080 | 67.812 | 64.204 | 1.00 | 0.00 |
| ATOM | 245 | CB   | ILE | 31 | 85.066 | 69.679 | 63.931 | 1.00 | 0.00 |
| ATOM | 246 | HB   | ILE | 31 | 85.381 | 70.685 | 63.700 | 1.00 | 0.00 |
| ATOM | 247 | CG1  | ILE | 31 | 84.075 | 69.719 | 65.095 | 1.00 | 0.00 |
| ATOM | 248 | HG11 | ILE | 31 | 84.347 | 68.962 | 65.817 | 1.00 | 0.00 |
| ATOM | 249 | HG12 | ILE | 31 | 83.083 | 69.515 | 64.722 | 1.00 | 0.00 |
| ATOM | 250 | CG2  | ILE | 31 | 84.411 | 69.093 | 62.689 | 1.00 | 0.00 |
| ATOM | 251 | HG21 | ILE | 31 | 85.170 | 68.862 | 61.957 | 1.00 | 0.00 |
| ATOM | 252 | HG22 | ILE | 31 | 83.718 | 69.810 | 62.276 | 1.00 | 0.00 |
| ATOM | 253 | HG23 | ILE | 31 | 83.880 | 68.191 | 62.955 | 1.00 | 0.00 |
| ATOM | 254 | CD1  | ILE | 31 | 84.037 | 71.052 | 65.810 | 1.00 | 0.00 |
| ATOM | 255 | HD11 | ILE | 31 | 84.994 | 71.240 | 66.274 | 1.00 | 0.00 |
| ATOM | 256 | HD12 | ILE | 31 | 83.267 | 71.032 | 66.568 | 1.00 | 0.00 |
| ATOM | 257 | HD13 | ILE | 31 | 83.821 | 71.836 | 65.099 | 1.00 | 0.00 |
| ATOM | 258 | C    | ILE | 31 | 87.454 | 69.219 | 63.369 | 1.00 | 0.00 |
| ATOM | 259 | O    | ILE | 31 | 87.865 | 70.376 | 63.288 | 1.00 | 0.00 |
| ATOM | 260 | N    | ILE | 32 | 87.960 | 68.220 | 62.654 | 1.00 | 0.00 |
| ATOM | 261 | HN   | ILE | 32 | 87.589 | 67.319 | 62.759 | 1.00 | 0.00 |
| ATOM | 262 | CA   | ILE | 32 | 89.054 | 68.434 | 61.714 | 1.00 | 0.00 |
| ATOM | 263 | HA   | ILE | 32 | 89.078 | 69.484 | 61.463 | 1.00 | 0.00 |
| ATOM | 264 | CB   | ILE | 32 | 90.412 | 68.055 | 62.337 | 1.00 | 0.00 |
| ATOM | 265 | HB   | ILE | 32 | 90.980 | 67.507 | 61.600 | 1.00 | 0.00 |
| ATOM | 266 | CG1  | ILE | 32 | 90.206 | 67.171 | 63.568 | 1.00 | 0.00 |
| ATOM | 267 | HG11 | ILE | 32 | 89.550 | 66.353 | 63.310 | 1.00 | 0.00 |
| ATOM | 268 | HG12 | ILE | 32 | 89.751 | 67.757 | 64.352 | 1.00 | 0.00 |
| ATOM | 269 | CG2  | ILE | 32 | 91.196 | 69.307 | 62.702 | 1.00 | 0.00 |
| ATOM | 270 | HG21 | ILE | 32 | 91.561 | 69.778 | 61.801 | 1.00 | 0.00 |
| ATOM | 271 | HG22 | ILE | 32 | 92.031 | 69.038 | 63.332 | 1.00 | 0.00 |
| ATOM | 272 | HG23 | ILE | 32 | 90.552 | 69.993 | 63.231 | 1.00 | 0.00 |
| ATOM | 273 | CD1  | ILE | 32 | 91.490 | 66.585 | 64.113 | 1.00 | 0.00 |
| ATOM | 274 | HD11 | ILE | 32 | 91.764 | 67.100 | 65.022 | 1.00 | 0.00 |
| ATOM | 275 | HD12 | ILE | 32 | 92.277 | 66.701 | 63.382 | 1.00 | 0.00 |
| ATOM | 276 | HD13 | ILE | 32 | 91.346 | 65.535 | 64.323 | 1.00 | 0.00 |
| ATOM | 277 | C    | ILE | 32 | 88.851 | 67.625 | 60.438 | 1.00 | 0.00 |
| ATOM | 278 | O    | ILE | 32 | 87.770 | 67.090 | 60.196 | 1.00 | 0.00 |
| ATOM | 279 | N    | GLY | 33 | 89.898 | 67.541 | 59.625 | 1.00 | 0.00 |
| ATOM | 280 | HN   | GLY | 33 | 90.734 | 67.991 | 59.869 | 1.00 | 0.00 |

FIG.24-G

| ATOM | 281 | CA | GLY | 33 | 89.816 | 66.794 | 58.384 | 1.00 | 0.00 |
|------|-----|------|------|----|--------|--------|--------|------|------|
| ATOM | 282 | HA1 | GLY | 33 | 89.891 | 67.483 | 57.555 | 1.00 | 0.00 |
| ATOM | 283 | HA2 | GLY | 33 | 88.859 | 66.295 | 58.339 | 1.00 | 0.00 |
| ATOM | 284 | C | GLY | 33 | 90.915 | 65.758 | 58.260 | 1.00 | 0.00 |
| ATOM | 285 | O | GLY | 33 | 92.070 | 66.027 | 58.590 | 1.00 | 0.00 |
| ATOM | 286 | N | LEU | 34 | 90.557 | 64.570 | 57.783 | 1.00 | 0.00 |
| ATOM | 287 | HN | LEU | 34 | 89.622 | 64.416 | 57.535 | 1.00 | 0.00 |
| ATOM | 288 | CA | LEU | 34 | 91.524 | 63.491 | 57.619 | 1.00 | 0.00 |
| ATOM | 289 | HA | LEU | 34 | 92.402 | 63.744 | 58.195 | 1.00 | 0.00 |
| ATOM | 290 | CB | LEU | 34 | 90.945 | 62.177 | 58.145 | 1.00 | 0.00 |
| ATOM | 291 | HB1 | LEU | 34 | 91.503 | 61.362 | 57.709 | 1.00 | 0.00 |
| ATOM | 292 | HB2 | LEU | 34 | 89.918 | 62.104 | 57.818 | 1.00 | 0.00 |
| ATOM | 293 | CG | LEU | 34 | 90.977 | 62.016 | 59.666 | 1.00 | 0.00 |
| ATOM | 294 | HG | LEU | 34 | 90.367 | 62.787 | 60.115 | 1.00 | 0.00 |
| ATOM | 295 | CD1 | LEU | 34 | 90.404 | 60.667 | 60.072 | 1.00 | 0.00 |
| ATOM | 296 | HD11 | LEU | 34 | 91.081 | 59.883 | 59.767 | 1.00 | 0.00 |
| ATOM | 297 | HD12 | LEU | 34 | 89.447 | 60.524 | 59.592 | 1.00 | 0.00 |
| ATOM | 298 | HD13 | LEU | 34 | 90.277 | 60.638 | 61.144 | 1.00 | 0.00 |
| ATOM | 299 | CD2 | LEU | 34 | 92.397 | 62.173 | 60.190 | 1.00 | 0.00 |
| ATOM | 300 | HD21 | LEU | 34 | 92.532 | 61.544 | 61.058 | 1.00 | 0.00 |
| ATOM | 301 | HD22 | LEU | 34 | 92.569 | 63.204 | 60.462 | 1.00 | 0.00 |
| ATOM | 302 | HD23 | LEU | 34 | 93.098 | 61.881 | 59.422 | 1.00 | 0.00 |
| ATOM | 303 | C | LEU | 34 | 91.925 | 63.334 | 56.156 | 1.00 | 0.00 |
| ATOM | 304 | O | LEU | 34 | 91.076 | 63.338 | 55.265 | 1.00 | 0.00 |
| ATOM | 305 | N | MET | 35 | 93.225 | 63.197 | 55.917 | 1.00 | 0.00 |
| ATOM | 306 | HN | MET | 35 | 93.853 | 63.202 | 56.669 | 1.00 | 0.00 |
| ATOM | 307 | CA | MET | 35 | 93.741 | 63.038 | 54.562 | 1.00 | 0.00 |
| ATOM | 308 | HA | MET | 35 | 92.906 | 62.825 | 53.912 | 1.00 | 0.00 |
| ATOM | 309 | CB | MET | 35 | 94.417 | 64.330 | 54.097 | 1.00 | 0.00 |
| ATOM | 310 | HB1 | MET | 35 | 93.661 | 65.088 | 53.958 | 1.00 | 0.00 |
| ATOM | 311 | HB2 | MET | 35 | 94.908 | 64.146 | 53.153 | 1.00 | 0.00 |
| ATOM | 312 | CG | MET | 35 | 95.451 | 64.861 | 55.076 | 1.00 | 0.00 |
| ATOM | 313 | HG1 | MET | 35 | 96.188 | 65.428 | 54.527 | 1.00 | 0.00 |
| ATOM | 314 | HG2 | MET | 35 | 95.931 | 64.025 | 55.561 | 1.00 | 0.00 |
| ATOM | 315 | SD | MET | 35 | 94.728 | 65.924 | 56.341 | 1.00 | 0.00 |
| ATOM | 316 | CE | MET | 35 | 96.175 | 66.312 | 57.324 | 1.00 | 0.00 |
| ATOM | 317 | HE1 | MET | 35 | 97.060 | 66.221 | 56.713 | 1.00 | 0.00 |
| ATOM | 318 | HE2 | MET | 35 | 96.239 | 65.626 | 58.156 | 1.00 | 0.00 |
| ATOM | 319 | HE3 | MET | 35 | 96.096 | 67.323 | 57.696 | 1.00 | 0.00 |
| ATOM | 320 | C | MET | 35 | 94.729 | 61.879 | 54.489 | 1.00 | 0.00 |

FIG.24-H

| ATOM | 321 | O | MET | 35 | 95.635 | 61.769 | 55.314 | 1.00 | 0.00 |
|---|---|---|---|---|---|---|---|---|---|
| ATOM | 322 | N | VAL | 36 | 94.548 | 61.015 | 53.495 | 1.00 | 0.00 |
| ATOM | 323 | HN | VAL | 36 | 93.807 | 61.156 | 52.868 | 1.00 | 0.00 |
| ATOM | 324 | CA | VAL | 36 | 95.423 | 59.864 | 53.314 | 1.00 | 0.00 |
| ATOM | 325 | HA | VAL | 36 | 96.192 | 59.908 | 54.071 | 1.00 | 0.00 |
| ATOM | 326 | CB | VAL | 36 | 94.653 | 58.541 | 53.484 | 1.00 | 0.00 |
| ATOM | 327 | HB | VAL | 36 | 93.790 | 58.727 | 54.106 | 1.00 | 0.00 |
| ATOM | 328 | CG1 | VAL | 36 | 94.165 | 58.030 | 52.137 | 1.00 | 0.00 |
| ATOM | 329 | HG11 | VAL | 36 | 95.010 | 57.709 | 51.546 | 1.00 | 0.00 |
| ATOM | 330 | HG12 | VAL | 36 | 93.643 | 58.821 | 51.619 | 1.00 | 0.00 |
| ATOM | 331 | HG13 | VAL | 36 | 93.495 | 57.196 | 52.289 | 1.00 | 0.00 |
| ATOM | 332 | CG2 | VAL | 36 | 95.523 | 57.502 | 54.174 | 1.00 | 0.00 |
| ATOM | 333 | HG21 | VAL | 36 | 95.013 | 56.550 | 54.177 | 1.00 | 0.00 |
| ATOM | 334 | HG22 | VAL | 36 | 95.715 | 57.811 | 55.191 | 1.00 | 0.00 |
| ATOM | 335 | HG23 | VAL | 36 | 96.459 | 57.406 | 53.644 | 1.00 | 0.00 |
| ATOM | 336 | C | VAL | 36 | 96.081 | 59.883 | 51.939 | 1.00 | 0.00 |
| ATOM | 337 | O | VAL | 36 | 95.605 | 60.551 | 51.021 | 1.00 | 0.00 |
| ATOM | 338 | N | GLY | 37 | 97.177 | 59.144 | 51.804 | 1.00 | 0.00 |
| ATOM | 339 | HN | GLY | 37 | 97.510 | 58.632 | 52.570 | 1.00 | 0.00 |
| ATOM | 340 | CA | GLY | 37 | 97.883 | 59.089 | 50.537 | 1.00 | 0.00 |
| ATOM | 341 | HA1 | GLY | 37 | 98.766 | 59.708 | 50.602 | 1.00 | 0.00 |
| ATOM | 342 | HA2 | GLY | 37 | 97.240 | 59.477 | 49.762 | 1.00 | 0.00 |
| ATOM | 343 | C | GLY | 37 | 98.301 | 57.679 | 50.167 | 1.00 | 0.00 |
| ATOM | 344 | O | GLY | 37 | 98.388 | 56.804 | 51.029 | 1.00 | 0.00 |
| ATOM | 345 | N | GLY | 38 | 98.560 | 57.458 | 48.883 | 1.00 | 0.00 |
| ATOM | 346 | HN | GLY | 38 | 98.474 | 58.194 | 48.241 | 1.00 | 0.00 |
| ATOM | 347 | CA | GLY | 38 | 98.967 | 56.143 | 48.424 | 1.00 | 0.00 |
| ATOM | 348 | HA1 | GLY | 38 | 98.130 | 55.671 | 47.931 | 1.00 | 0.00 |
| ATOM | 349 | HA2 | GLY | 38 | 99.249 | 55.547 | 49.280 | 1.00 | 0.00 |
| ATOM | 350 | C | GLY | 38 | 100.135 | 56.200 | 47.460 | 1.00 | 0.00 |
| ATOM | 351 | O | GLY | 38 | 100.293 | 57.173 | 46.722 | 1.00 | 0.00 |
| ATOM | 352 | N | VAL | 39 | 100.956 | 55.155 | 47.466 | 1.00 | 0.00 |
| ATOM | 353 | HN | VAL | 39 | 100.778 | 54.410 | 48.077 | 1.00 | 0.00 |
| ATOM | 354 | CA | VAL | 39 | 102.116 | 55.090 | 46.585 | 1.00 | 0.00 |
| ATOM | 355 | HA | VAL | 39 | 102.260 | 56.068 | 46.150 | 1.00 | 0.00 |
| ATOM | 356 | CB | VAL | 39 | 103.391 | 54.714 | 47.362 | 1.00 | 0.00 |
| ATOM | 357 | HB | VAL | 39 | 103.293 | 53.693 | 47.702 | 1.00 | 0.00 |
| ATOM | 358 | CG1 | VAL | 39 | 104.612 | 54.798 | 46.459 | 1.00 | 0.00 |
| ATOM | 359 | HG11 | VAL | 39 | 105.092 | 55.757 | 46.591 | 1.00 | 0.00 |
| ATOM | 360 | HG12 | VAL | 39 | 104.307 | 54.687 | 45.429 | 1.00 | 0.00 |

FIG. 24-I

| | | | | | | | | |
|---|---|---|---|---|---|---|---|---|
| ATOM | 361 | HG13 | VAL | 39 | 105.305 | 54.011 | 46.716 | 1.00 0.00 |
| ATOM | 362 | CG2 | VAL | 39 | 103.557 | 55.609 | 48.581 | 1.00 0.00 |
| ATOM | 363 | HG21 | VAL | 39 | 102.915 | 55.258 | 49.376 | 1.00 0.00 |
| ATOM | 364 | HG22 | VAL | 39 | 103.289 | 56.622 | 48.323 | 1.00 0.00 |
| ATOM | 365 | HG23 | VAL | 39 | 104.585 | 55.581 | 48.911 | 1.00 0.00 |
| ATOM | 366 | C | VAL | 39 | 101.900 | 54.077 | 45.466 | 1.00 0.00 |
| ATOM | 367 | O | VAL | 39 | 101.549 | 52.925 | 45.718 | 1.00 0.00 |
| ATOM | 368 | N | VAL | 40 | 102.111 | 54.515 | 44.230 | 1.00 0.00 |
| ATOM | 369 | HN | VAL | 40 | 102.389 | 55.445 | 44.093 | 1.00 0.00 |
| ATOM | 370 | CA | VAL | 40 | 101.939 | 53.647 | 43.071 | 1.00 0.00 |
| ATOM | 371 | HA | VAL | 40 | 101.904 | 52.626 | 43.423 | 1.00 0.00 |
| ATOM | 372 | CB | VAL | 40 | 100.623 | 53.951 | 42.332 | 1.00 0.00 |
| ATOM | 373 | HB | VAL | 40 | 100.843 | 54.067 | 41.280 | 1.00 0.00 |
| ATOM | 374 | CG1 | VAL | 40 | 99.644 | 52.798 | 42.487 | 1.00 0.00 |
| ATOM | 375 | HG11 | VAL | 40 | 98.711 | 53.050 | 42.006 | 1.00 0.00 |
| ATOM | 376 | HG12 | VAL | 40 | 99.469 | 52.613 | 43.537 | 1.00 0.00 |
| ATOM | 377 | HG13 | VAL | 40 | 100.056 | 51.911 | 42.029 | 1.00 0.00 |
| ATOM | 378 | CG2 | VAL | 40 | 100.014 | 55.249 | 42.837 | 1.00 0.00 |
| ATOM | 379 | HG21 | VAL | 40 | 99.922 | 55.947 | 42.018 | 1.00 0.00 |
| ATOM | 380 | HG22 | VAL | 40 | 100.650 | 55.672 | 43.601 | 1.00 0.00 |
| ATOM | 381 | HG23 | VAL | 40 | 99.037 | 55.051 | 43.252 | 1.00 0.00 |
| ATOM | 382 | C | VAL | 40 | 103.103 | 53.795 | 42.097 | 1.00 0.00 |
| ATOM | 383 | O | VAL | 40 | 103.697 | 54.867 | 41.982 | 1.00 0.00 |
| ATOM | 384 | N | ILE | 41 | 103.423 | 52.711 | 41.397 | 1.00 0.00 |
| ATOM | 385 | HN | ILE | 41 | 102.912 | 51.886 | 41.533 | 1.00 0.00 |
| ATOM | 386 | CA | ILE | 41 | 104.516 | 52.721 | 40.433 | 1.00 0.00 |
| ATOM | 387 | HA | ILE | 41 | 104.961 | 53.706 | 40.443 | 1.00 0.00 |
| ATOM | 388 | CB | ILE | 41 | 105.603 | 51.695 | 40.805 | 1.00 0.00 |
| ATOM | 389 | HB | ILE | 41 | 105.115 | 50.792 | 41.140 | 1.00 0.00 |
| ATOM | 390 | CG1 | ILE | 41 | 106.482 | 52.237 | 41.934 | 1.00 0.00 |
| ATOM | 391 | HG11 | ILE | 41 | 105.849 | 52.631 | 42.716 | 1.00 0.00 |
| ATOM | 392 | HG12 | ILE | 41 | 107.105 | 53.030 | 41.548 | 1.00 0.00 |
| ATOM | 393 | CG2 | ILE | 41 | 106.448 | 51.352 | 39.587 | 1.00 0.00 |
| ATOM | 394 | HG21 | ILE | 41 | 105.801 | 51.085 | 38.765 | 1.00 0.00 |
| ATOM | 395 | HG22 | ILE | 41 | 107.095 | 50.520 | 39.821 | 1.00 0.00 |
| ATOM | 396 | HG23 | ILE | 41 | 107.047 | 52.208 | 39.312 | 1.00 0.00 |
| ATOM | 397 | CD1 | ILE | 41 | 107.388 | 51.193 | 42.549 | 1.00 0.00 |
| ATOM | 398 | HD11 | ILE | 41 | 106.827 | 50.287 | 42.723 | 1.00 0.00 |
| ATOM | 399 | HD12 | ILE | 41 | 107.777 | 51.561 | 43.487 | 1.00 0.00 |
| ATOM | 400 | HD13 | ILE | 41 | 108.207 | 50.986 | 41.876 | 1.00 0.00 |

FIG.24-J

| | | | | | | | | |
|---|---|---|---|---|---|---|---|---|
| ATOM | 401 | C | ILE | 41 | 104.011 | 52.421 | 39.026 | 1.00 | 0.00 |
| ATOM | 402 | O | ILE | 41 | 104.397 | 53.083 | 38.062 | 1.00 | 0.00 |
| ATOM | 403 | N | ALA | 42 | 103.145 | 51.419 | 38.914 | 1.00 | 0.00 |
| ATOM | 404 | HN | ALA | 42 | 102.875 | 50.928 | 39.718 | 1.00 | 0.00 |
| ATOM | 405 | HA | ALA | 42 | 103.321 | 51.256 | 36.863 | 1.00 | 0.00 |
| ATOM | 406 | CB | ALA | 42 | 102.319 | 49.534 | 37.595 | 1.00 | 0.00 |
| ATOM | 407 | HB1 | ALA | 42 | 101.865 | 49.231 | 38.527 | 1.00 | 0.00 |
| ATOM | 408 | HB2 | ALA | 42 | 103.250 | 49.004 | 37.458 | 1.00 | 0.00 |
| ATOM | 409 | HB3 | ALA | 42 | 101.650 | 49.304 | 36.778 | 1.00 | 0.00 |
| ATOM | 410 | CA | ALA | 42 | 102.588 | 51.031 | 37.624 | 1.00 | 0.00 |
| ATOM | 411 | C | ALA | 42 | 101.310 | 51.806 | 37.323 | 1.00 | 0.00 |
| ATOM | 412 | OT1 | ALA | 42 | 101.245 | 53.001 | 37.682 | 1.00 | 0.00 |
| ATOM | 413 | OT2 | ALA | 42 | 100.384 | 51.212 | 36.731 | 1.00 | 0.00 |
| TER | 414 | | | | | | | | |
| ATOM | 415 | HA | GLN | 115 | 85.614 | 68.400 | 46.448 | 1.00 | 0.00 |
| ATOM | 416 | CB | GLN | 115 | 87.733 | 68.678 | 46.594 | 1.00 | 0.00 |
| ATOM | 417 | HB1 | GLN | 115 | 88.413 | 69.265 | 47.193 | 1.00 | 0.00 |
| ATOM | 418 | HB2 | GLN | 115 | 87.779 | 69.021 | 45.571 | 1.00 | 0.00 |
| ATOM | 419 | CG | GLN | 115 | 88.194 | 67.230 | 46.633 | 1.00 | 0.00 |
| ATOM | 420 | HG1 | GLN | 115 | 88.180 | 66.834 | 45.628 | 1.00 | 0.00 |
| ATOM | 421 | HG2 | GLN | 115 | 87.512 | 66.665 | 47.251 | 1.00 | 0.00 |
| ATOM | 422 | CD | GLN | 115 | 89.594 | 67.079 | 47.194 | 1.00 | 0.00 |
| ATOM | 423 | OE1 | GLN | 115 | 90.494 | 66.574 | 46.523 | 1.00 | 0.00 |
| ATOM | 424 | NE2 | GLN | 115 | 89.785 | 67.516 | 48.434 | 1.00 | 0.00 |
| ATOM | 425 | HE21 | GLN | 115 | 89.022 | 67.907 | 48.909 | 1.00 | 0.00 |
| ATOM | 426 | HE22 | GLN | 115 | 90.681 | 67.431 | 48.822 | 1.00 | 0.00 |
| ATOM | 427 | C | GLN | 115 | 86.174 | 68.250 | 48.500 | 1.00 | 0.00 |
| ATOM | 428 | O | GLN | 115 | 87.034 | 68.428 | 49.363 | 1.00 | 0.00 |
| ATOM | 429 | N | GLN | 115 | 85.985 | 70.331 | 47.165 | 1.00 | 0.00 |
| ATOM | 430 | HT1 | GLN | 115 | 85.522 | 70.565 | 48.067 | 1.00 | 0.00 |
| ATOM | 431 | HT2 | GLN | 115 | 85.343 | 70.578 | 46.385 | 1.00 | 0.00 |
| ATOM | 432 | HT3 | GLN | 115 | 86.854 | 70.895 | 47.076 | 1.00 | 0.00 |
| ATOM | 433 | CA | GLN | 115 | 86.310 | 68.882 | 47.119 | 1.00 | 0.00 |
| ATOM | 434 | N | LYS | 116 | 85.088 | 67.512 | 48.703 | 1.00 | 0.00 |
| ATOM | 435 | HN | LYS | 116 | 84.438 | 67.407 | 47.977 | 1.00 | 0.00 |
| ATOM | 436 | CA | LYS | 116 | 84.839 | 66.853 | 49.980 | 1.00 | 0.00 |
| ATOM | 437 | HA | LYS | 116 | 85.772 | 66.818 | 50.522 | 1.00 | 0.00 |
| ATOM | 438 | CB | LYS | 116 | 83.818 | 67.647 | 50.797 | 1.00 | 0.00 |
| ATOM | 439 | HB1 | LYS | 116 | 84.328 | 68.456 | 51.299 | 1.00 | 0.00 |
| ATOM | 440 | HB2 | LYS | 116 | 83.380 | 66.995 | 51.538 | 1.00 | 0.00 |

FIG.24-K

| ATOM | 441 | CG | LYS | 116 | 82.696 | 68.239 | 49.960 | 1.00 | 0.00 |
| --- | --- | --- | --- | --- | --- | --- | --- | --- | --- |
| ATOM | 442 | HG1 | LYS | 116 | 82.877 | 68.009 | 48.920 | 1.00 | 0.00 |
| ATOM | 443 | HG2 | LYS | 116 | 82.683 | 69.309 | 50.097 | 1.00 | 0.00 |
| ATOM | 444 | CD | LYS | 116 | 81.344 | 67.674 | 50.363 | 1.00 | 0.00 |
| ATOM | 445 | HD1 | LYS | 116 | 81.362 | 66.600 | 50.241 | 1.00 | 0.00 |
| ATOM | 446 | HD2 | LYS | 116 | 80.582 | 68.097 | 49.725 | 1.00 | 0.00 |
| ATOM | 447 | CE | LYS | 116 | 81.012 | 68.002 | 51.810 | 1.00 | 0.00 |
| ATOM | 448 | HE1 | LYS | 116 | 81.806 | 68.609 | 52.219 | 1.00 | 0.00 |
| ATOM | 449 | HE2 | LYS | 116 | 80.940 | 67.080 | 52.367 | 1.00 | 0.00 |
| ATOM | 450 | NZ | LYS | 116 | 79.725 | 68.741 | 51.930 | 1.00 | 0.00 |
| ATOM | 451 | HZ1 | LYS | 116 | 79.897 | 69.767 | 51.894 | 1.00 | 0.00 |
| ATOM | 452 | HZ2 | LYS | 116 | 79.263 | 68.511 | 52.833 | 1.00 | 0.00 |
| ATOM | 453 | HZ3 | LYS | 116 | 79.087 | 68.479 | 51.151 | 1.00 | 0.00 |
| ATOM | 454 | C | LYS | 116 | 84.340 | 65.427 | 49.769 | 1.00 | 0.00 |
| ATOM | 455 | O | LYS | 116 | 83.449 | 65.185 | 48.955 | 1.00 | 0.00 |
| ATOM | 456 | N | LEU | 117 | 84.920 | 64.487 | 50.508 | 1.00 | 0.00 |
| ATOM | 457 | HN | LEU | 117 | 85.624 | 64.743 | 51.140 | 1.00 | 0.00 |
| ATOM | 458 | CA | LEU | 117 | 84.534 | 63.085 | 50.402 | 1.00 | 0.00 |
| ATOM | 459 | HA | LEU | 117 | 83.633 | 63.033 | 49.809 | 1.00 | 0.00 |
| ATOM | 460 | CB | LEU | 117 | 85.635 | 62.283 | 49.707 | 1.00 | 0.00 |
| ATOM | 461 | HB1 | LEU | 117 | 86.023 | 61.560 | 50.408 | 1.00 | 0.00 |
| ATOM | 462 | HB2 | LEU | 117 | 86.431 | 62.962 | 49.438 | 1.00 | 0.00 |
| ATOM | 463 | CG | LEU | 117 | 85.195 | 61.536 | 48.446 | 1.00 | 0.00 |
| ATOM | 464 | HG | LEU | 117 | 86.068 | 61.157 | 47.936 | 1.00 | 0.00 |
| ATOM | 465 | CD1 | LEU | 117 | 84.312 | 60.352 | 48.809 | 1.00 | 0.00 |
| ATOM | 466 | HD11 | LEU | 117 | 83.999 | 59.847 | 47.907 | 1.00 | 0.00 |
| ATOM | 467 | HD12 | LEU | 117 | 83.443 | 60.702 | 49.346 | 1.00 | 0.00 |
| ATOM | 468 | HD13 | LEU | 117 | 84.868 | 59.666 | 49.431 | 1.00 | 0.00 |
| ATOM | 469 | CD2 | LEU | 117 | 84.466 | 62.477 | 47.499 | 1.00 | 0.00 |
| ATOM | 470 | HD21 | LEU | 117 | 83.401 | 62.320 | 47.584 | 1.00 | 0.00 |
| ATOM | 471 | HD22 | LEU | 117 | 84.779 | 62.279 | 46.484 | 1.00 | 0.00 |
| ATOM | 472 | HD23 | LEU | 117 | 84.700 | 63.499 | 47.755 | 1.00 | 0.00 |
| ATOM | 473 | C | LEU | 117 | 84.250 | 62.493 | 51.779 | 1.00 | 0.00 |
| ATOM | 474 | O | LEU | 117 | 85.157 | 62.331 | 52.595 | 1.00 | 0.00 |
| ATOM | 475 | N | VAL | 118 | 82.985 | 62.173 | 52.030 | 1.00 | 0.00 |
| ATOM | 476 | HN | VAL | 118 | 82.306 | 62.326 | 51.340 | 1.00 | 0.00 |
| ATOM | 477 | CA | VAL | 118 | 82.581 | 61.600 | 53.308 | 1.00 | 0.00 |
| ATOM | 478 | HA | VAL | 118 | 83.376 | 61.773 | 54.018 | 1.00 | 0.00 |
| ATOM | 479 | CB | VAL | 118 | 81.300 | 62.266 | 53.844 | 1.00 | 0.00 |
| ATOM | 480 | HB | VAL | 118 | 81.581 | 63.161 | 54.380 | 1.00 | 0.00 |

FIG.24-L

| | | | | | | | | |
|---|---|---|---|---|---|---|---|---|
| ATOM | 481 | CG1 | VAL | 118 | 80.386 | 62.667 | 52.696 | 1.00 0.00 |
| ATOM | 482 | HG11 | VAL | 118 | 79.396 | 62.867 | 53.078 | 1.00 0.00 |
| ATOM | 483 | HG12 | VAL | 118 | 80.339 | 61.864 | 51.976 | 1.00 0.00 |
| ATOM | 484 | HG13 | VAL | 118 | 80.774 | 63.556 | 52.220 | 1.00 0.00 |
| ATOM | 485 | CG2 | VAL | 118 | 80.579 | 61.338 | 54.810 | 1.00 0.00 |
| ATOM | 486 | HG21 | VAL | 118 | 79.915 | 60.690 | 54.258 | 1.00 0.00 |
| ATOM | 487 | HG22 | VAL | 118 | 80.007 | 61.925 | 55.514 | 1.00 0.00 |
| ATOM | 488 | HG23 | VAL | 118 | 81.304 | 60.741 | 55.344 | 1.00 0.00 |
| ATOM | 489 | C | VAL | 118 | 82.345 | 60.098 | 53.187 | 1.00 0.00 |
| ATOM | 490 | O | VAL | 118 | 81.532 | 59.651 | 52.379 | 1.00 0.00 |
| ATOM | 491 | N | PHE | 119 | 83.061 | 59.324 | 53.996 | 1.00 0.00 |
| ATOM | 492 | HN | PHE | 119 | 83.694 | 59.740 | 54.619 | 1.00 0.00 |
| ATOM | 493 | CA | PHE | 119 | 82.929 | 57.872 | 53.980 | 1.00 0.00 |
| ATOM | 494 | HA | PHE | 119 | 82.472 | 57.592 | 53.043 | 1.00 0.00 |
| ATOM | 495 | CB | PHE | 119 | 84.306 | 57.213 | 54.078 | 1.00 0.00 |
| ATOM | 496 | HB1 | PHE | 119 | 84.181 | 56.141 | 54.126 | 1.00 0.00 |
| ATOM | 497 | HB2 | PHE | 119 | 84.797 | 57.553 | 54.977 | 1.00 0.00 |
| ATOM | 498 | CG | PHE | 119 | 85.205 | 57.523 | 52.915 | 1.00 0.00 |
| ATOM | 499 | CD1 | PHE | 119 | 85.923 | 58.707 | 52.875 | 1.00 0.00 |
| ATOM | 500 | HD1 | PHE | 119 | 85.833 | 59.409 | 53.691 | 1.00 0.00 |
| ATOM | 501 | CD2 | PHE | 119 | 85.330 | 56.631 | 51.862 | 1.00 0.00 |
| ATOM | 502 | HD2 | PHE | 119 | 84.775 | 55.705 | 51.883 | 1.00 0.00 |
| ATOM | 503 | CE1 | PHE | 119 | 86.751 | 58.996 | 51.807 | 1.00 0.00 |
| ATOM | 504 | HE1 | PHE | 119 | 87.305 | 59.922 | 51.787 | 1.00 0.00 |
| ATOM | 505 | CE2 | PHE | 119 | 86.156 | 56.914 | 50.791 | 1.00 0.00 |
| ATOM | 506 | HE2 | PHE | 119 | 86.246 | 56.211 | 49.976 | 1.00 0.00 |
| ATOM | 507 | CZ | PHE | 119 | 86.867 | 58.098 | 50.763 | 1.00 0.00 |
| ATOM | 508 | HZ | PHE | 119 | 87.513 | 58.322 | 49.927 | 1.00 0.00 |
| ATOM | 509 | C | PHE | 119 | 82.040 | 57.394 | 55.123 | 1.00 0.00 |
| ATOM | 510 | O | PHE | 119 | 81.752 | 58.145 | 56.054 | 1.00 0.00 |
| ATOM | 511 | N | PHE | 120 | 81.609 | 56.139 | 55.046 | 1.00 0.00 |
| ATOM | 512 | HN | PHE | 120 | 81.872 | 55.589 | 54.278 | 1.00 0.00 |
| ATOM | 513 | CA | PHE | 120 | 80.752 | 55.561 | 56.074 | 1.00 0.00 |
| ATOM | 514 | HA | PHE | 120 | 80.305 | 56.373 | 56.628 | 1.00 0.00 |
| ATOM | 515 | CB | PHE | 120 | 79.642 | 54.726 | 55.434 | 1.00 0.00 |
| ATOM | 516 | HB1 | PHE | 120 | 80.088 | 53.915 | 54.877 | 1.00 0.00 |
| ATOM | 517 | HB2 | PHE | 120 | 79.075 | 55.350 | 54.759 | 1.00 0.00 |
| ATOM | 518 | CG | PHE | 120 | 78.685 | 54.134 | 56.429 | 1.00 0.00 |
| ATOM | 519 | CD1 | PHE | 120 | 78.789 | 52.805 | 56.805 | 1.00 0.00 |
| ATOM | 520 | HD1 | PHE | 120 | 79.569 | 52.192 | 56.377 | 1.00 0.00 |

FIG.24-M

| ATOM | 521 | CD2 | PHE | 120 | 77.680 | 54.908 | 56.988 | 1.00 | 0.00 |
| --- | --- | --- | --- | --- | --- | --- | --- | --- | --- |
| ATOM | 522 | HD2 | PHE | 120 | 77.590 | 55.946 | 56.702 | 1.00 | 0.00 |
| ATOM | 523 | CE1 | PHE | 120 | 77.910 | 52.258 | 57.721 | 1.00 | 0.00 |
| ATOM | 524 | HE1 | PHE | 120 | 78.002 | 51.221 | 58.006 | 1.00 | 0.00 |
| ATOM | 525 | CE2 | PHE | 120 | 76.798 | 54.367 | 57.904 | 1.00 | 0.00 |
| ATOM | 526 | HE2 | PHE | 120 | 76.020 | 54.981 | 58.332 | 1.00 | 0.00 |
| ATOM | 527 | CZ | PHE | 120 | 76.913 | 53.041 | 58.270 | 1.00 | 0.00 |
| ATOM | 528 | HZ | PHE | 120 | 76.225 | 52.616 | 58.986 | 1.00 | 0.00 |
| ATOM | 529 | C | PHE | 120 | 81.563 | 54.698 | 57.035 | 1.00 | 0.00 |
| ATOM | 530 | O | PHE | 120 | 82.107 | 53.664 | 56.649 | 1.00 | 0.00 |
| ATOM | 531 | N | ALA | 121 | 81.640 | 55.131 | 58.290 | 1.00 | 0.00 |
| ATOM | 532 | HN | ALA | 121 | 81.185 | 55.963 | 58.537 | 1.00 | 0.00 |
| ATOM | 533 | CA | ALA | 121 | 82.385 | 54.398 | 59.306 | 1.00 | 0.00 |
| ATOM | 534 | HA | ALA | 121 | 82.840 | 53.540 | 58.832 | 1.00 | 0.00 |
| ATOM | 535 | CB | ALA | 121 | 83.495 | 55.268 | 59.876 | 1.00 | 0.00 |
| ATOM | 536 | HB1 | ALA | 121 | 83.154 | 56.291 | 59.939 | 1.00 | 0.00 |
| ATOM | 537 | HB2 | ALA | 121 | 84.360 | 55.216 | 59.231 | 1.00 | 0.00 |
| ATOM | 538 | HB3 | ALA | 121 | 83.759 | 54.915 | 60.861 | 1.00 | 0.00 |
| ATOM | 539 | C | ALA | 121 | 81.463 | 53.916 | 60.421 | 1.00 | 0.00 |
| ATOM | 540 | O | ALA | 121 | 80.253 | 54.137 | 60.379 | 1.00 | 0.00 |
| ATOM | 541 | N | GLU | 122 | 82.044 | 53.255 | 61.417 | 1.00 | 0.00 |
| ATOM | 542 | HN | GLU | 122 | 83.013 | 53.111 | 61.395 | 1.00 | 0.00 |
| ATOM | 543 | CA | GLU | 122 | 81.274 | 52.741 | 62.544 | 1.00 | 0.00 |
| ATOM | 544 | HA | GLU | 122 | 80.255 | 53.078 | 62.430 | 1.00 | 0.00 |
| ATOM | 545 | CB | GLU | 122 | 81.294 | 51.211 | 62.546 | 1.00 | 0.00 |
| ATOM | 546 | HB1 | GLU | 122 | 82.263 | 50.876 | 62.888 | 1.00 | 0.00 |
| ATOM | 547 | HB2 | GLU | 122 | 81.137 | 50.859 | 61.538 | 1.00 | 0.00 |
| ATOM | 548 | CG | GLU | 122 | 80.233 | 50.590 | 63.439 | 1.00 | 0.00 |
| ATOM | 549 | HG1 | GLU | 122 | 79.500 | 50.099 | 62.816 | 1.00 | 0.00 |
| ATOM | 550 | HG2 | GLU | 122 | 79.754 | 51.374 | 64.007 | 1.00 | 0.00 |
| ATOM | 551 | CD | GLU | 122 | 80.807 | 49.573 | 64.406 | 1.00 | 0.00 |
| ATOM | 552 | OE1 | GLU | 122 | 80.572 | 48.363 | 64.204 | 1.00 | 0.00 |
| ATOM | 553 | OE2 | GLU | 122 | 81.491 | 49.987 | 65.366 | 1.00 | 0.00 |
| ATOM | 554 | C | GLU | 122 | 81.823 | 53.271 | 63.865 | 1.00 | 0.00 |
| ATOM | 555 | O | GLU | 122 | 83.032 | 53.438 | 64.024 | 1.00 | 0.00 |
| ATOM | 556 | N | ASP | 123 | 80.925 | 53.533 | 64.810 | 1.00 | 0.00 |
| ATOM | 557 | HN | ASP | 123 | 79.976 | 53.379 | 64.623 | 1.00 | 0.00 |
| ATOM | 558 | CA | ASP | 123 | 81.319 | 54.043 | 66.118 | 1.00 | 0.00 |
| ATOM | 559 | HA | ASP | 123 | 82.312 | 54.458 | 66.026 | 1.00 | 0.00 |
| ATOM | 560 | CB | ASP | 123 | 80.359 | 55.145 | 66.569 | 1.00 | 0.00 |

FIG.24-N

| | | | | | | | | |
|---|---|---|---|---|---|---|---|---|
| ATOM | 561 | HB1 | ASP | 123 | 79.790 | 54.793 | 67.417 | 1.00 0.00 |
| ATOM | 562 | HB2 | ASP | 123 | 79.684 | 55.379 | 65.759 | 1.00 0.00 |
| ATOM | 563 | CG | ASP | 123 | 81.084 | 56.415 | 66.970 | 1.00 0.00 |
| ATOM | 564 | OD1 | ASP | 123 | 82.294 | 56.338 | 67.271 | 1.00 0.00 |
| ATOM | 565 | OD2 | ASP | 123 | 80.441 | 57.486 | 66.984 | 1.00 0.00 |
| ATOM | 566 | C | ASP | 123 | 81.348 | 52.923 | 67.153 | 1.00 0.00 |
| ATOM | 567 | O | ASP | 123 | 80.666 | 51.909 | 67.004 | 1.00 0.00 |
| ATOM | 568 | N | VAL | 124 | 82.142 | 53.114 | 68.202 | 1.00 0.00 |
| ATOM | 569 | HN | VAL | 124 | 82.660 | 53.944 | 68.264 | 1.00 0.00 |
| ATOM | 570 | CA | VAL | 124 | 82.260 | 52.121 | 69.262 | 1.00 0.00 |
| ATOM | 571 | HA | VAL | 124 | 81.915 | 51.174 | 68.872 | 1.00 0.00 |
| ATOM | 572 | CB | VAL | 124 | 83.723 | 51.953 | 69.714 | 1.00 0.00 |
| ATOM | 573 | HB | VAL | 124 | 83.751 | 51.225 | 70.512 | 1.00 0.00 |
| ATOM | 574 | CG1 | VAL | 124 | 84.581 | 51.436 | 68.570 | 1.00 0.00 |
| ATOM | 575 | HG11 | VAL | 124 | 85.615 | 51.406 | 68.880 | 1.00 0.00 |
| ATOM | 576 | HG12 | VAL | 124 | 84.479 | 52.093 | 67.719 | 1.00 0.00 |
| ATOM | 577 | HG13 | VAL | 124 | 84.258 | 50.442 | 68.297 | 1.00 0.00 |
| ATOM | 578 | CG2 | VAL | 124 | 84.270 | 53.267 | 70.250 | 1.00 0.00 |
| ATOM | 579 | HG21 | VAL | 124 | 83.453 | 53.883 | 70.596 | 1.00 0.00 |
| ATOM | 580 | HG22 | VAL | 124 | 84.801 | 53.783 | 69.463 | 1.00 0.00 |
| ATOM | 581 | HG23 | VAL | 124 | 84.944 | 53.069 | 71.070 | 1.00 0.00 |
| ATOM | 582 | C | VAL | 124 | 81.408 | 52.500 | 70.468 | 1.00 0.00 |
| ATOM | 583 | O | VAL | 124 | 80.766 | 53.550 | 70.482 | 1.00 0.00 |
| ATOM | 584 | N | GLY | 125 | 81.407 | 51.637 | 71.480 | 1.00 0.00 |
| ATOM | 585 | HN | GLY | 125 | 81.938 | 50.817 | 71.412 | 1.00 0.00 |
| ATOM | 586 | CA | GLY | 125 | 80.630 | 51.900 | 72.676 | 1.00 0.00 |
| ATOM | 587 | HA1 | GLY | 125 | 80.549 | 52.968 | 72.814 | 1.00 0.00 |
| ATOM | 588 | HA2 | GLY | 125 | 81.144 | 51.476 | 73.526 | 1.00 0.00 |
| ATOM | 589 | C | GLY | 125 | 79.235 | 51.309 | 72.603 | 1.00 0.00 |
| ATOM | 590 | O | GLY | 125 | 78.622 | 51.019 | 73.630 | 1.00 0.00 |
| ATOM | 591 | N | SER | 126 | 78.735 | 51.130 | 71.385 | 1.00 0.00 |
| ATOM | 592 | HN | SER | 126 | 79.273 | 51.381 | 70.606 | 1.00 0.00 |
| ATOM | 593 | CA | SER | 126 | 77.404 | 50.570 | 71.180 | 1.00 0.00 |
| ATOM | 594 | HA | SER | 126 | 77.328 | 49.671 | 71.773 | 1.00 0.00 |
| ATOM | 595 | CB | SER | 126 | 76.334 | 51.562 | 71.639 | 1.00 0.00 |
| ATOM | 596 | HB1 | SER | 126 | 75.491 | 51.516 | 70.965 | 1.00 0.00 |
| ATOM | 597 | HB2 | SER | 126 | 76.745 | 52.560 | 71.634 | 1.00 0.00 |
| ATOM | 598 | OG | SER | 126 | 75.887 | 51.260 | 72.950 | 1.00 0.00 |
| ATOM | 599 | HG | SER | 126 | 76.604 | 50.862 | 73.449 | 1.00 0.00 |
| ATOM | 600 | C | SER | 126 | 77.185 | 50.211 | 69.714 | 1.00 0.00 |

FIG.24-O

| | | | | | | | | |
|---|---|---|---|---|---|---|---|---|
| ATOM | 601 | O | SER | 126 | 76.095 | 49.787 | 69.327 | 1.00 | 0.00 |
| ATOM | 602 | N | ASN | 127 | 78.232 | 50.387 | 68.907 | 1.00 | 0.00 |
| ATOM | 603 | HN | ASN | 127 | 79.069 | 50.729 | 69.285 | 1.00 | 0.00 |
| ATOM | 604 | CA | ASN | 127 | 78.173 | 50.086 | 67.478 | 1.00 | 0.00 |
| ATOM | 605 | HA | ASN | 127 | 79.126 | 50.354 | 67.047 | 1.00 | 0.00 |
| ATOM | 606 | CB | ASN | 127 | 77.932 | 48.591 | 67.253 | 1.00 | 0.00 |
| ATOM | 607 | HB1 | ASN | 127 | 77.541 | 48.442 | 66.258 | 1.00 | 0.00 |
| ATOM | 608 | HB2 | ASN | 127 | 77.212 | 48.237 | 67.975 | 1.00 | 0.00 |
| ATOM | 609 | CG | ASN | 127 | 79.200 | 47.773 | 67.400 | 1.00 | 0.00 |
| ATOM | 610 | OD1 | ASN | 127 | 79.901 | 47.868 | 68.407 | 1.00 | 0.00 |
| ATOM | 611 | ND2 | ASN | 127 | 79.501 | 46.963 | 66.392 | 1.00 | 0.00 |
| ATOM | 612 | HD21 | ASN | 127 | 78.897 | 46.939 | 65.621 | 1.00 | 0.00 |
| ATOM | 613 | HD22 | ASN | 127 | 80.316 | 46.422 | 66.461 | 1.00 | 0.00 |
| ATOM | 614 | C | ASN | 127 | 77.082 | 50.901 | 66.789 | 1.00 | 0.00 |
| ATOM | 615 | O | ASN | 127 | 75.916 | 50.508 | 66.774 | 1.00 | 0.00 |
| ATOM | 616 | N | LYS | 128 | 77.470 | 52.037 | 66.219 | 1.00 | 0.00 |
| ATOM | 617 | HN | LYS | 128 | 78.414 | 52.297 | 66.264 | 1.00 | 0.00 |
| ATOM | 618 | CA | LYS | 128 | 76.525 | 52.907 | 65.529 | 1.00 | 0.00 |
| ATOM | 619 | HA | LYS | 128 | 75.589 | 52.376 | 65.440 | 1.00 | 0.00 |
| ATOM | 620 | CB | LYS | 128 | 76.295 | 54.187 | 66.335 | 1.00 | 0.00 |
| ATOM | 621 | HB1 | LYS | 128 | 75.802 | 54.912 | 65.704 | 1.00 | 0.00 |
| ATOM | 622 | HB2 | LYS | 128 | 77.252 | 54.581 | 66.643 | 1.00 | 0.00 |
| ATOM | 623 | CG | LYS | 128 | 75.444 | 53.978 | 67.576 | 1.00 | 0.00 |
| ATOM | 624 | HG1 | LYS | 128 | 75.924 | 53.249 | 68.212 | 1.00 | 0.00 |
| ATOM | 625 | HG2 | LYS | 128 | 74.472 | 53.615 | 67.278 | 1.00 | 0.00 |
| ATOM | 626 | CD | LYS | 128 | 75.267 | 55.272 | 68.355 | 1.00 | 0.00 |
| ATOM | 627 | HD1 | LYS | 128 | 74.341 | 55.224 | 68.908 | 1.00 | 0.00 |
| ATOM | 628 | HD2 | LYS | 128 | 75.232 | 56.097 | 67.660 | 1.00 | 0.00 |
| ATOM | 629 | CE | LYS | 128 | 76.413 | 55.497 | 69.328 | 1.00 | 0.00 |
| ATOM | 630 | HE1 | LYS | 128 | 76.075 | 56.150 | 70.119 | 1.00 | 0.00 |
| ATOM | 631 | HE2 | LYS | 128 | 77.230 | 55.966 | 68.800 | 1.00 | 0.00 |
| ATOM | 632 | NZ | LYS | 128 | 76.893 | 54.220 | 69.925 | 1.00 | 0.00 |
| ATOM | 633 | HZ1 | LYS | 128 | 77.288 | 54.395 | 70.871 | 1.00 | 0.00 |
| ATOM | 634 | HZ2 | LYS | 128 | 77.632 | 53.800 | 69.326 | 1.00 | 0.00 |
| ATOM | 635 | HZ3 | LYS | 128 | 76.106 | 53.546 | 70.008 | 1.00 | 0.00 |
| ATOM | 636 | C | LYS | 128 | 77.026 | 53.256 | 64.131 | 1.00 | 0.00 |
| ATOM | 637 | O | LYS | 128 | 78.114 | 52.842 | 63.730 | 1.00 | 0.00 |
| ATOM | 638 | N | GLY | 129 | 76.226 | 54.019 | 63.394 | 1.00 | 0.00 |
| ATOM | 639 | HN | GLY | 129 | 75.371 | 54.319 | 63.766 | 1.00 | 0.00 |
| ATOM | 640 | CA | GLY | 129 | 76.606 | 54.409 | 62.049 | 1.00 | 0.00 |

FIG.24-P

| ATOM | 641 | HA1 | GLY | 129 | 75.738 | 54.349 | 61.410 | 1.00 | 0.00 |
|------|-----|------|-----|-----|--------|--------|--------|------|------|
| ATOM | 642 | HA2 | GLY | 129 | 77.356 | 53.723 | 61.685 | 1.00 | 0.00 |
| ATOM | 643 | C | GLY | 129 | 77.162 | 55.818 | 61.989 | 1.00 | 0.00 |
| ATOM | 644 | O | GLY | 129 | 76.410 | 56.784 | 61.857 | 1.00 | 0.00 |
| ATOM | 645 | N | ALA | 130 | 78.482 | 55.936 | 62.085 | 1.00 | 0.00 |
| ATOM | 646 | HN | ALA | 130 | 79.028 | 55.129 | 62.189 | 1.00 | 0.00 |
| ATOM | 647 | CA | ALA | 130 | 79.138 | 57.237 | 62.042 | 1.00 | 0.00 |
| ATOM | 648 | HA | ALA | 130 | 78.397 | 57.992 | 62.264 | 1.00 | 0.00 |
| ATOM | 649 | CB | ALA | 130 | 80.226 | 57.315 | 63.102 | 1.00 | 0.00 |
| ATOM | 650 | HB1 | ALA | 130 | 79.802 | 57.677 | 64.027 | 1.00 | 0.00 |
| ATOM | 651 | HB2 | ALA | 130 | 81.002 | 57.990 | 62.773 | 1.00 | 0.00 |
| ATOM | 652 | HB3 | ALA | 130 | 80.646 | 56.332 | 63.259 | 1.00 | 0.00 |
| ATOM | 653 | C | ALA | 130 | 79.722 | 57.511 | 60.660 | 1.00 | 0.00 |
| ATOM | 654 | O | ALA | 130 | 79.670 | 56.659 | 59.773 | 1.00 | 0.00 |
| ATOM | 655 | N | ILE | 131 | 80.279 | 58.705 | 60.484 | 1.00 | 0.00 |
| ATOM | 656 | HN | ILE | 131 | 80.289 | 59.342 | 61.229 | 1.00 | 0.00 |
| ATOM | 657 | CA | ILE | 131 | 80.873 | 59.091 | 59.210 | 1.00 | 0.00 |
| ATOM | 658 | HA | ILE | 131 | 81.042 | 58.192 | 58.635 | 1.00 | 0.00 |
| ATOM | 659 | CB | ILE | 131 | 79.933 | 60.010 | 58.407 | 1.00 | 0.00 |
| ATOM | 660 | HB | ILE | 131 | 80.536 | 60.737 | 57.885 | 1.00 | 0.00 |
| ATOM | 661 | CG1 | ILE | 131 | 78.973 | 60.740 | 59.348 | 1.00 | 0.00 |
| ATOM | 662 | HG11 | ILE | 131 | 78.651 | 60.060 | 60.123 | 1.00 | 0.00 |
| ATOM | 663 | HG12 | ILE | 131 | 78.112 | 61.074 | 58.787 | 1.00 | 0.00 |
| ATOM | 664 | CG2 | ILE | 131 | 79.161 | 59.206 | 57.372 | 1.00 | 0.00 |
| ATOM | 665 | HG21 | ILE | 131 | 78.505 | 59.864 | 56.821 | 1.00 | 0.00 |
| ATOM | 666 | HG22 | ILE | 131 | 78.576 | 58.447 | 57.869 | 1.00 | 0.00 |
| ATOM | 667 | HG23 | ILE | 131 | 79.855 | 58.737 | 56.690 | 1.00 | 0.00 |
| ATOM | 668 | CD1 | ILE | 131 | 79.587 | 61.951 | 60.018 | 1.00 | 0.00 |
| ATOM | 669 | HD11 | ILE | 131 | 80.442 | 61.644 | 60.602 | 1.00 | 0.00 |
| ATOM | 670 | HD12 | ILE | 131 | 78.856 | 62.413 | 60.665 | 1.00 | 0.00 |
| ATOM | 671 | HD13 | ILE | 131 | 79.900 | 62.658 | 59.264 | 1.00 | 0.00 |
| ATOM | 672 | C | ILE | 131 | 82.205 | 59.803 | 59.418 | 1.00 | 0.00 |
| ATOM | 673 | O | ILE | 131 | 82.381 | 60.540 | 60.389 | 1.00 | 0.00 |
| ATOM | 674 | N | ILE | 132 | 83.140 | 59.579 | 58.500 | 1.00 | 0.00 |
| ATOM | 675 | HN | ILE | 132 | 82.940 | 58.982 | 57.749 | 1.00 | 0.00 |
| ATOM | 676 | CA | ILE | 132 | 84.457 | 60.200 | 58.583 | 1.00 | 0.00 |
| ATOM | 677 | HA | ILE | 132 | 84.399 | 61.010 | 59.296 | 1.00 | 0.00 |
| ATOM | 678 | CB | ILE | 132 | 85.522 | 59.199 | 59.071 | 1.00 | 0.00 |
| ATOM | 679 | HB | ILE | 132 | 86.492 | 59.659 | 58.961 | 1.00 | 0.00 |
| ATOM | 680 | CG1 | ILE | 132 | 85.474 | 57.922 | 58.232 | 1.00 | 0.00 |

FIG.24-Q

| ATOM | 681 | HG11 | ILE | 132 | 85.575 | 58.181 | 57.188 | 1.00 | 0.00 |
| --- | --- | --- | --- | --- | --- | --- | --- | --- | --- |
| ATOM | 682 | HG12 | ILE | 132 | 84.525 | 57.432 | 58.386 | 1.00 | 0.00 |
| ATOM | 683 | CG2 | ILE | 132 | 85.316 | 58.880 | 60.545 | 1.00 | 0.00 |
| ATOM | 684 | HG21 | ILE | 132 | 85.224 | 59.799 | 61.104 | 1.00 | 0.00 |
| ATOM | 685 | HG22 | ILE | 132 | 86.161 | 58.318 | 60.913 | 1.00 | 0.00 |
| ATOM | 686 | HG23 | ILE | 132 | 84.415 | 58.295 | 60.664 | 1.00 | 0.00 |
| ATOM | 687 | CD1 | ILE | 132 | 86.567 | 56.932 | 58.574 | 1.00 | 0.00 |
| ATOM | 688 | HD11 | ILE | 132 | 87.510 | 57.451 | 58.657 | 1.00 | 0.00 |
| ATOM | 689 | HD12 | ILE | 132 | 86.634 | 56.187 | 57.795 | 1.00 | 0.00 |
| ATOM | 690 | HD13 | ILE | 132 | 86.336 | 56.451 | 59.513 | 1.00 | 0.00 |
| ATOM | 691 | C | ILE | 132 | 84.884 | 60.761 | 57.231 | 1.00 | 0.00 |
| ATOM | 692 | O | ILE | 132 | 84.592 | 60.180 | 56.186 | 1.00 | 0.00 |
| ATOM | 693 | N | GLY | 133 | 85.579 | 61.894 | 57.259 | 1.00 | 0.00 |
| ATOM | 694 | HN | GLY | 133 | 85.783 | 62.312 | 58.121 | 1.00 | 0.00 |
| ATOM | 695 | CA | GLY | 133 | 86.035 | 62.514 | 56.029 | 1.00 | 0.00 |
| ATOM | 696 | HA1 | GLY | 133 | 85.892 | 63.582 | 56.103 | 1.00 | 0.00 |
| ATOM | 697 | HA2 | GLY | 133 | 85.442 | 62.138 | 55.208 | 1.00 | 0.00 |
| ATOM | 698 | C | GLY | 133 | 87.498 | 62.235 | 55.744 | 1.00 | 0.00 |
| ATOM | 699 | O | GLY | 133 | 88.373 | 62.629 | 56.515 | 1.00 | 0.00 |
| ATOM | 700 | N | LEU | 134 | 87.762 | 61.555 | 54.633 | 1.00 | 0.00 |
| ATOM | 701 | HN | LEU | 134 | 87.021 | 61.269 | 54.059 | 1.00 | 0.00 |
| ATOM | 702 | CA | LEU | 134 | 89.129 | 61.222 | 54.247 | 1.00 | 0.00 |
| ATOM | 703 | HA | LEU | 134 | 89.797 | 61.691 | 54.954 | 1.00 | 0.00 |
| ATOM | 704 | CB | LEU | 134 | 89.339 | 59.707 | 54.294 | 1.00 | 0.00 |
| ATOM | 705 | HB1 | LEU | 134 | 90.372 | 59.500 | 54.060 | 1.00 | 0.00 |
| ATOM | 706 | HB2 | LEU | 134 | 88.718 | 59.256 | 53.534 | 1.00 | 0.00 |
| ATOM | 707 | CG | LEU | 134 | 89.012 | 59.049 | 55.636 | 1.00 | 0.00 |
| ATOM | 708 | HG | LEU | 134 | 88.430 | 59.736 | 56.234 | 1.00 | 0.00 |
| ATOM | 709 | CD1 | LEU | 134 | 88.183 | 57.791 | 55.425 | 1.00 | 0.00 |
| ATOM | 710 | HD11 | LEU | 134 | 88.630 | 57.192 | 54.645 | 1.00 | 0.00 |
| ATOM | 711 | HD12 | LEU | 134 | 87.179 | 58.066 | 55.138 | 1.00 | 0.00 |
| ATOM | 712 | HD13 | LEU | 134 | 88.153 | 57.223 | 56.343 | 1.00 | 0.00 |
| ATOM | 713 | CD2 | LEU | 134 | 90.290 | 58.726 | 56.396 | 1.00 | 0.00 |
| ATOM | 714 | HD21 | LEU | 134 | 90.745 | 57.842 | 55.975 | 1.00 | 0.00 |
| ATOM | 715 | HD22 | LEU | 134 | 90.055 | 58.550 | 57.436 | 1.00 | 0.00 |
| ATOM | 716 | HD23 | LEU | 134 | 90.975 | 59.557 | 56.317 | 1.00 | 0.00 |
| ATOM | 717 | C | LEU | 134 | 89.443 | 61.746 | 52.850 | 1.00 | 0.00 |
| ATOM | 718 | O | LEU | 134 | 88.555 | 61.863 | 52.005 | 1.00 | 0.00 |
| ATOM | 719 | N | MET | 135 | 90.713 | 62.061 | 52.613 | 1.00 | 0.00 |
| ATOM | 720 | HN | MET | 135 | 91.375 | 61.948 | 53.327 | 1.00 | 0.00 |

FIG.24-R

| | | | | | | | | |
|---|---|---|---|---|---|---|---|---|
| ATOM | 721 | CA | MET | 135 | 91.145 | 62.572 | 51.318 | 1.00 0.00 |
| ATOM | 722 | HA | MET | 135 | 90.272 | 62.937 | 50.797 | 1.00 0.00 |
| ATOM | 723 | CB | MET | 135 | 92.131 | 63.727 | 51.504 | 1.00 0.00 |
| ATOM | 724 | HB1 | MET | 135 | 93.125 | 63.320 | 51.623 | 1.00 0.00 |
| ATOM | 725 | HB2 | MET | 135 | 91.865 | 64.272 | 52.397 | 1.00 0.00 |
| ATOM | 726 | CG | MET | 135 | 92.152 | 64.703 | 50.339 | 1.00 0.00 |
| ATOM | 727 | HG1 | MET | 135 | 91.363 | 65.427 | 50.480 | 1.00 0.00 |
| ATOM | 728 | HG2 | MET | 135 | 91.978 | 64.156 | 49.425 | 1.00 0.00 |
| ATOM | 729 | SD | MET | 135 | 93.721 | 65.580 | 50.196 | 1.00 0.00 |
| ATOM | 730 | CE | MET | 135 | 93.442 | 66.534 | 48.707 | 1.00 0.00 |
| ATOM | 731 | HE1 | MET | 135 | 94.361 | 67.019 | 48.412 | 1.00 0.00 |
| ATOM | 732 | HE2 | MET | 135 | 92.684 | 67.280 | 48.894 | 1.00 0.00 |
| ATOM | 733 | HE3 | MET | 135 | 93.112 | 65.877 | 47.915 | 1.00 0.00 |
| ATOM | 734 | C | MET | 135 | 91.788 | 61.468 | 50.485 | 1.00 0.00 |
| ATOM | 735 | O | MET | 135 | 92.421 | 60.560 | 51.023 | 1.00 0.00 |
| ATOM | 736 | N | VAL | 136 | 91.622 | 61.553 | 49.169 | 1.00 0.00 |
| ATOM | 737 | HN | VAL | 136 | 91.108 | 62.301 | 48.799 | 1.00 0.00 |
| ATOM | 738 | CA | VAL | 136 | 92.187 | 60.562 | 48.262 | 1.00 0.00 |
| ATOM | 739 | HA | VAL | 136 | 92.562 | 59.741 | 48.857 | 1.00 0.00 |
| ATOM | 740 | CB | VAL | 136 | 91.121 | 60.011 | 47.296 | 1.00 0.00 |
| ATOM | 741 | HB | VAL | 136 | 90.772 | 60.824 | 46.676 | 1.00 0.00 |
| ATOM | 742 | CG1 | VAL | 136 | 91.720 | 58.946 | 46.390 | 1.00 0.00 |
| ATOM | 743 | HG11 | VAL | 136 | 92.594 | 59.344 | 45.896 | 1.00 0.00 |
| ATOM | 744 | HG12 | VAL | 136 | 90.991 | 58.653 | 45.649 | 1.00 0.00 |
| ATOM | 745 | HG13 | VAL | 136 | 92.000 | 58.086 | 46.980 | 1.00 0.00 |
| ATOM | 746 | CG2 | VAL | 136 | 89.935 | 59.457 | 48.070 | 1.00 0.00 |
| ATOM | 747 | HG21 | VAL | 136 | 89.028 | 59.935 | 47.730 | 1.00 0.00 |
| ATOM | 748 | HG22 | VAL | 136 | 90.070 | 59.651 | 49.124 | 1.00 0.00 |
| ATOM | 749 | HG23 | VAL | 136 | 89.864 | 58.392 | 47.907 | 1.00 0.00 |
| ATOM | 750 | C | VAL | 136 | 93.336 | 61.150 | 47.450 | 1.00 0.00 |
| ATOM | 751 | O | VAL | 136 | 93.128 | 61.694 | 46.365 | 1.00 0.00 |
| ATOM | 752 | N | GLY | 137 | 94.548 | 61.037 | 47.982 | 1.00 0.00 |
| ATOM | 753 | HN | GLY | 137 | 94.654 | 60.593 | 48.850 | 1.00 0.00 |
| ATOM | 754 | CA | GLY | 137 | 95.712 | 61.562 | 47.293 | 1.00 0.00 |
| ATOM | 755 | HA1 | GLY | 137 | 96.246 | 62.220 | 47.962 | 1.00 0.00 |
| ATOM | 756 | HA2 | GLY | 137 | 95.384 | 62.127 | 46.434 | 1.00 0.00 |
| ATOM | 757 | C | GLY | 137 | 96.654 | 60.468 | 46.828 | 1.00 0.00 |
| ATOM | 758 | O | GLY | 137 | 97.197 | 59.720 | 47.641 | 1.00 0.00 |
| ATOM | 759 | N | GLY | 138 | 96.847 | 60.374 | 45.517 | 1.00 0.00 |
| ATOM | 760 | HN | GLY | 138 | 96.387 | 60.998 | 44.917 | 1.00 0.00 |

FIG.24-S

| ATOM | 761 | CA | GLY | 138 | 97.729 | 59.361 | 44.968 | 1.00 | 0.00 |
| ATOM | 762 | HA1 | GLY | 138 | 97.169 | 58.745 | 44.281 | 1.00 | 0.00 |
| ATOM | 763 | HA2 | GLY | 138 | 98.095 | 58.743 | 45.774 | 1.00 | 0.00 |
| ATOM | 764 | C | GLY | 138 | 98.913 | 59.959 | 44.234 | 1.00 | 0.00 |
| ATOM | 765 | O | GLY | 138 | 98.799 | 61.017 | 43.615 | 1.00 | 0.00 |
| ATOM | 766 | N | VAL | 139 | 100.054 | 59.281 | 44.304 | 1.00 | 0.00 |
| ATOM | 767 | HN | VAL | 139 | 100.082 | 58.444 | 44.813 | 1.00 | 0.00 |
| ATOM | 768 | CA | VAL | 139 | 101.264 | 59.751 | 43.641 | 1.00 | 0.00 |
| ATOM | 769 | HA | VAL | 139 | 100.982 | 60.519 | 42.935 | 1.00 | 0.00 |
| ATOM | 770 | CB | VAL | 139 | 102.256 | 60.362 | 44.649 | 1.00 | 0.00 |
| ATOM | 771 | HB | VAL | 139 | 102.273 | 59.737 | 45.530 | 1.00 | 0.00 |
| ATOM | 772 | CG1 | VAL | 139 | 103.659 | 60.398 | 44.064 | 1.00 | 0.00 |
| ATOM | 773 | HG11 | VAL | 139 | 104.093 | 59.410 | 44.110 | 1.00 | 0.00 |
| ATOM | 774 | HG12 | VAL | 139 | 104.268 | 61.085 | 44.632 | 1.00 | 0.00 |
| ATOM | 775 | HG13 | VAL | 139 | 103.612 | 60.723 | 43.035 | 1.00 | 0.00 |
| ATOM | 776 | CG2 | VAL | 139 | 101.807 | 61.755 | 45.062 | 1.00 | 0.00 |
| ATOM | 777 | HG21 | VAL | 139 | 102.120 | 62.471 | 44.317 | 1.00 | 0.00 |
| ATOM | 778 | HG22 | VAL | 139 | 102.250 | 62.009 | 46.014 | 1.00 | 0.00 |
| ATOM | 779 | HG23 | VAL | 139 | 100.730 | 61.776 | 45.150 | 1.00 | 0.00 |
| ATOM | 780 | C | VAL | 139 | 101.955 | 58.618 | 42.891 | 1.00 | 0.00 |
| ATOM | 781 | O | VAL | 139 | 102.228 | 57.560 | 43.458 | 1.00 | 0.00 |
| ATOM | 782 | N | VAL | 140 | 102.235 | 58.847 | 41.612 | 1.00 | 0.00 |
| ATOM | 783 | HN | VAL | 140 | 101.993 | 59.710 | 41.216 | 1.00 | 0.00 |
| ATOM | 784 | CA | VAL | 140 | 102.895 | 57.844 | 40.784 | 1.00 | 0.00 |
| ATOM | 785 | HA | VAL | 140 | 102.953 | 56.928 | 41.353 | 1.00 | 0.00 |
| ATOM | 786 | CB | VAL | 140 | 102.097 | 57.565 | 39.496 | 1.00 | 0.00 |
| ATOM | 787 | HB | VAL | 140 | 101.235 | 56.966 | 39.754 | 1.00 | 0.00 |
| ATOM | 788 | CG1 | VAL | 140 | 101.603 | 58.864 | 38.879 | 1.00 | 0.00 |
| ATOM | 789 | HG11 | VAL | 140 | 102.438 | 59.534 | 38.736 | 1.00 | 0.00 |
| ATOM | 790 | HG12 | VAL | 140 | 100.880 | 59.324 | 39.537 | 1.00 | 0.00 |
| ATOM | 791 | HG13 | VAL | 140 | 101.141 | 58.657 | 37.925 | 1.00 | 0.00 |
| ATOM | 792 | CG2 | VAL | 140 | 102.942 | 56.781 | 38.504 | 1.00 | 0.00 |
| ATOM | 793 | HG21 | VAL | 140 | 103.172 | 55.809 | 38.915 | 1.00 | 0.00 |
| ATOM | 794 | HG22 | VAL | 140 | 103.860 | 57.317 | 38.311 | 1.00 | 0.00 |
| ATOM | 795 | HG23 | VAL | 140 | 102.394 | 56.661 | 37.581 | 1.00 | 0.00 |
| ATOM | 796 | C | VAL | 140 | 104.306 | 58.284 | 40.409 | 1.00 | 0.00 |
| ATOM | 797 | O | VAL | 140 | 104.500 | 59.336 | 39.801 | 1.00 | 0.00 |
| ATOM | 798 | N | ILE | 141 | 105.291 | 57.470 | 40.778 | 1.00 | 0.00 |
| ATOM | 799 | HN | ILE | 141 | 105.074 | 56.646 | 41.262 | 1.00 | 0.00 |
| ATOM | 800 | CA | ILE | 141 | 106.685 | 57.774 | 40.481 | 1.00 | 0.00 |

FIG.24-T

```
ATOM    801  HA    ILE   141     106.718  58.728  39.974  1.00  0.00
ATOM    802  CB    ILE   141     107.524  57.882  41.769  1.00  0.00
ATOM    803  HB    ILE   141     108.432  57.315  41.629  1.00  0.00
ATOM    804  CG1   ILE   141     106.752  57.305  42.957  1.00  0.00
ATOM    805  HG11  ILE   141     106.399  56.316  42.702  1.00  0.00
ATOM    806  HG12  ILE   141     105.906  57.940  43.171  1.00  0.00
ATOM    807  CG2   ILE   141     107.908  59.330  42.032  1.00  0.00
ATOM    808  HG21  ILE   141     107.024  59.949  41.997  1.00  0.00
ATOM    809  HG22  ILE   141     108.608  59.660  41.279  1.00  0.00
ATOM    810  HG23  ILE   141     108.364  59.410  43.008  1.00  0.00
ATOM    811  CD1   ILE   141     107.579  57.194  44.219  1.00  0.00
ATOM    812  HD11  ILE   141     108.625  57.118  43.959  1.00  0.00
ATOM    813  HD12  ILE   141     107.280  56.314  44.769  1.00  0.00
ATOM    814  HD13  ILE   141     107.423  58.071  44.830  1.00  0.00
ATOM    815  C     ILE   141     107.298  56.711  39.576  1.00  0.00
ATOM    816  O     ILE   141     106.888  55.550  39.606  1.00  0.00
ATOM    817  N     ALA   142     108.281  57.122  38.775  1.00  0.00
ATOM    818  HN    ALA   142     108.556  58.062  38.805  1.00  0.00
ATOM    819  HA    ALA   142     109.685  56.795  37.297  1.00  0.00
ATOM    820  CB    ALA   142     109.715  55.140  38.623  1.00  0.00
ATOM    821  HB1   ALA   142     109.709  55.379  39.676  1.00  0.00
ATOM    822  HB2   ALA   142     110.735  55.092  38.271  1.00  0.00
ATOM    823  HB3   ALA   142     109.236  54.184  38.468  1.00  0.00
ATOM    824  CA    ALA   142     108.962  56.216  37.854  1.00  0.00
ATOM    825  C     ALA   142     107.982  55.582  36.872  1.00  0.00
ATOM    826  OT1   ALA   142     107.075  56.297  36.397  1.00  0.00
ATOM    827  OT2   ALA   142     108.131  54.375  36.585  1.00  0.00
TER     828
END
```

FIG.24-U

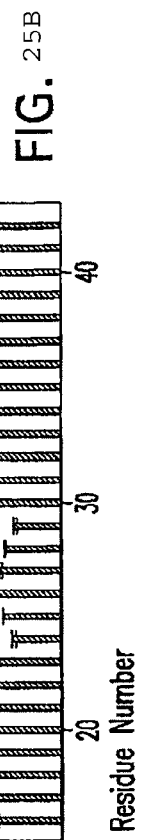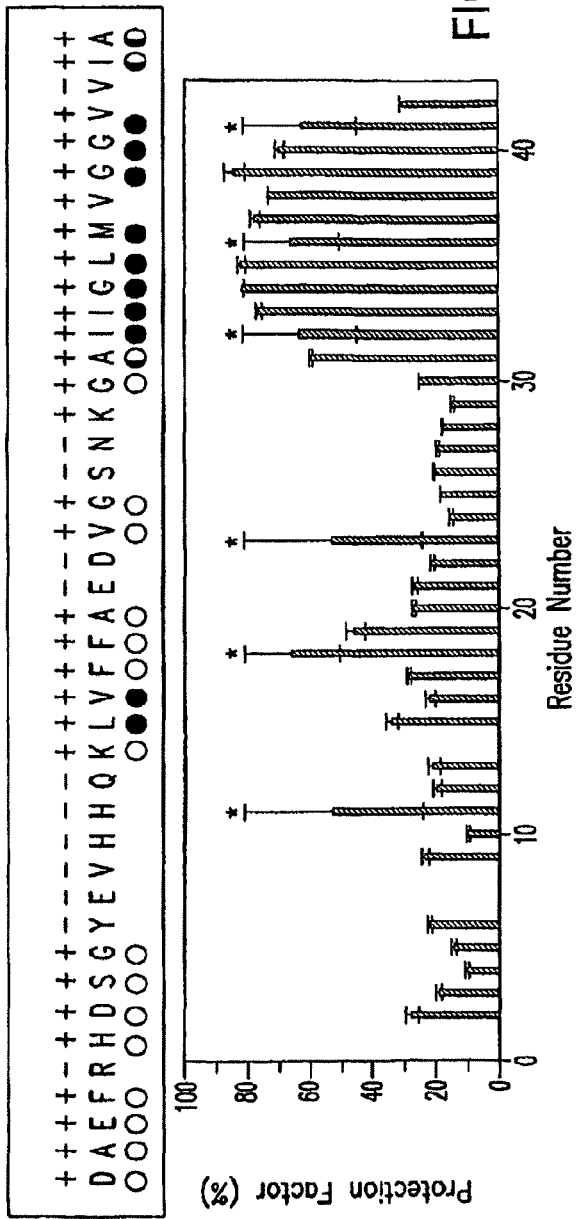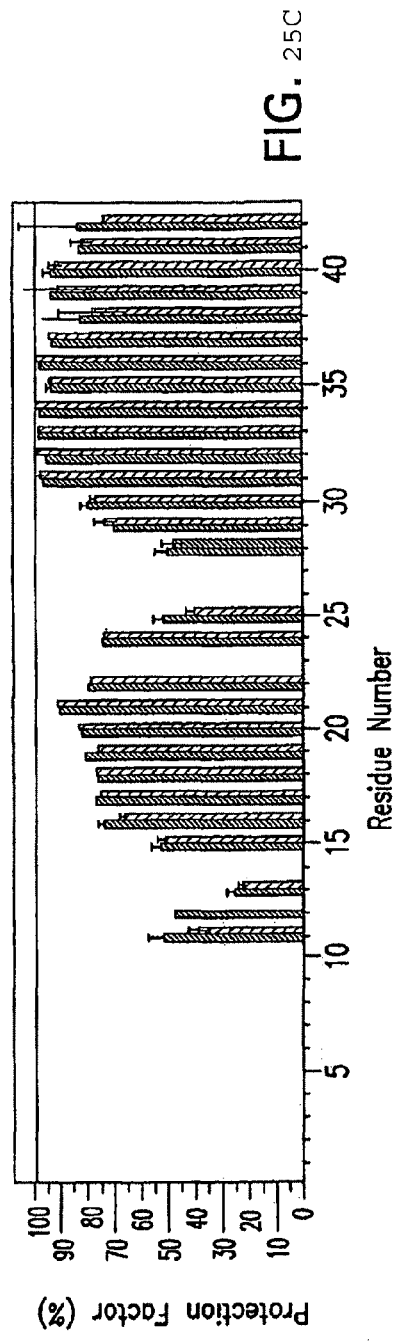
FIG. 25A
FIG. 25B
FIG. 25C

SEQUENCE LISTING

```
<160> NUMBER OF SEQ ID NOS: 29

<210> SEQ ID NO 1
<211> LENGTH: 141
<212> TYPE: DNA
<213> ORGANISM: Homo sapiens

<400> SEQUENCE: 1
catatggatg cggaatttcg ccatgatagc ggctatgaag tgcatcatca gaaactggtg      60
tttttcgcgg aagatgtggg cagcaacaaa ggcgcgatta ttggcctgat ggtgggtggt    120
gtggtgattg cgtgactcga g                                              141

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 40
<212> TYPE: PRT
<213> ORGANISM: Homo sapiens

<400> SEQUENCE: 3

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30
```

Ile Gly Leu Met Val Gly Gly Val
        35              40

<210> SEQ ID NO 4
<211> LENGTH: 41
<212> TYPE: PRT
<213> ORGANISM: Homo sapiens

<400> SEQUENCE: 4

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val
        35              40

<210> SEQ ID NO 5
<211> LENGTH: 42
<212> TYPE: PRT
<213> ORGANISM: Homo sapiens

<400> SEQUENCE: 5

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile
        35              40

<210> SEQ ID NO 6
<211> LENGTH: 43
<212> TYPE: PRT
<213> ORGANISM: Homo sapiens

<400> SEQUENCE: 6

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala
        35              40

<210> SEQ ID NO 7
<211> LENGTH: 44
<212> TYPE: PRT
<213> ORGANISM: Homo sapiens

<400> SEQUENCE: 7

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr
        35              40

<210> SEQ ID NO 8
<211> LENGTH: 43
<212> TYPE: PRT
<213> ORGANISM: Homo sapiens

<400> SEQUENCE: 8

-continued

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala
        35                  40

<210> SEQ ID NO 9
<211> LENGTH: 12
<212> TYPE: PRT
<213> ORGANISM: Homo sapiens

<400> SEQUENCE: 9

Lys Gly Ala Ile Ile Gly Leu Met Val Gly Gly Val
1               5                   10

<210> SEQ ID NO 10
<211> LENGTH: 7
<212> TYPE: PRT
<213> ORGANISM: Homo sapiens

<400> SEQUENCE: 10

Leu Val Phe Phe Ala Glu Asp
1               5

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatggatgcg gaatttcgcc atgatagcgg ctatgaag                          38

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcatcatca gaaactggtg tttttcgcgg aagatgtggg cagcaacaaa              50

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgcgatta ttggcctgat ggtgggtggt gtggtgattg cgtgac                  46

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
caccagtttc tgatgatgca cttcatagcc gctatcatgg cgaaattccg catcca         56
```

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
atcaggccaa taatcgcgcc tttgttgctg cccacatctt ccgcgaaaaa               50
```

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
tcgagtcacg caatcaccac accacccacc                                      30
```

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
gggtggtgtg gtgattgcga cctgactcga gcaccaccac c                         41
```

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
ggtggtggtg ctcgagtcag gtcgcaatca ccacaccacc c                         41
```

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
ggtgggtggt gtggtgattt gactcgagca ccaccacc                             38
```

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ggtggtggtg ctcgagtcaa atcaccacac cacccacc                             38
```

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gatggtgggt ggtgtggtgt gactcgagca ccaccacc        38

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggtggtggtg ctcgagtcac accacaccac ccaccatc        38

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
cctgatggtg ggtggtgtgt gactcgagca ccacc           35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggtggtgctc gagtcacaca ccacccacca tcagg           35

<210> SEQ ID NO 25
<211> LENGTH: 7
<212> TYPE: PRT
<213> ORGANISM: Homo sapiens

<400> SEQUENCE: 25

Glu Asp Val Gly Ser Asn Lys
1               5

<210> SEQ ID NO 26
<211> LENGTH: 40
<212> TYPE: PRT
<213> ORGANISM: Homo sapiens

<400> SEQUENCE: 26

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

```
<210> SEQ ID NO 27
<211> LENGTH: 23
<212> TYPE: PRT
<213> ORGANISM: Homo sapiens

<400> SEQUENCE: 27

Phe Ala Glu Asp Val Gly Ser Asn Lys Gly Ala Ile Ile Gly Leu Met
1               5                   10                  15

Val Gly Gly Val Val Ile Ala
            20

<210> SEQ ID NO 28
<211> LENGTH: 22
<212> TYPE: PRT
<213> ORGANISM: Homo sapiens

<400> SEQUENCE: 28

Val Phe Phe Ala Glu Asp Val Gly Ser Asn Lys Gly Ala Ile Ile Gly
1               5                   10                  15

Leu Met Val Gly Gly Val
            20

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Lys Leu Val Phe Phe Ala Glu Asp Val Gly Ser Asn Lys Gly Ala
1               5                   10                  15

Ile Ile Gly Leu Met Val Gly Gly Val Val Ile Ala
            20                  25
```

METHODS OF PREPARATION OF RECOMBINANT FORMS OF HUMAN BETA-AMYLOID PROTEIN AND USES OF THESE PROTEINS

BACKGROUND OF THE INVENTION

1. Technical Field

The subject invention relates to the cloning, expression and isolation of recombinant forms of amyloid beta protein containing a N-terminal methionine (and/or one or more other amino acid residues) as well as to methods of using these recombinant proteins.

2. Background Information

Amyloid β(1-42) protein, also referred to as Aβ(1-42), is a family of proteins ranging from 1-39, 1-40, 1-41, 1-42 and 1-43 residues in length. The 1-42 form is a central component of insoluble extracellular depositions (senile or neuritic plaques) composed of proteins, lipids, carbohydrates and salts in the brains of Alzheimer and Down's syndrome patients (Masters et al., PNAS 82, 4245-4249, 1985). In particular, amyloid β(1-42) and similar derivatives) protein is a polypeptide having 42 amino acids which is derived from the amyloid precursor protein (APP) by proteolytic processing. This also includes, in addition to human variants, isoforms of the amyloid β(1-42) protein present in organisms other than humans, in particular, other mammals, especially rats. This protein, which tends to polymerize in an aqueous environment, may be present in very different molecular forms.

A simple correlation of the deposition of insoluble protein with the occurrence or progression of dementia disorders such as, for example, Alzheimer's disease has proved to be unconvincing (Terry et al., Ann. Neurol. 30. 572-580 (1991), Dickson et al., Neurobiol. Aging 16, 285-298 (1995)). In contrast, the loss of synapses and cognitive perception seems to correlate better with soluble forms of Aβ(1-42)(Lue et al., Am. J. Pathol. 155, 853-862 (1999); McLean et al., Ann. Neurol. 46, 860-866 (1999)).

With the soluble forms of Aβ(1-42), there are essentially two different hypotheses regarding the to molecular forms that supposedly cause dementia disorders such as Alzheimer's disease. Firstly, a cytotoxic action of Aβ(1-42) protofibrils is postulated. The latter are still soluble, fibrillar, relatively highly aggregated Aβ(1-42) forms having molecular weights in the range from 150-250 kDa (Arispe et al. PNAS 90, 567 (1993), Lashuel et al., Nature 418, 291 (2002)) which, due to pore-forming properties, apparently cause an uncontrolled calcium influx through the membranes of neuronal cells. Secondly, oligomeric Aβ(1-42) derivatives having molecular weights in the range from 15-30 kDa have been described (M. P. Lambert et al. PNAS 95, 6448-6453 (1998)). These nonfibrillar oligomers also referred to as amyloid derived, diffusible and dementing ligands or ADDL's (see U.S. Pat. No. 6,218,506; International Application No. WO 01/10900; and Lambert et al., supra) can be found in preparations showing an inhibiting influence on the rate of long-term potentiation of neurons in hippocampal sections. However, the state of previous research on oligomers is characterized by great uncertainty over the actually relevant species. The information in the literature differs greatly. For example, U.S. Pat. No. 6,218,506 describes ADDLs having from 3 to 12 subunits, whereas the ADDLs described in International Application No. WO 01/10900 may have up to 24 subunits (see also Luhrs et al., PNAS 102(48), 17342-17347 (2005)).

In addition, the occurrence of N-terminally truncated forms of the Aβ(1-42) protein in connection with Alzheimer's disease has been reported Apart from Aβ(1-42), N-terminally truncated forms were also detected in the depositions of brains of deceased Alzheimer patients as early as 1985 (C. Masters et al., PNAS 92, 4245-4249 (1985)). Thus, particular proteases present in the brain, such as neprilysin (NEP 24.11) or IDE (short for insulin degrading enzyme), are also known to be able to degrade Aβ(1-42) (D. J. Selkoe, Neuron 32, 177-180, (2001)). However, the importance of the N-terminally truncated forms in the pathogenesis of Alzheimer's disease is unclear (Lee et al, JBS 278, 4458-4466 (2003)). Interestingly, some patients suffering from sporadic or familial Alzheimer's disease or Down's syndrome preferentially accumulate these truncated forms (J. Näslund et al., PNAS 91, 8378-8382, (1994), C. Russo et al., Nature 405, 531-532, (2000), T. C. Saido et al, Neuron 14, 457-466, (1995)). A relatively recent study (Sergeant et al., J. of Neurochemistry 85, 1581-1591, (2003)) showed that 60% of all insoluble Aβ peptides in the brains of deceased Alzheimer patients are based on N-terminally truncated forms.

In view of the above, there is certainly a need to produce large quantities of amyloid beta protein (of various forms) in order to meet the requirements of studies and resulting assays related to the detection of Alzheimer's Disease in humans and, more importantly, in the development of biologics and small molecules for the prevention and treatment of Alzheimer's Disease. Further, such production allows for further study into the properties of the protein in connection with the etiology of Alzheimer's. Thus, methods for producing this protein in sufficient quantity and in a native-like, functional form are invaluable.

Additionally, previous studies in vitro have relied upon chemically synthesized sequences which would result from natural cleavage points of the peptide. Also, studies in vivo typically rely upon biologically synthesized amyloid beta which self-evidently results from cleavage at the natural cleavage points. Thus, having the ability to produce large quantities of native and mutant amyloid peptides in a prokaryotic recombinant system such as *E. coli* will certainly be preferable to production methods currently in existence.

All patents and publications referred to herein are hereby incorporated in their entirety by reference.

SUMMARY OF THE INVENTION

The present invention encompasses a purified beta-amyloid protein having at least 70% amino acid sequence identity to a protein represented by the formula [X+Y], wherein "X" comprises one or more amino acids located at the amino terminus of the protein selected from the group consisting of methionine, valine and leucine and "Y" comprises all or a portion of the amino acid sequence of native amyloid beta protein. In particular, "Y" may comprise 39 to 43 contiguous amino acids of the native beta-amyloid protein. "Y" also includes the known human familial mutational variants which have at least 70% sequence identity to the amino acid sequence of the native beta-amyloid protein. Based on the numbering sequence of the Alzheimer's Precursor Protein (APP), these human familial mutants include, but are not limited to: Glu665Asp (Peacock, et al., Ann Neurol, 1994 April; 35(4):432-8); Lys/Met670Asn/Leu (Swedish) (Mullan, et al., Nat. Genet. 1992 August; 1(5):345-7); Ala673Thr (Peacock, et al., Neurology. 1993 June; 43(6):1254-6); HisG77Arg (Janssen, et al. Neurology. 2003 Jan. 28; 60(2): 235-9); AspG78Asn (Wakutani, et al. J Neurol Neurosurg Psychiatry. 2004 July; 75(7):1039-42); Ala692Gly (Flemish) (Kumar-Singh et al., Am J Pathol. 2002 Aug. 1; 161(2):507-520); Glu693Gly (Artic) Kamino, et al., Am J Hum Genet.

1992 November; 51(5):998-1014); Glu693Gln (Dutch) (Van Broeckhoven, et al. Science. 1990 Jun. 1; 248(4959):1120-2); Glu693Lys (Italian) (Tsubuki, et al., Lancet. 2003 Jun. 7; 361(9373):1957-8); Asp694Asn (Iowa) (Grabowski, et al., Ann Neurol. 2001 June; 49(6):697-705); Ala713Thr (Carter, et al., Nat. Genet. 1992 December; 2(4):255-6); Ala713Val (Jones, et al., Nat. Genet. 1992 July; 1(4):306-9). An noted above, "X" may be, for example, methionine.

Additionally, the present invention includes an isolated nucleic acid molecule encoding a beta-amyloid protein having at least 70% amino acid sequence identity to a protein represented by the formula [X+Y], wherein "X" comprises one or more amino acids located at the amino terminus of the protein selected from the group consisting of methionine, valine and leucine and "Y" comprises all or a portion of the amino acid sequence of native amyloid beta protein. "X" and "Y" may be as defined above. The invention also includes a vector comprising the isolated nucleic acid molecule as well as a host cell comprising this vector.

Further, the present invention encompasses a method of producing a purified beta-amyloid protein having at least 70% sequence identity to a protein represented by the formula [X+Y], wherein "X" comprises one or more amino acids located at the amino terminus of said protein selected from the group consisting of methionine, valine and leucine and "Y" comprises all or a portion of the amino acid sequence of native beta-amyloid protein. This method comprises the steps of: a) transfecting a nucleic acid molecule encoding the beta-amyloid protein described above into a vector; and b) transforming the vector of step a) into a host cell for a time and under conditions sufficient for expression of the beta-amyloid protein by the host cell. The host cell may be prokaryotic (e.g. *Escherichia coli, Bacillus* sp., *Streptococcus* sp. or *Lactobacillus* sp.) or eukaryotic cell (e.g., an insect cell, a yeast cell or a mammalian cell).

Also, the present invention includes an isolated antibody that binds to and/or is raised against the Met form of the beta-amyloid protein, as described above. It may be monoclonal or polyclonal. Preferably, it is monoclonal and is human or humanized. This antibody may have a specific binding constant (Kd) of at least 0.50 micromolar, a binding enthalpy of more than −30 kilojoules per mole and/or an antibody to amyloid globulomer binding ratio of at least one antibody per amyloid globulomer. (It is important to note that this antibody may also bind to the non-Met form of the antigen (e.g., Aβ(1-42) or Aβ(1-40)).

Additionally, the present invention includes a method of treating or prevention Alzheimer's Disease in a patient in need of the treatment or prevention. This method comprises administering the isolated antibody described above to the patient in an amount sufficient to effect the treatment or prevention. The antibody may be administered by any appropriate therapeutic route including, for example, intramuscularly, intravenously or subcutaneously.

Further, the present invention includes an isolated Met-beta-amyloid peptide oligomer comprising: 1) residues 19 to 21 and residues 30 to 32 oriented in an anti-parallel intra-chain orientation and 2) residues 34-38 oriented in a parallel inter-chain orientation. The oligomer also comprises A-beta (1-42) peptides having intramolecular interproton distances within approximately 1.8~65 Angstroms for atom pairs selected from the group consisting of: F19(NH)-I32(NH), F19(NH)-I32(HB), F19(NH)-I32 (HG##), A21(NH)-A30 (NH), A21(NH)-A30(HB#), A21(NH)-I31(HD1#), A21 (NH)-I31(HG1#), I32(NH)-F19(HD#), I32(NH)-F19(HB4) and A30(NH)-A21(HB#).

The invention additionally includes an isolated Met-beta-amyloid peptide oligomer, wherein the oligomer comprises A-beta (1-42) peptides having intermolecular interproton distances between peptide chain A and peptide chain B within approximately 1.8-5.5 Angstroms for atoms pairs selected from the group consisting of: G33(NH)-G34(NH), M35 (NH)-V36(NH), G37(NH)-G38(NH), G33(NH)-V18 (CγH₃), V18(NH)-V18(CγH₃), L34 (NH)-L34 (C₈H₃) M35 (NH)-V36 (CγH₃), G38 (NH)-V39 ((CγH₃) and V39 (NH)-V39((CγH₃). The oligomer also comprises an intra-molecular antiparallel β-sheet comprising at least residues 19-21 and 30-32 and atom pairs {F19 CO, I32 N}, {I32 CO, F19 N}, {A21 CO, A30 N}, and {A30 CO, A21 N} are at a distance of 3.3±0.5 Å, wherein CO indicates the backbone oxygen atom, and the phi (φ) angles of the residues range from −180 to −30 and psi (ψ) angles of the residues range from approximately 60 to 180 or from approximately −10 to −150.

Additionally, the present invention includes an isolated Met-beta-amyloid oligomer, wherein the oligomer comprises an inter-molecular parallel beta-sheet comprising at least residues 34-38 of at least two beta-amyloid peptides (labeled A and B), wherein the following atom pairs {G33 CO (A), L34 N (B)}, {L34 CO (B), M35 N (A)}, {M35 CO (A), V36 N (B)}, {V36 CO (B), G37 N (A)}, and {G37 CO (B), G38 N (A)} (where CO indicates the back-bone oxygen atom) are at a distance of 3.3±0.5 Å, and the phi (φ) angles of the residues range from −180 to −30 and psi (ψ) angles of the residues range from 60 to 180 or from −180 to −150.

Further, the present invention includes another isolated antibody which binds to at least one beta-amyloid N-Met 1-42 oligomer. This oligomer may be selected from, for example, the group consisting of: (a) An intra-molecular antiparallel beta-sheet comprising at least residues 19-21 and 30-32, wherein the following atom pairs {F19 CO, I32 N)}, {I32 CO, F19 N}, {A21 CO, A30 N}, and {A30 CO, A21 N} (where CO indicates the backbone oxygen atom) are at a distance of 3.3±0.5 Å, and the phi (φ) angles of the residues range from −180 to −30 and psi (ψ) angles of the residues range from 60 to 180 or from −180 to −150; and (b) An inter-molecular parallel beta-sheet comprising at least residues 34-38 of at least two beta-amyloid peptides (labeled A and B), wherein the following atom pairs {G33 CO (A), L34 N (B)}, {L34 CO (B), M35 N (A)}, {M35 CO (A), V36 N (B)}, {V36 CO (B), G37 N (A)}, and {G37 CO (B), G38 N (A)} (where CO indicates the backbone oxygen atom) are at a distance of 3.3±0.5 Å, and the phi (φ) angles of the residues range from −180 to −30 and psi (ψ) angles of the residues range from 60 to 180 or from −180 to −150. This antibody-oligomer complex may have a three-dimensional structure comprising at least two N-Met 1-42 beta-amyloid peptides which, in turn, comprise any physically allowed conformation shown in FIGS. 20 and 21. (This antibody may also bind to non-Met forms of the antigen, as well as to truncated portions of the Met and non-Met forms.)

Additionally, the present invention includes a purified Met-containing globulomer comprising at least two of the isolated beta-amyloid proteins described above as well as an isolated antibody which binds to the purified globulomer.

In connection with diagnostic uses, the prevent invention includes a method of diagnosing Alzheimer's Disease in a patient suspected of having this disease. This method comprises the steps of: a) isolating a biological sample from the patient; b) contacting the biological sample with one or more of the isolated antibodies, for a time and under conditions sufficient for the formation of globulomer/antibody complexes; and c) detecting presence of the globulomer/antibody complexes in the sample, the presence of the complexes indicating a diagnosis of Alzheimer's Disease in said patient.

The prevent invention also includes a method of diagnosing Alzheimer's Disease in a patient suspected of having this disease comprising the steps of: a) isolating a biological sample from the patient; b) contacting the biological sample with a Met-containing form of the globulomer for a time and under conditions sufficient for the formation of antibody/globulomer complexes; c) adding a conjugate to the resulting antibody/globulomer complexes for a time and under conditions sufficient to allow the conjugate to bind to the bound antibody, wherein the conjugate comprises an antibody attached to a signal generating compound capable of generating a detectable signal; and d) detecting the presence of antibodies which may be present in the biological sample by detecting a signal generated by the signal generating compound, the signal indicating a diagnosis of Alzheimer's Disease in the patient.

The present invention includes a further method of diagnosing Alzheimer's Disease in a patient suspected of having Alzheimer's Disease comprising the steps of: a) isolating a biological sample from the patient; b) contacting the biological sample with the Met-containing form of the globulomer described above for a time and under conditions sufficient for formation of antibody/purified globulomer complexes; and c) detecting presence of the antibody/purified globulomer complexes in the sample, presence of the complexes indicating a diagnosis of Alzheimer's Disease in the patient.

Further, the present invention includes another method of diagnosing Alzheimer's Disease in a patient suspected of having Alzheimer's Disease comprising the steps of: a) isolating a biological sample from the patient;
contacting the biological sample with anti-antibody specific for antibodies in the sample for a time and under conditions sufficient to allow for formation of anti-antibody/antibody complexes; b) adding a conjugate to resulting anti-antibody/antibody complexes for a time and under conditions sufficient to allow the conjugate to bind to bound antibody, wherein the conjugate comprises a Met-containing globulomer attached to a signal generating compound capable of generating a detectable signal; and c) detecting a signal generated by the signal generating compound, the signal indicating a diagnosis of Alzheimer's Disease in the patient.

The present invention also includes a vaccine comprising the purified Met-beta-amyloid protein described above and a pharmaceutically acceptable adjuvant. Further, the invention includes a vaccine comprising an antibody, raised against the purified Met-beta-amyloid protein or which binds to the protein, and a pharmaceutically acceptable adjuvant.

Further, the present invention also includes a method of preventing or treating Alzheimer's Disease in a patient in need of the prevention or treatment comprising the step of administering the vaccines described above to the patient in an amount sufficient to effect the prevention or treatment.

Additionally, the present invention includes a method of identifying compounds for treatment or prevention of Alzheimer's Disease. This method comprises the steps of:
a) exposing one or more compounds of interest to the purified Met-containing globulomer described above for a time and under conditions sufficient for the one or more compounds to bind to or neutralize the purified globulomer; and b) identifying those compounds which bind to or neutralize the purified globulomer, the identified compounds to be used in the treatment or prevention of Alzheimer's Disease.

Moreover, the present invention includes a method of designing a small molecule useful in the treatment or prevention of Alzheimer's Disease in a patient. This method comprises the steps of: a) analyzing the three dimensional structure of a protein such as the purified Met-containing globulomer described above, the isolated Met-containing beta-amyloid protein composition described above, or an assembly of the isolated Met-containing beta-amyloid protein compositions; b) identifying one or more epitopes on the surface of the selected protein of step a); and c) designing a small molecule which will bind to the identified epitope or epitopes of step b), the small molecule to be used in the treatment or prevention of Alzheimer's Disease.

The present invention also includes a method of identifying a monoclonal antibody to be used in the treatment or prevention of Alzheimer's Disease. This method comprises the steps of: a) exposing the purified Met-containing globulomer described above to a library of monoclonal antibodies for a time and under conditions sufficient for binding of one or more of the monoclonal antibodies to the globulomer and formation of globulomer/antibody complexes; b) identifying presence of the globulomer/antibody complexes; and c) determining the identity of one or more antibodies within the complexes, the one or more antibodies to be used in the treatment or prevention of Alzheimer's Disease.

Further, the present invention includes a method of stabilizing a sample of Met-containing (or non-Met containing) amyloid beta(1-42) oligomers or portions thereof comprising the step of adding an alkyl chain detergent or lipid to the sample for a time (i.e., 1-2 hours) and in an amount (i.e., 5% aqueous suspension or solution) sufficient to effect the stabilization.

The present invention also includes a purified, Met-containing globulomer comprising at least two of the isolated amyloid beta proteins described above.

Further, the present invention encompasses an isolated antibody, which binds to amino acid residues E22-D23-V24-G25-S26-N27-K28 (SEQ ID NO: 25) of the protein illustrated in FIG. 21. The present invention also includes the epitope itself. This sequence may further comprise G29 after K28. Additionally, the present invention includes at least 2, 3, 4, 5, 6, 7, 8, 9 or 10 contiguous amino acids of the protein of FIG. 21 starting at position A21. Additionally, it should be noted that this epitope may be found in the non-Met forms of Aβ(1-42) protein and Aβ(1-40) protein in addition to the Met-forms of Aβ protein described above.

Additionally, it must be noted that expression of small peptides in *E. coli*, such as those of the present invention, would be expected to be rapidly degraded due to presence of natural proteases in the microorganism. However, the present invention shows that the methionine form of amyloid beta protein remains fully intact upon expression in the host cell with the additional feature that the protein produced contains the precise amino acid sequence that is encoded in the amyloid precursor protein known as APP.

BRIEF DESCRIPTION OF THE DRAWINGS

FIG. 1(A) illustrates the DNA sequence of the gene encoding the β-amyloid peptide (SEQ ID NO:1). The nucleotide restriction sites used for cloning are indicated and were not included in the primers designed. The starting Met (ATG) and the stop codon (TGA) are indicated FIG. 1(B) illustrates the amino acid sequence of the native amyloid beta (1-42) protein (SEQ ID NO:2) derived from processing in vivo of the amyloid precursor protein (APP).

FIG. 2 illustrates various forms of amyloid beta peptide or protein containing the natural the N-terminal methionine, extending out to natural sequence (including known mutational variants) residues 40 to 44 (SEQ ID NO:3=1-39, SEQ ID NO:4=1-40, SEQ ID NO:6=1-41, SEQ ID NO:6=1-42, SEQ ID NO:7=1-43 and SEQ ID NO: 27=20-42).

FIG. 24 depicts the coordinates of the beta-amyloid component of the observed globulomers of the present invention. The coordinates are for a model of the dimmer component of beta-amyloid peptide N-Met 1-42 globulomer. The sequence number of one molecule is 15-42 (SEQ ID NO: 29), while the sequence number for another molecule is 115-142 (SEQ ID NO: 29).

FIGS. 25 A-C illustrate a comparison of backbone amide protection of the globulomer (panel B) and fibril (panel C) forms of the amyloid β peptide.

FIG. 26A discloses SEQ ID NO: 2.

DETAILED DESCRIPTION OF THE INVENTION

Figure 3A:
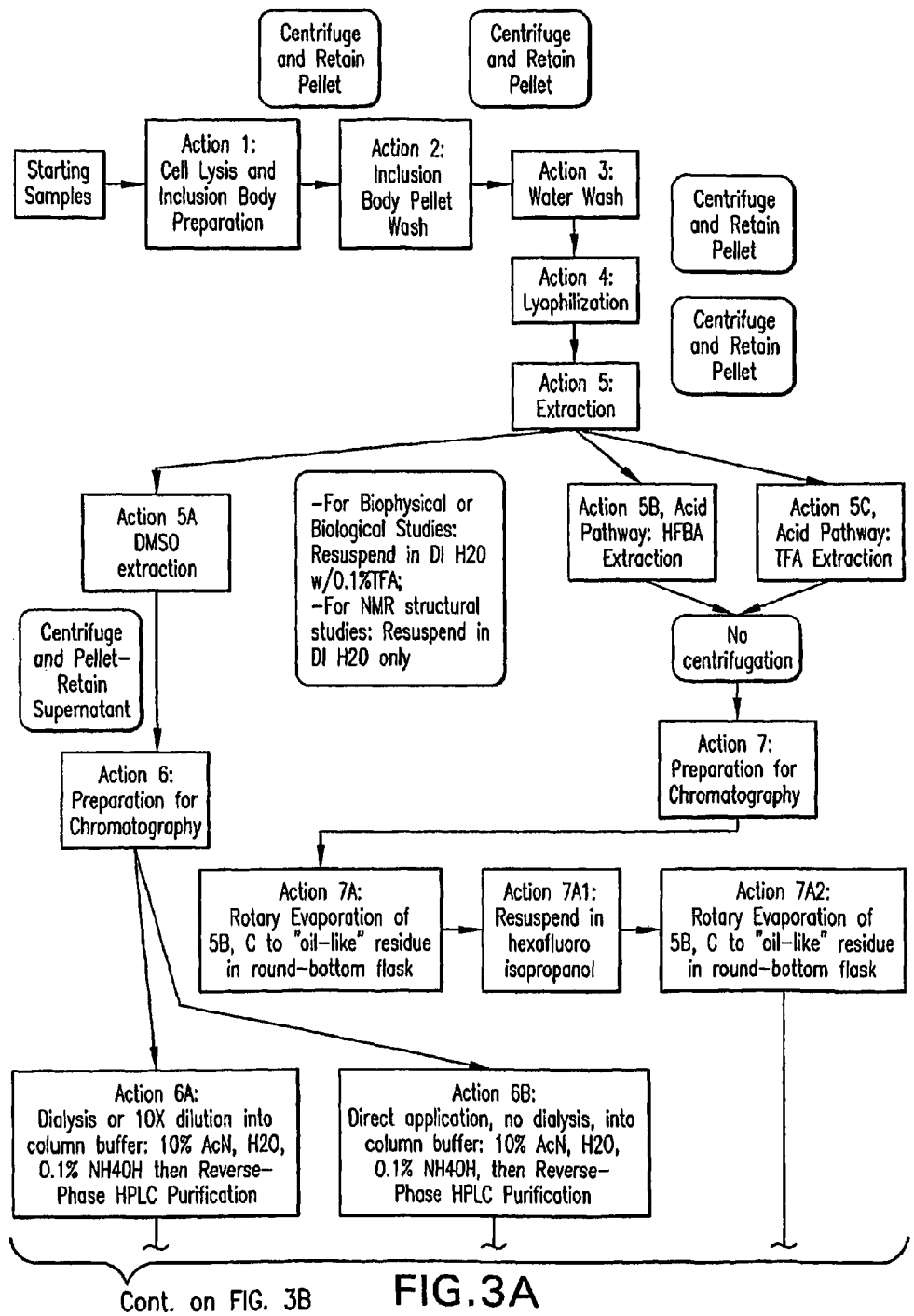
FIG. 3 represents a purification schema for recombinant amyloid beta.

The present invention relates to recombinant forms of amyloid beta protein as well as to methods of production thereof. More specifically, the present invention includes an amyloid beta protein represented by the formula [X+Y] wherein "X" comprises one or more amino acids, at the amino or N-terminus of the amino acid sequence of the peptide, selected from the group consisting of methionine (Met), Valine (Val) and Leucine (Leu). Preferably, "X" comprises Met.

Further, "Y" represents the number of amino acids within the peptide with the exception of the "X" amino acid or acids at the amino terminus. In particular, "Y" represents an integer from 39-43 and represents a portion of or all of the native amyloid beta (1-42) amino acid sequence. This amino acid sequence may begin at any amino acid "number" or position within the native 1-42 sequence (e.g., amino acid 1, amino acid 5, amino acid 12, amino acid 22, amino acid 35, etc.) and may end at any amino acid number or position within the native sequence, provided the total number of native amino acids selected ranges from 38-43. Other properties of the proteins of the present invention include the ability to bind to antibodies as illustrated in Figures X-Y. The binding characteristics being: 1) a Kd less than or equal to 0.50 micromolar; 2) a favorable binding enthalpy (negative ΔH) greater than negative 30 kilojoules per mole; and 3) an antibody to amyloid binding ratio of at least one antibody per amyloid globulomer.

In addition to the amino acid sequences or proteins of the present invention, the invention also includes amino acid sequences comprising, corresponding to, identical to, or complementary to at least about 70%, preferably at least about 80%, and more preferably at least about 90% identity to the amino acid sequences of the proteins of the present invention. (Again, all integers (and portions thereof) between 70% and 100% are also considered to be within the scope of the present invention with respect to percent identity.)

It should be noted that the present invention also encompasses isolated nucleotide sequences encoding the proteins of the present invention as well as those having sequences comprising, corresponding to, identical to, or complementary to at least about 70%, preferably at least about 80%, and more preferably at least about 90% identity to these encoding nucleotide sequences. (All integers (and portions thereof) between 70% and 100% are also considered to be within the scope of the present invention with respect to percent identity.) Such sequences may be derived from any source, either isolated from a natural source, produced via a semi-synthetic route, or synthesized de novo. In particular, such sequences may be isolated or derived from sources other than described in the examples (e.g., bacteria, fungus, algae, mouse or human).

For purposes of the present invention, a "fragment" of a nucleotide sequence is defined as a contiguous sequence of approximately at least 6, preferably at least about B, more preferably at least about 10 nucleotides, and even more preferably at least about 15 nucleotides corresponding to a region of the specified nucleotide sequence.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences, ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

Additionally, a nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold spring harbor Press, Cold Spring harbor, N.Y., 1989, as noted above and incorporated herein by reference. (See also Short Protocols in Molecular Biology, ed. Ausubel et al. and Tijssen, Techniques in Biochemistry and Molecular Biology-Hybridization with Nucleic Acid Probes, "Overview of principles of hybridization and the strategy of nucleic acid assays" (1993), both incorporated herein by reference.) Specifically, the choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS Hybridization is carried out at about 68 degrees Celsius for about 3 to 4 hours for fragments of cloned DNA and for about 12 to about 16 hours for total eukaryotic DNA. For moderate stringencies, one may utilize filter pre-hybridizing and hybridizing with a solution of 3× sodium chloride, sodium citrate (SSC), 50% formamide (0.1 M of this buffer at pH 7.5) and 5×Denhardt's solution. One may then pre-hybridize at 37 degrees Celsius for 4 hours, followed by hybridization at 37 degrees Celsius with an amount of labeled probe equal to 3,000,000 cpm total for 16 hours, followed by a wash in 2×SSC and 0.1% SDS solution, a wash of 4 times for 1 minute each at room temperature and 4 times at 60 degrees Celsius for 30 minutes each. Subsequent to drying, one exposes to film. For lower stringencies, the temperature of hybridization is reduced to about 12 degrees Celsius below the melting temperature ($T_m$) of the duplex. The $T_m$ is known to be a function of the G-C content and duplex length as well as the ionic strength of the solution.

"Hybridization" requires that two nucleic acids contain complementary sequences. However, depending on the stringency of the hybridization, mismatches between bases may occur. As noted above, the appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster/, G. D. (1995) *Molecular Biotechnology* 3:225).

The "31 non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 31 non-coding sequences is exemplified by Ingelbrecht et al., *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 51 and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform the host or host cell as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Once the nucleotide sequence encoding the beta-amyloid protein of interest has been isolated, it may then be introduced into either a prokaryotic or eukaryotic host cell, preferably a prokaryotic host cell such as *E. coli*, through the use of a vector or construct.

The nucleotide sequence encoding the N-terminus of the expressed protein must also be introduced into the vector. Further, the vector, for example, a bacteriophage, cosmid or plasmid, may comprise the nucleotide sequence encoding the relevant portion of the native amyloid beta protein, the nucleotide sequence of the N-terminus to be encoded, as well as any regulatory sequence (e.g., promoter) that is functional in the host cell and is able to elicit expression of the protein. The regulatory sequence (e.g., promoter) is in operable association with, or operably linked to, the nucleotide sequence (A promoter or regulatory sequence is said to be "operably linked" with a coding sequence if the promoter or regulatory sequence affects transcription or expression of the coding sequence.) Suitable promoters include, for example, the T7 lac promoter, the T7 promoter, pBAD, the tet promoter, the Lac promoter, the Trc promoter, the Trc promoter and the PL promoter, all of which can be utilized when trying to express the protein in a bacterial cell such as *E. coli*, for example. If one is utilizing an insect as the host cell, promoters such as polyhedrin, P10, MT, Ac5 and Op1E2 may be utilized. If one prefers to express the protein in a virus, pCMV, pUbC and pU6 may be used as promoters. Promoters which may be utilized in mammalian cells include, for example, CMV, U6, EF-1, pCMV-2×TetO$_2$, pUbC, SV40, b-casein and RSV. Suitable yeast promoters include AOX1, GAP, AUG1, GAL1, nmt1, nmt41, nmt81 and TEF1. The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, 2$^{nd}$ ed., Vol. 1-3, ed. Sambrook et al., Cold Spring Harbor Laboratory Press (1989)). The host cell is then cultured under suitable conditions permitting expression of the nucleotide sequences leading to the production of the desired, encoded amyloid beta protein which is then recovered and purified.

Examples of suitable prokaryotic host cells include, for example, bacteria such as Escherichia coli, Bacillus sp., Streptococcus sp. and Lactobacillus sp. Examples of suitable eukaryotic host cells include, for example, insect cells (e.g., SF9, SF21 and Hi5), yeast cells, S. pombe, mammalian cells and Drosophila cells.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by inducing the activity of a regulatable promoter operably linked to the gene of interest; although, such inducible systems frequently exhibit a low basal level of expression Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the protein of interest. More specifically, once the above-described construct is created, it may be inserted into the pronucleus of an embryo. The embryo may then be implanted into a recipient female. Alternatively, a nuclear transfer method could also be utilized (Schnieke et al., Science 278: 2130-2133 (1997)). Gestation and birth are then permitted (see, e.g., U.S. Pat. No. 5,750,176 and U.S. Pat. No. 5,700, 671). The mammal utilized as the host may be selected from the group consisting of, for example, a mouse, a rat, a rabbit, a pig, a goat, a sheep, a horse and a cow. However, any mammal may be used provided it has the ability to incorporate DNA encoding the protein of interest into its genome.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis Analyzing DNA, 2, Cold Spring Harbor, N.Y. (1998); Plant Molecular Biology: A Laboratory Manual, eds. Clark, Springer, New York (1997)).

The term "Aβ(X-Y)" herein refers to the amino acid sequence from amino acid position X to amino acid position Y of the human amyloid β protein including both X and Y, in particular to the amino acid sequence from amino acid position X to amino acid position Y of the amino acid sequence DAEFRHDSGY EVHHQKLVFF AEDVGSNKGA IIGLM-VGGW IA (SEQ ID NO: 2) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both position X and position Y or a sequence with up to three additional amino acid substitutions none of which may prevent globulomer formation, an "additional" amino acid substitution herein being any deviation from the canonical sequence that is not found in nature.

More specifically, the term "Aβ(1-42)" herein refers to the amino acid sequence from amino acid position 1 to amino acid position 42 of the human amyloid β protein including both 1 and 42, in particular to the amino acid sequence from amino acid position 1 to amino acid position 42 of the amino acid sequence DAEFRHDSGY EVHHQKLVFF AEDVG-SNKGA IIGLMVGGVV IA (SEQ ID NO: 2) (corresponding to amino acid positions 1 to 42) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both 1 and 42 or a sequence with up to three additional amino acid substitutions none of which may prevent globulomer formation. Likewise, the term "Aβ(1-40)" here refers to the amino acid sequence from amino acid position 1 to amino acid position 40 of the human amyloid β protein including both 1 and 40, in particular to the amino acid sequence from amino acid position 1 to amino acid position 40 of the amino acid sequence DAEFRHDSGY EVHHQKLVFF AEDVG-SNKGA IIGLMVGGVV (SEQ ID NO: 26) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), and D23N ("Iowa") wherein the numbers are relative to the start of the Aβ peptide, including both 1 and 40 or a sequence with up to three additional amino acid substitutions none of which may prevent globulomer formation.

The term "Aβ(X-Y) globulomer" (Aβ(X-Y) globular oligomers) herein refers to a soluble, globular, non-covalent association of Aβ (X-Y) peptides as defined above, possessing homogeneity and distinct physical characteristics. The Aβ(X-Y) globulomers are stable, non-fibrillar, oligomeric assemblies of Aβ (X-Y) peptides which are obtainable by incubation with anionic detergents. In contrast to monomer and fibrils, these globulomers are characterized by defined assembly numbers of subunits (e.g., early assembly forms, n=4-6, oligomers A", and late assembly forms, n=12-14, "oligomers B", as described in WO2004/067561). The globulomers have a 3 dimensional globular type structure ("molten globule", see Barghorn et al., 2005, J Neurochem, 95, 834-847). They may be further characterized by one or more of the following features:

cleavability of N-terminal amino acids X-23 with promiscuous proteases (such as thermolysin or endoproteinase GluC) yielding truncated forms Aβ(X-Y) globulomers;

non-accessibility of C-terminal amino acids 24-Y with promiscuous proteases and antibodies;

truncated forms of these Aβ(X-Y) globulomers maintain the 3-dimensional core structure of the globulomers with a better accessibility of the core epitope Aβ(20-Y) in its globulomer conformation.

According to the invention and in particular for the purpose of assessing the binding affinities of the antibodies of the present invention, the term "Aβ(X-Y) globulomer" here refers to a product which is obtainable by a process as described in WO 2004/067561, which is incorporated herein by reference. Said process comprises unfolding a natural, recombinant or synthetic Aβ(X-Y) peptide or a derivative thereof; exposing the at least partially unfolded Aβ(X-Y) peptide or derivative thereof to a detergent, reducing the detergent action and continuing incubation.

For this purpose of unfolding of the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about −20° C., for an interim period.

Alternatively, the peptide or a derivative thereof may be taken up in slightly acidic, preferably aqueous, solution, for example an about 10 mM aqueous HCl solution. After an incubation time of usually a few minutes, insoluble components are removed by centrifugation. A few minutes at 10,000 g is expedient. These method steps are preferably carried out at room temperature, i.e., a temperature in the range from 20 to 30° C. The supernatant obtained after centrifugation contains the Aβ(X-Y) peptide or a derivative thereof and may be stored at low temperature, for example at about −20° C., for an interim period.

The following exposure to a detergent relates to oligomerization of the peptide or the derivative thereof to give the intermediate type of oligomers (in WO 2004/067561 referred to as oligomers A). For this purpose, a detergent is allowed to act on the at least partially unfolded peptide or derivative thereof until sufficient intermediate oligomer has been produced. Preference is given to using ionic detergents, in particular anionic detergents.

According to a particular embodiment, a detergent of the formula (I):

R—X, is used, in which the radical R is unbranched or branched alkyl having from 6 to 20 and preferably 10 to 14 carbon atoms or unbranched or branched alkenyl having from 6 to 20 and preferably 10 to 14 carbon atoms, the radical X is an acidic group or salt thereof, with X being preferably selected from among $-COO^-M^+$, $-SO_3^-M^+$, and especially $-OSO_3^-M^+$ and $M^+$ is a hydrogen cation or an inorganic or organic cation preferably selected from alkali metal and alkaline earth metal cations and ammonium cations. Advantageous are detergents of the formula (I), in which R is unbranched alkyl of which alk-1-yl radicals must be mentioned in particular. Particular preference is given to sodium dodecyl sulfate (SDS). Lauric acid and oleic acid can also be used advantageously. The sodium salt of the detergent lauroylsarcosin (also known as sarkosyl NL-30 or Gardol®) is also particularly advantageous.

The time of detergent action in particular depends on whether, and if yes, to what extent the peptide or derivative thereof subjected to oligomerization has unfolded. If, according to the unfolding step, the peptide or derivative thereof has been treated beforehand with a hydrogen bond-breaking agent, i.e., in particular with hexafluoroisopropanol, times of action in the range of a few hours, advantageously from about 1 to 20 and in particular from about 2 to 10 hours, are sufficient when the temperature of action is about 20 to 50° C. and in particular about 35 to 40° C. If a less unfolded or an essentially not unfolded peptide or derivative thereof is the starting point, correspondingly longer times of action are expedient. If the peptide or derivative thereof has been pretreated, for example, according to the procedure indicated above as an alternative to HFIP treatment or said peptide or derivative thereof is directly subjected to oligomerization, times of action in the range from about 5 to 30 hours and in particular from about 10 to 20 hours are sufficient when the temperature of action is about 20 to 50° C. and in particular about 35 to 40° C. After incubation, insoluble components are advantageously removed by centrifugation. A few minutes at 10,000 g is expedient.

The detergent concentration to be chosen depends on the detergent used. If SDS is used, a concentration in the range from 0.01 to 1% by weight, preferably from 0.05 to 0.5% by weight, for example of about 0.2% by weight, proves expedient. If lauric acid or oleic acid are used, somewhat higher concentrations are expedient, for example in a range from 0.05 to 2% by weight, preferably from 0.1 to 0.5% by weight, for example of about 0.5% by weight.

The detergent action should take place at a salt concentration approximately in the physiological range. Thus, in particular HaCl concentrations in the range from 50 to 500 mM, preferably from 100 to 200 mM and particularly at about 140 mM are expedient.

The subsequent reduction of the detergent action and continuation of incubation relates to further oligomerization to give the Aβ(X-Y) globulomer of the invention (in WO 2004/067561 referred to as oligomers B). Since the composition obtained from the preceding step regularly contains detergent and a salt concentration in the physiological range, it is then expedient to reduce detergent action and, preferably, also the salt concentration. This may be carried out by reducing the concentration of detergent and salt, for example, by diluting, expediently with water or a buffer of lower salt concentration, for example Tris-HCl, pH 7.3. Dilution factors in the range from about 2 to 10, advantageously in the range from about 3 to 8 and in particular of about 4, have proved suitable The reduction in detergent action may also be achieved by adding substances which can neutralize said detergent action. Examples of these include substances capable of complexing the detergents, like substances capable of stabilizing cells in the course of purification and extraction measures, for example particular, BO/PO block copolymers, in particular the block copolymer under the trade name Pluronic® F 68. Alkoxylated and, in particular, ethoxylated alkyl phenols such as the ethoxylated t-octylphenols of the Triton® X series, in particular Triton® X100, 3-(3-cholamidopropyldimethylammonio)-1-propanesulfonate (CHAPS®) or alkoxylated and, in particular, ethoxylated sorbitan fatty esters such as those of the Tween® series, in particular Tween® 20, in concentration ranges around or above the particular critical micelle concentration, may be equally used.

Subsequently, the solution is incubated until sufficient Aβ(X-Y) globulomer of the invention has been produced. Times of action in the range of several hours, preferably in the range from about 10 to 30 hours and in particular in the range from about 15 to 25 hours, are sufficient when the temperature of action is about 20 to 50° C. and in particular about 35 to 40° C. The solution may then be concentrated and possible residues may be removed by centrifugation. Here too, a few minutes at 10,000 g proves expedient. The supernatant obtained after centrifugation contains Aβ(X-Y) globulomer of the invention.

An Aβ(X-Y) globulomer of the invention can be finally recovered in a manner perse, e.g. by ultrafiltration, dialysis, precipitation or centrifugation. It is further preferred if electrophoretic separation of the Aβ(X-Y) globulomers under denaturing conditions, e.g. by SDS-PAGE, produces a double band (e.g. with an apparent molecular weight of 38/48 kDa for Aβ (1-42)), and especially preferred if upon glutardialdehyde treatment of the oligomers before separation these two bands are merged into one. It is also preferred if size exclusion chromatography of the globulomers results in a single peak (e.g., corresponding to a molecular weight of approximately 60 kDa for Aβ (1-42)).

Starting out from Aβ(1-42) peptide, said process is, in particular, suitable for obtaining Aβ(1-42) globulomers Preferably, the globulomer shows affinity to neuronal cells. Preferably, the globulomer also exhibits neuromodulating effects.

According to another aspect of the invention, the term "Aβ(X-Y) globulomer" here refers to a globulomer consisting essentially of Aβ(X-Y) subunits, where it is preferred if on average at least 11 of 12 subunits are of the Aβ(X-Y) type, more preferred if less than 10% of the globulomers comprise any non-Aβ(X-Y) peptides, and most preferred if the content of non-Aβ(X-Y) peptides in the preparation is below the detection threshold. More specifically, the term "Aβ(142) globulomer" herein refers to a globulomer consisting essentially of Aβ(1-42) units as defined above; the term "Aβ(12-42) globulomer" here refers to a globulomer consisting essentially of Aβ(12-42) units as defined above; and the term "Aβ(20-42) globulomer" here refers to a globulomer consisting essentially of Aβ(20-42) units as defined above.

The term "cross-linked Aβ(X-Y) globulomer" herein refers to a molecule obtainable from an Aβ(X-Y) globulomer as described above by cross-linking, preferably chemically cross-linking, more preferably aldehyde cross-linking, most preferably glutardialdehyde cross-linking of the constituent units of the globulomer. In another aspect of the invention, a cross-linked globulomer is essentially a globulomer in which the units are at least partially joined by covalent bonds, rather than being held together by non-covalent interactions only.

The term "Aβ(X-Y) globulomer derivative" herein refers in particular to a globulomer that is labelled by being covalently linked to a group that facilitates detection, preferably a fluorophore, e.g., fluorescein isothiocyanate, phycoerythrin, Aequorea Victoria fluorescent protein, Dictyosoma fluorescent protein or any combination or fluorescence-active derivative thereof; a chromophore; a chemoluminophore, e.g., luciferase, preferably *Photinus pyralis* luciferase, *Vibrio fischeri* luciferase, or any combination or chemoluminescence-active derivative thereof; an enzymatically active group, e.g., peroxidase, e.g., horseradish peroxidase, or any enzymatically active derivative thereof; an electron-dense group, e.g., a heavy metal containing group, e.g., a gold containing group; a hapten, e.g., a phenol derived hapten; a strongly antigenic structure, e.g., peptide sequence predicted to be antigenic, e.g., predicted to be antigenic by the algorithm of Kolaskar and Tongaonkar; an aptamer for another molecule; a chelating group, e.g., hexahistidinyl; a natural or nature-derived protein structure mediating further specific protein-protein interactions, e.g., a member of the fos/jun pair; a magnetic group, e.g., a ferromagnetic group; or a radioactive group, e.g., a group comprising $^{1}H$, $^{14}C$, $^{32}P$, $^{35}S$ or $^{125}I$ or any combination thereof; or to a globulomer flagged by being covalently or by non-covalent high-affinity interaction, preferably covalently linked to a group that facilitates inactivation, sequestration, degradation and/or precipitation, preferably flagged with a group that promotes in vivo degradation, more preferably with ubiquitin, where is particularly preferred if this flagged oligomer is assembled in vivo; or to a globulomer modified by any combination of the above. Such labelling and flagging groups and methods for attaching them to proteins are known in the art. Labelling and/or flagging may be performed before, during or after globulomerization. In another aspect of the invention, a globulomer derivative is a molecule obtainable from a globulomer by a labelling and/or flagging reaction. Correspondingly, term "Aβ(X-Y) monomer derivative" here refers in particular to an Aβ monomer that is labelled or flagged as described for the globulomer.

The term "greater affinity" herein refers to a degree of interaction where the equilibrium between unbound antibody and unbound globulomer on the one hand and antibody-globulomer complex on the other is further in favour of the antibody-globulomer complex. Likewise, the term "smaller affinity" here refers to a degree of interaction where the equilibrium between unbound antibody and unbound globulomer on the one hand and antibody-globulomer complex on the other is further in favour of the unbound antibody and unbound globulomer.

The term "Aβ(X-Y) monomer" here refers to the isolated form of the Aβ(X-Y) peptide, preferably a form of the Aβ(X-Y) peptide which is not engaged in essentially non-covalent interactions with other Aβ peptides. Practically, the Aβ(X-Y) monomer is usually provided in the form of an aqueous solution. In a particularly preferred embodiment of the invention, the aqueous monomer solution contains 0.05% to 0.2%, more preferably about 0.1% $NH_4OH$. In another particularly preferred embodiment of the invention, the aqueous monomer solution contains 0.05% to 0.2%, more preferably about 0.1% NaOH. When used, it may be expedient to dilute said solution in an appropriate manner. Further, it is usually expedient to use said solution within 2 hours, in particular within 1 hour, and especially within 30 minutes after its preparation.

The term "fibril" here refers to a molecular structure that comprises assemblies of non-covalently associated, individual Aβ(X-Y) peptides, which show fibrillary structure in the electron microscope, which bind Congo red and then exhibit birefringence under polarized light and whose X-ray diffraction pattern is a cross-β structure.

In another aspect of the invention, a fibril is a molecular structure obtainable by a process that comprises the self-induced polymeric aggregation of a suitable Aβ peptide in the absence of detergents, e.g., in 0.1 M HCl, leading to the formation of aggregates of more than 24, preferably more than 100 units. This process is well known in the art. Expediently, Aβ(X-Y) fibril is used in the form of an aqueous solution. In a particularly preferred embodiment of the invention, the aqueous fibril solution is made by dissolving the Aβ peptide in 0.1% $NH_4OH$, diluting it 1:4 with 20 mM $NaH_2PO_4$, 140 mM NaCl, pH 7.4, followed by readjusting the pH to 7.4, incubating the solution at 37° C. for 20 h, followed by centrifugation at 10000 g for 10 min and resuspension in 20 mM $NaH_2PO_4$, 140 mM NaCl, pH 7.4.

The term "Aβ(X-Y) fibril" herein refers to a fibril consisting essentially of Aβ(X-Y) subunits, where it is preferred if on average at least 90% of the subunits are of the Aβ(X-Y) type, more preferred if at least 98% of the subunits are of the Aβ(X-Y) type, and most preferred if the content of non-Aβ(X-Y) peptides is below the detection threshold.

Uses of the Recombinant Amyloid Beta Protein

The proteins produced in accordance with the methods of the present invention have many interesting utilities as do the methods themselves. For example, the methods eliminate the need for the preparation of the peptides by synthetic-organic means. Further, the methods allow for large savings in production costs, as large scale recombinant expression is far less expensive than peptide synthesis.

Additionally, the methods of the present invention allow for facile introduction of any of the naturally-occurring amino acid variants associated with various, currently identified Alzheimer's family disorders as well as any identified in the future.

Also, the methods of the present invention allow one to prepare appropriate amounts of starting material for use in the preparation of further materials that, in turn, may be utilized in the production of monoclonal antibodies (or other antibodies) for the treatment of Alzheimer's Disease.

Figure 18:
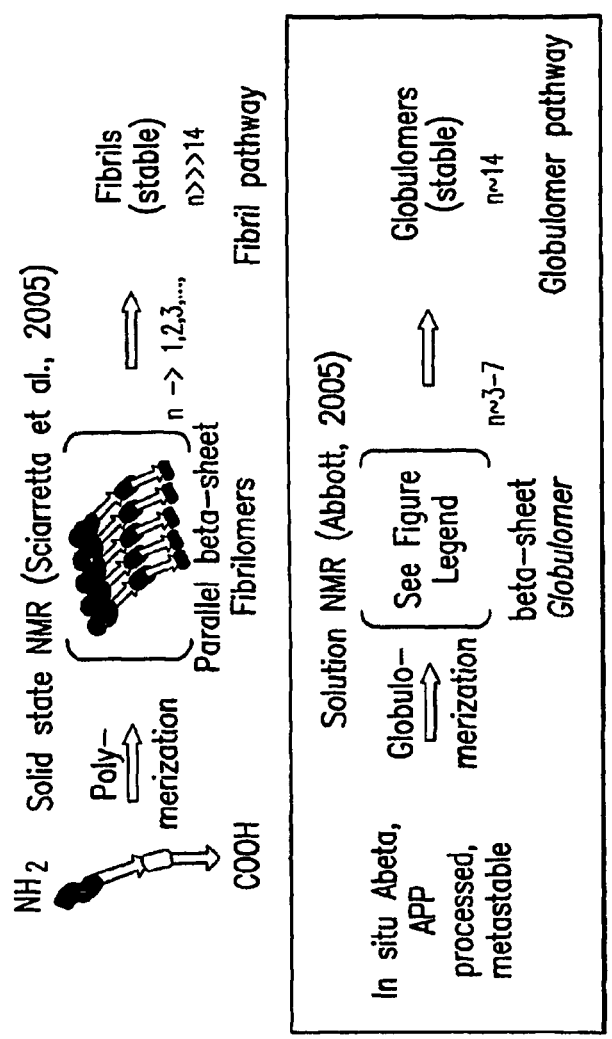
FIG. 18 depicts the distinct structural differences between the previously proposed parallel β-sheet fibrillar structural pathway (Sciaretta et al., Biochemistry 2005, 44:6003-6014) based upon solid-state NMR and the observed mixed parallel/anti-parallel structural pathway of the globulomers described herein.
Figure 19:
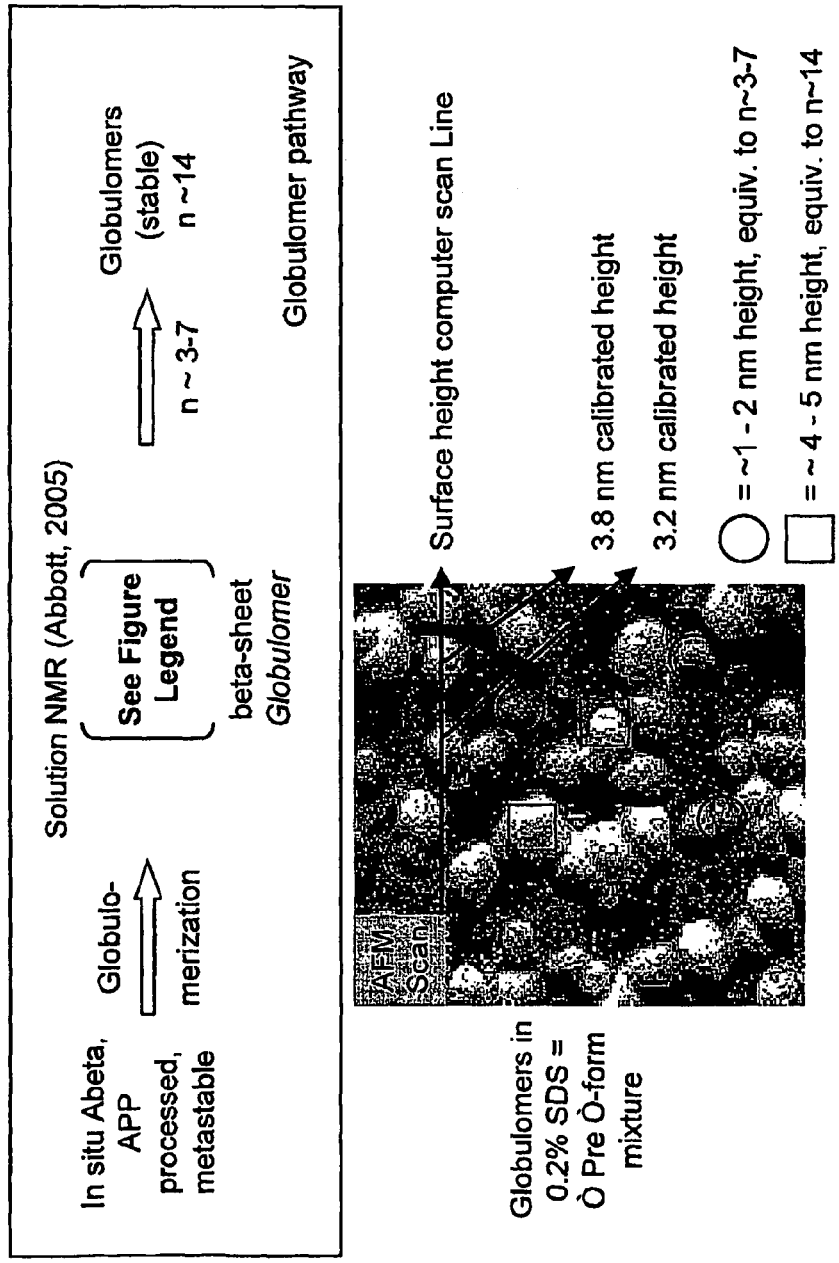
FIG. 19 depicts the AFM images of the smallest observed globulomer species (1-2 nm high) believed to be observed by solution-state NMR in SDS (about 1.5%) intermixed with the slightly larger (4-5 nm) full globulomers. Edge image data only; the sharpest features are lighter. The darker the image, the closer a feature is to the surface of the mica chip substrate surface.
Figure 20:
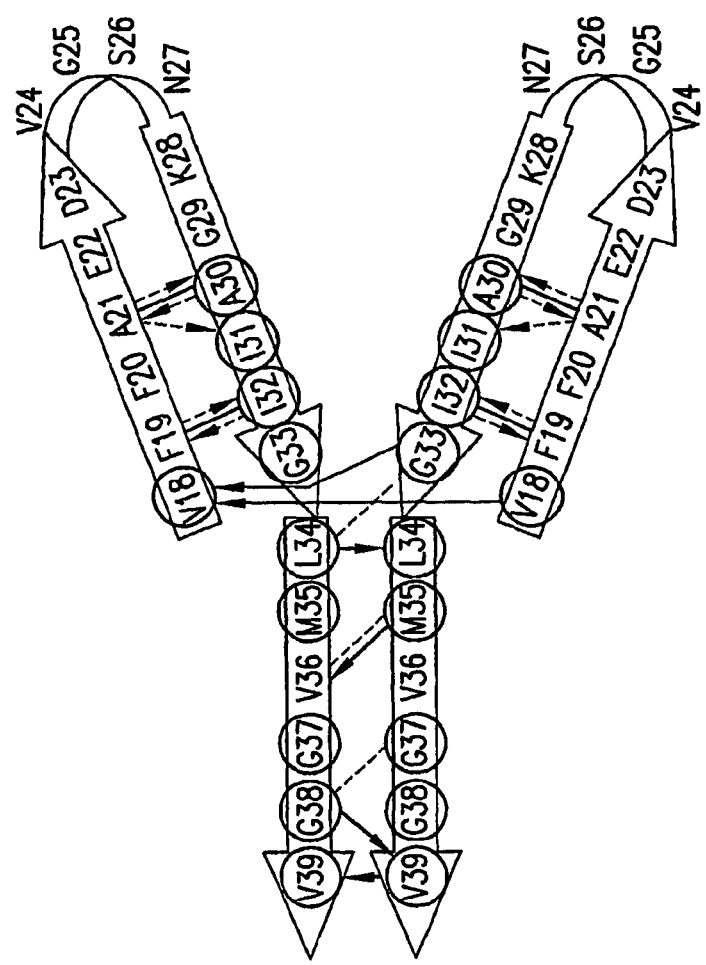
FIG. 20 summarizes the NMR data obtained on the N-Met Abeta 1-42 samples. The dashed lines indicate intermolecular NH—NH NOEs observed in a $^{15}N$-filtered and $^{15}N$-edited 3D NOESY experiment by using a mixed sample ([U-$^{15}N$,$^{2}H$]-labeled and [U-$^{14}N$,$^{2}H$]-labeled samples mixed at 1:1 ratio). The solid arrow lines indicate NOEs from NH to methyl groups (arrow heads) of the side chains observed in a $^{15}N$-resolved 3D NOESY experiment by using a mixed sample ([U-$^{15}N$,$^{2}H$]-labeled sample was mixed at 1:1 ratio with [U-$^{14}N$,$^{2}H$]-labeled sample that contains selectively $^{13}C$-labeled protonated methyl groups of IVL residues). The solid lines indicate intramolecular NH—NH NOEs observed in a $^{15}N$-resolved 3D NOESY experiment by using uniformly $^{15}N$-labeled sample with selectively $^{13}C$-labeled protonated methyl groups of Ile, Val, Leu residues in a $^{2}H$ background. The dashed arrow lines indicate intramolecular NOEs between the backbone amides and their sidechains observed in a $^{15}N$-resolved 3D NOESY experiment by using a [U-$^{15}N$]-labeled sample. The backbone amides that exhibit slow exchange in the NH/ND exchange experiments are indicated by circles. Figure discloses SEQ ID NOS 28 and 28, respectively.
Figure 21:
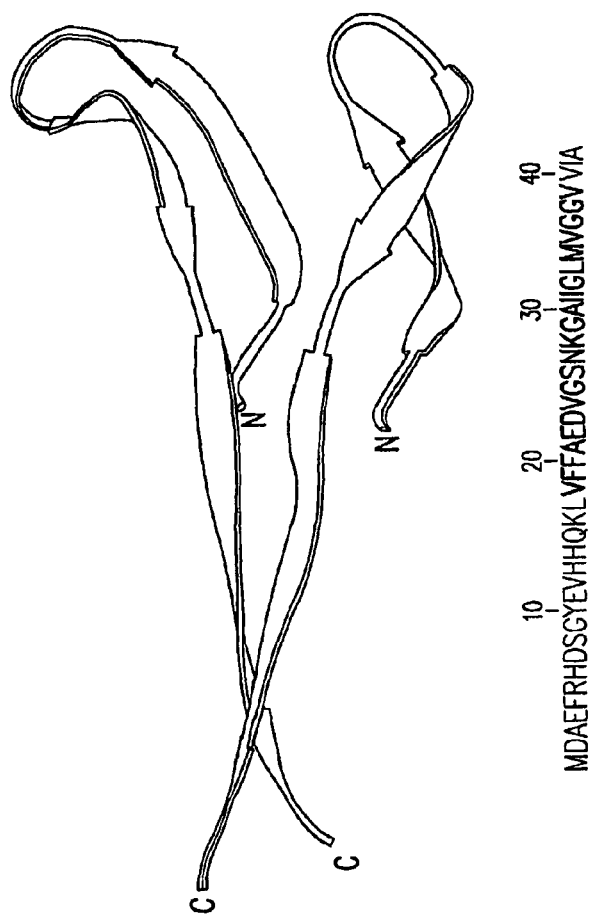
FIG. 21 depicts a structural model of the repeating unit of the N-Met-β-amyloid peptide 1-42 (SEQ ID NO: 6) consistent with the NMR data. Structures were calculated using a simulated annealing protocol with the program CNX (Brunger et al., Acta Crystallogr. D54 (Pt 5), 905-21 (1998)) and with the NOE-derived distance restraints from the analysis of the NMR data herein. The residues shown in ribbon plot correspond to the residues colored in black.
Figure 22:
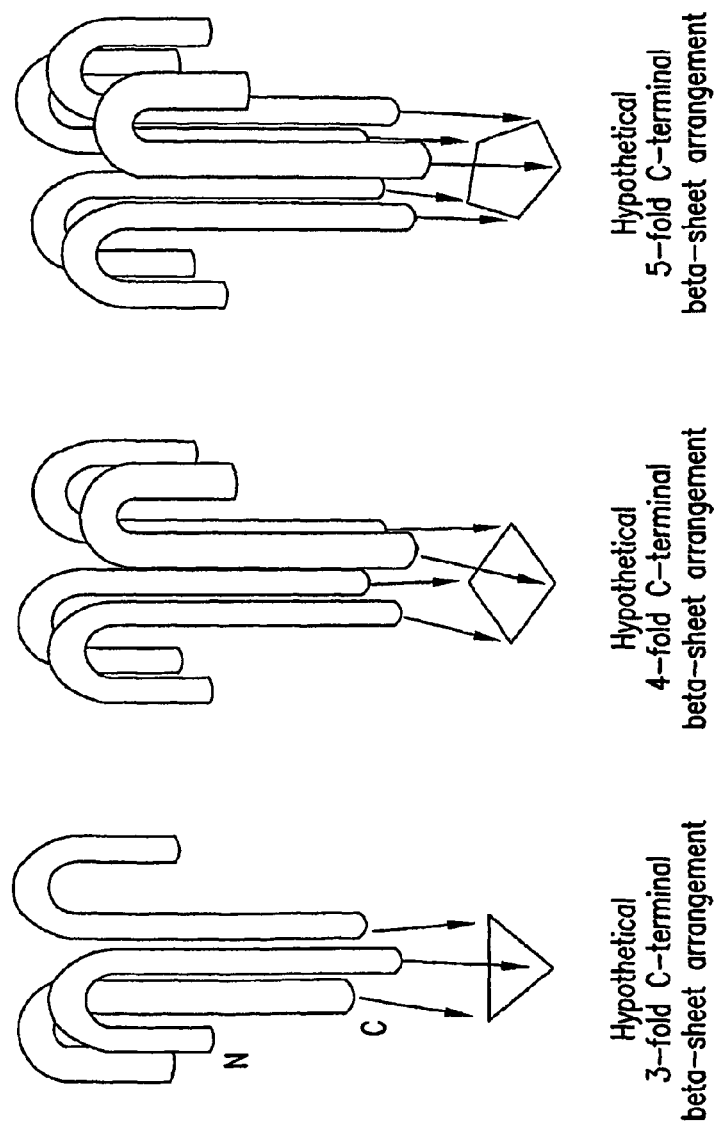
FIG. 22 depicts three "hypothetical" higher-order arrangements of amyloid peptide interactions in globulomers which could give rise to observed trimeric, tetrameric or pentameric intermediate forms in solution (FIG. 12, SDS gel). Higher-order aggregates also exist as described herein and are observed hydrodynamically. These arrangements are based on the presence of intermolecular interactions along the C-terminal parallel sheet region (see FIG. 20) as a driving force for intermolecular aggregation and eventual formation of fibrils of parallel amyloid peptide beta sheet. It is not meant to limit other potential arrangements of amyloid peptide or imply they do not exist.
Figure 23:
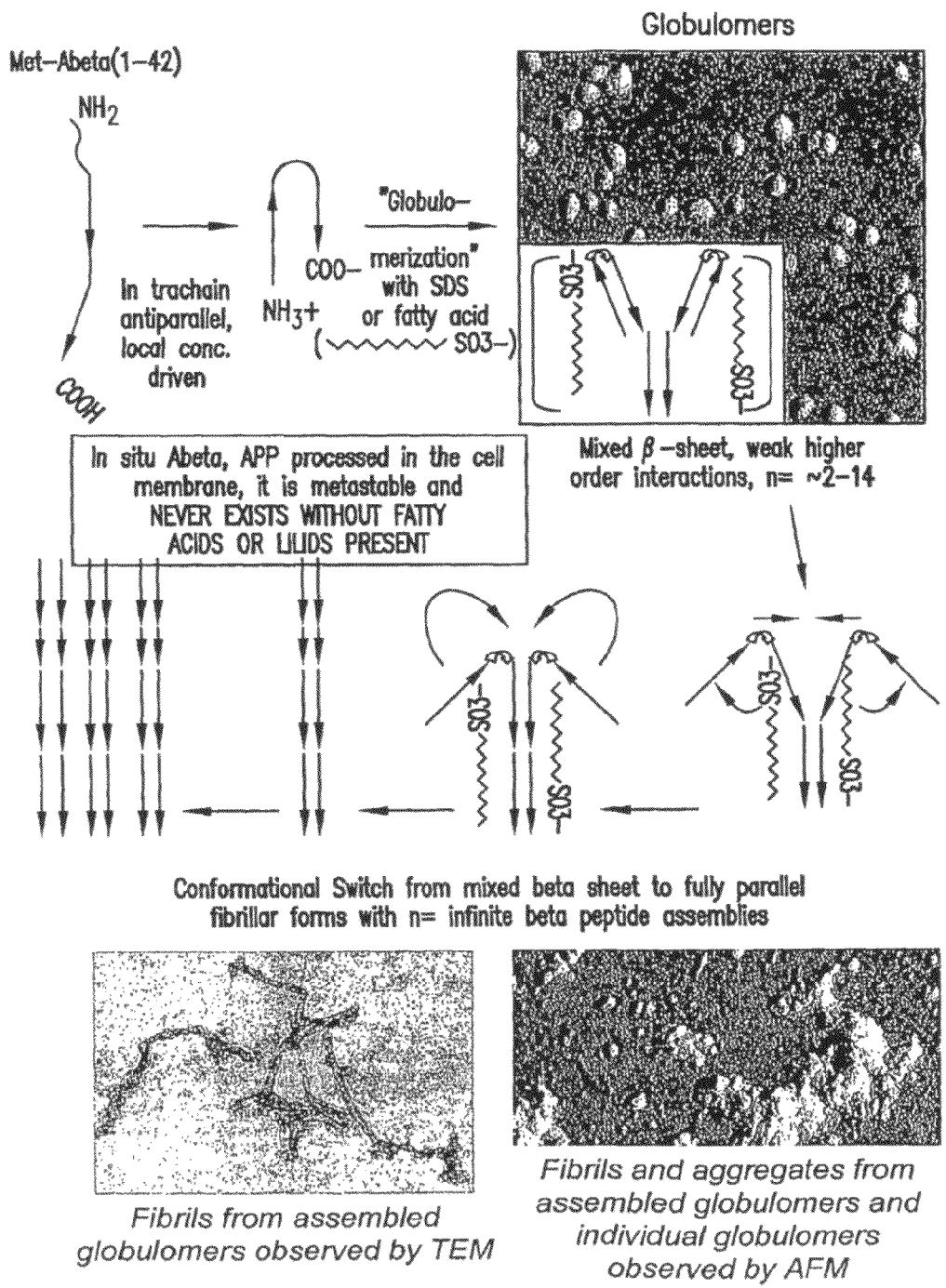
FIG. 23 depicts a representational diagram and atomic force and electron micrographs of Met-A-beta 1-42 samples supporting the amyloid conformational switch conversion from a mixture of intra-chain and inter-chain beta sheet interactions seen in vitro (see FIGS. 20 and 21). The globulomers are formed in the presence of SDS or fatty acids as described above and actually have SDS or fatty acids present therein, as described above. The SDS is depicted as indicated in the present figures. The precise orientations of the SDS surrounding the globulomer structures must still be elucidated. The switch occurs when the intra-chain anti-parallel beta-sheet interactions open and form a fully parallel sheet leading to accumulation of the amyloid fibrilar form. The resulting fibrillar and aggregated forms of the peptide produced after the anti-parallel region "opens" are observed in the AFM and TEM images in the figure. The lower TEM image depicts a representative slice, with dimensions y=~260 nm, x=~372 nm. The observed fibril width is 6 nm. The sample of purified Met1-42 globulomers was prepared as previously described. The Met1-42 was at a final concentration of 0.03 mg/mL and stained with 2% uranyl acetate for imaging at an amplification factor of 337,500× by transmission electron microscopy (TEM). The lower AFM image depicts a representative slice with dimensions y=250 nm, x=500 nm, The image shows the dispersed field of species observed. The sample of Met1-42 globulomers was prepared as previously described. The Met1-42 was at an initial concentration of 1.1 mg/mL incubated for 2+ weeks at 4 C, diluted 20:1 (0.055 mg/mL final) into nanopure water. 20 uL was deposited on a freshly cleaved mica chip and incubated for 5-8 min followed by 600 uL nanopure water rinse of mica chip and AFM scanning. Antibodies selective for globulomers bind selectively to epitopes created in the peptide with mixed intra-molecular anti-parallel beta sheet (approx. residues 18-33) and parallel beta sheet (approx. residues 34-39), as depicted in Figures X and Y. The mechanism or mechanisms leading to globulomer formation in vitro may differ from those observed in vivo.

Further, the methods allow one to prepare globulomers (see, e.g., International Application No. WO2004/067561; Barghorn et al, J. Neurochem. 2005 95, 834-847) for use in: 1) human immunization-based interventional therapies (e.g., globulomers may be used for active immunization); 2) human diagnostic testing or in animal-based surrogate biological testing systems (e.g., epitopes (i.e., globulomers or portions thereof) may be detected in human or animal models in order to diagnose disease or to determine palliative treatment); 3) large or small-scale screening for developing small-molecule (i.e., non-antibody or non-biologic) anti-Alzheimer's Disease preventative or therapeutic agents or in the prevention or treatment of neurological diseases related to Alzheimer's Disease which are characterized by cognitive impairment; 4) crystallographic or NMR-based structure-based design research for developing small-molecule anti-Alzheimer's Disease (or related disease) preventative or therapeutic agents; 5) crystallographic or NMR-based structure-based design research in developing antibody or other protein-based anti-Alzheimer's Disease (or related disease) preventative or therapeutic agents; and 6) preparation of globulomers for use in RNAi-based design research in developing anti-Alzheimer's Disease preventative or therapeutic agents. (For purposes of the present invention, a "globulomer" is defined as a biological structure that comprises small assemblies of non-covalently associated, individual amyloid peptides containing both parallel intermolecular beta-sheet and anti-parallel intra molecular beta sheet. The globulomer is meta-stable, soluble and its secondary structure is different from fibril-forming subunits (as above). With time it will eventually convert to fully parallel beta sheet fibrillar forms by the conformational "switch" pathway described (FIGS. 1B and 23). In particular, the observed secondary structures and possible three-dimensional and quaternary structures) for globulomeric interactions are as illustrated in FIGS. 20, 21 and 22 [see also coordinates in FIG. 18]. A globulomer is further distinguished from an oligomer in that the physical size of a globulomer is limited by its intra and intermolecular interactions; these lead to a highly limited form of an oligomer. The size of the globulomer is limited by the existence both of intermolecular interactions and intramolecular interactions within the globulomer assembly. It is composed of individual monomer-to-monomer parallel beta-sheet interactions with the unique secondary structure defined in accordance with the size ranges defined herein. It is expected that the much larger amyloid oligomers (fibrillar forms) preferentially comprise inter-chain parallel beta sheet secondary structures. These larger oligomers and fibrillar forms result from the kinetic opening of the amyloid "switch" structure (FIG. 23). By comparison, globulomers are preferentially characterized by being comprised of mixed inter-chain parallel and intra-chain anti-parallel structures as we have defined them.

The structure consists of at least two molecules as one repeating unit. The repeating unit contains two intra-molecular antiparallel β-sheets consisting of at least residues 19-21 and 30-32 of amyloid beta protein, and one inter-molecular parallel β-sheet consisting of at least residues 34-38 of amyloid beta protein (FIG. 21). The antiparallel β-sheet has a β-hairpin structure formed by two β-strands connected by a loop. The structure of this antiparallel β-sheet is defined by the cross-strand nuclear Overhauser effects (NOEs) between the backbone amides (indicated by solid lines) and between the backbone amides and their sidechains (indicated by dashed arrow lines)(FIG. 20)(see also Table 1 below) with distances between 1.8 and 6 angstroms.

TABLE 1

| Long-range NOEs Observed in the NOESY Spectra | |
|---|---|
| Long-range intramolecular NOEs | |
| F19 NH | I32 NH, HB, HG## |
| A21 NH | A30 NH, HB# |
| A21 NH | I31 HD1#, HG1# |
| I32 NH | F19 HD#, HB# |
| A30 NH | A21 HB# |
| Long-range intermolecular NOEs | |
| G33 NH | G34 NH |
| M35 NH | V36 NH |
| G37 NH | G38 NH |
| G33 NH | V18 C$_\gamma$H$_3$ |
| V18 NH | V18 C$_\gamma$H$_3$ |
| L34 NH | L34 C$_\delta$H$_3$ |
| M35 NH | V36 C$_\gamma$H$_3$ |
| G38 NH | V39 C$_\gamma$H$_3$ |
| V39 NH | V39 C$_\gamma$H$_3$ |

The in-register parallel β-sheet is defined by intermolecular NOEs between backbone NH—NH (indicated by dashed lines) and between backbone NH and methyl groups of the side chains (indicated by solid arrow lines)(FIG. 20).

The intra- vs. inter-molecular NOEs were distinguished using different isotope-labeled samples. The following samples were prepared: (Sample A) Uniformly [$^{15}$N]-labeled protonated sample; (Sample B) Uniformly [$^{15}$N]-labeled sample with selectively $^{13}$C-labeled protonated methyl groups of Ile, val, Leu residues in a $^2$H background; (Sample C) A mixed sample in which one molecule is labeled with [U-$^{15}$N,$^2$H] and another is labeled with [U-$^{14}$N,$^2$H] that were mixed at 1:1 ratio; (Sample D) A mixed sample in which a [U-$^{15}$N,$^2$H]-labeled peptide was mixed at 1:1 ratio with a [U-$^{14}$N,$^2$H]-labeled peptide that contains selectively $^{13}$C-labeled protonated methyl groups of IVL residues. The intra-molecular NH—NH NOEs indicated by solid lines (FIG. 20) were observed in the samples A and B in 3D $^{15}$N-resolved NOESY spectra, but not in the sample C in a $^{15}$N-filtered and $^{15}$N-edited 3D NOESY spectrum. Additional intra-molecule NOEs between the backbone amides and their sidechains were observed as indicated by the dashed arrow lines (FIG. 20) in a $^{15}$N-resolved 3D NOESY by using the sample A. These NOE data again indicate the presence of the antiparallel β-sheet structure. The inter-molecular NH—NH NOEs indicated by dashed lines (FIG. 20) were observed in the sample C in a $^{15}$N-filtered and $^{15}$N-edited 3D NOESY spectrum. These NOEs unequivocally establish the in-register parallel intermolecular β-sheet. Additional inter-molecular NOEs between the backbone amide $^{15}$NH on one molecule and $^{13}$CH$_3$ methyl groups on another molecule were observed as indicated by the solid arrow lines (FIG. 20) in the sample D in the $^{15}$N-resolved $^1$H/$^1$H and $^{13}$C/$^1$H NOESY spectra. These intermolecular NOEs again indicate an in-register parallel β-sheet structure compatible with phi (φ) angles −120±50 and psi (T) angles 140±50. From an NH/ND exchange experiment in which the aqueous $^{15}$N-labeled sample was lyophilized and dissolved in $D_2O$, amides protected from exchange in the β-sheet are obtained for the sample in $D_2O$ for at least 20 min. The protected amides are indicated by circles on the residue (FIG. 20). These slowly exchanging amides are mostly located in the β-sheets and are likely hydrogen-bonded.

Using the NOE-derived distance restraints from the analysis of the NMR data (see Table 1), structures were calculated with the program CNX [A. T. Brunger, et al., Acta Crystallogr. D54 (Pt 5), 905-21, (1998)] by using a simulated annealing protocol [M. Nilges, et al., FEBS Lett. 229, 317-324, (1988)]. G33 is located at the junction between the antiparallel and parallel β-sheets. The conformation of this residue is not defined and may have any phi, psi angle compatible with any physically allowed conformation. A representative conformation of this entity, which is perhaps a dimer, is shown in FIG. 21, and its coordinates are given in FIG. 24.

It should be noted that the complete structural coordinates of one of the structures of amyloid beta entities of the present invention includes those set forth in FIG. 24 as well as +/− a root mean square deviation from the conserved backbone atoms of the amino acids (or conservative substitutions thereof).

The root mean square deviation for the parallel β-sheet amino acid residues 34-38 of the twenty computationally most favorable structures about the mean coordinate positions is 0.51±0.29 angstroms for the backbone atoms (Cα, N, and C') and 1.04±0.36 angstroms for all heavy atoms Less favorable mean coordinate positions would be 0.51±1.29 angstroms for the backbone atoms (Cα, N, and C') and 1.04±0.36 angstroms for all heavy atoms. Least favorable mean coordinate positions would be 0.51±2.29 angstroms for the backbone atoms (Cα, N, and C') and 1.04±2.36 angstroms for all heavy atoms.

The root mean square deviation for the antiparallel β-sheet amino acid residues 19-21 and 30-32 of the twenty computationally most favorable structures about the mean coordinate positions is 0.67±0.23 angstroms for the backbone atoms (Cα, N, and C') and 1.52±0.36 angstroms for all heavy atoms. Less favorable mean coordinate positions would be 0.67±1.23 angstroms for the backbone atoms (Cα, N, and C') and 1.52±1.36 angstroms for all heavy atoms. Least favorable mean coordinate positions would be 0.67±2.23 angstroms for the backbone atoms (Cα, N, and C') and 1.52±2.36 angstroms for all heavy atoms.

The above root mean square deviations (rmsd) are experimentally determined numbers. Since the orientation between the parallel β-sheet and antiparallel β-sheet is not defined, rmsd for the entire structure coordinates are not determined at present. ("Root mean square deviation" is the square root of the arithmetic mean of the coordinates of the deviations from the mean and is a manner of expressing deviation or variation from the structural coordinates described herein.)

Further, molecular modeling methods known in the art may be used to identify one or more active sites or binding pockets of the amyloid beta molecule (e.g., dimer) described herein. Specifically, the structural coordinates are used to characterize a three dimensional model as shown in FIG. 21. Then, from the model, putative active sites may be computationally visualized, identified and characterized based upon, for example, the surface structure of the molecule, surface charge, steric arrangement, the presence of reactive amino acids and regions of hydrophobicity and hydrophilicity. Such putative active sites may then be further refined using chemical shift perturbations of spectra generated from various amyloid beta complexes, competitive and non-competitive inhibition experiments, and/or by the generative and characterization of amyloid beta mutants to identify critical resides or characteristics of the active site(s). (See U.S. Pat. No. 6,934,639.)

An agent that interacts or associates with the active site(s) may be identified by determining from a three dimensional model of the amyloid beta molecule, and performing computer fitting analysis. Computer fitting analyses utilize various computer software programs that evaluate the "fit" between the putative active site(s) and the identified agent by: 1) generating a three dimensional model of the putative active site(s) using homology modeling or the structural coordinates of the active site(s) and 2) determining the degree of association between the putative active site(s) and the identified agent. The degree of association may be determined computationally or experimentally using binding assays.

Additionally, it should be noted that the proteins, globulomers and oligomers of the present invention (as well as antibodies directed thereto), may be used in a variety of diagnostic assays.

In one embodiment of the present invention, the protein, globulomer or oligomer, or a portion thereof, is coated on a solid phase (or is present in a liquid phase). The test or biological sample (e.g., whole blood, cerebrospinal fluid, serum, etc.) is then contacted with the solid phase. If antibodies are present in the sample, such antibodies bind to the antigen on the solid phase and are then detected by either a direct or indirect method. The direct method comprises simply detecting presence of the complex itself and thus presence of the antibodies. In the indirect method, a conjugate is added to the bound antibody. The conjugate comprises a second antibody, which binds to the first bound antibody, attached to a signal-generating compound or label. Should the second antibody bind to a bound first antibody, the signal-generating compound generates a measurable signal. Such signal then indicates presence of the first antibody in the test sample.

Examples of solid phases used in diagnostic immunoassays are porous and non-porous materials, latex particles, magnetic particles, microparticles (see U.S. Pat. No. 5,705, 330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3M, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, whole blood, dried whole blood, serum, cerebrospinal fluid or aqueous or organo-aqueous extracts of tissues and cells.

In another embodiment of the present invention, the test sample may be exposed to a solid phase (or liquid phase) coated with specific antibodies of the present invention (e.g., human or humanized monoclonal antibodies, polyclonal antibodies, etc.). Globulomers, oligomers or protein, as described above and if present in the sample, bind to the solid phase and may then be detected by a direct or indirect method as described above. More specifically, the indirect method involves the addition of a conjugate comprising a second antibody (which binds to the bound antigen) attached to a label or signal-generating compound. When the second antibody binds to the bound antigen, a detectable signal is then generated indicating presence of an Alzheimer's protein such as a globulomer, oligomer, peptide, or portion thereof, in the test sample.

The present invention also encompasses a third method for detecting the presence of antibodies in a test sample. This method comprises the steps of: (a) contacting the test sample suspected of containing the antibodies with anti-antibody specific for the antigen (e.g., protein, globulomer or oligomer, or a portion thereof), under time and conditions sufficient to allow the formation of anti-antibody/antigen complexes; (b) adding antigen to the resulting anti-antibody/antigen complexes for a time and under conditions sufficient to allow the antigen to bind to the bound antibody, the antigen comprising a protein, globulomer, oligomer, or portion thereof, as defined herein; and (c) adding a conjugate to the resulting anti-antibody/antibody/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the antibodies which may be present in the test sample by detecting the signal generated by the signal generating compound. A control or calibrator may be used which comprises antibody to the anti-antibody.

The present invention also includes a vaccine comprising one of more of the antigens defined herein (i.e., protein, oligomer, globulomer, or a portion thereof) and a pharmaceutically acceptable adjuvant (e.g., Freund's adjuvant or phosphate buffered saline).

Kits are also included within the scope of the present invention. More specifically, the present invention includes kits for determining the presence of antibodies in a patient. In particular, a kit for determining the presence of antibodies in a test sample comprises a) an antigen as defined herein (e.g., protein, globulomer, oligomer, or portion thereof; and b) a conjugate comprising an antibody attached to a signal generating compound capable of generating a detectable signal. The kit may also contain a control or calibrator which comprises a reagent which binds to the antigen.

The present invention also includes another type of kit for detecting antibodies in a test sample. The kit may comprise a) an anti-antibody specific for the antibody of interest, and b) an antigen or portion thereof as defined above. A control or calibrator comprising a reagent which binds to the antigen may also be included. More specifically, the kit may comprise a) an anti-antibody specific for the antibody and b) a conjugate comprising the antigen, the conjugate being attached to a signal generating compound capable of generating a detectable signal. Again, the kit may also comprise a control of calibrator comprising a reagent which binds to the antigen.

The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

Additionally, the present invention includes a humanized antibody created against and using an antigen selected from the group consisting of: the Arctic (E693G) mutation, the Dutch (E693Q) mutation, the Italian mutation (E693K), the Iowa (D694N) mutation and the Flemish (A692G) mutation. This antibody may recognize the native, human sequence of amyloid beta peptide and at least one of the mutated sequences. This antibody may be administered to a patient identified as having such a mutation for purposes of therapy. This antibody may have a dual variable domain and may recognize the native, human amyloid beta sequence and at least one of the familial mutants as described above. This antibody may also be dual specific.

Additionally, the present invention includes a method of detecting a mutant amyloid beta peptide sequence in a patient suspected of having Alzheimer's Disease. This method comprises the steps of: a) isolating a biological sample from the patient; b) contacting said biological sample with the antibody described directly above for a time and under conditions sufficient for the formation of mutant antigen/antibody complexes; and c) detecting presence of the mutant antigen/antibody complexes, said complexes indicating said patient has a mutant amyloid beta peptide sequence and consequently Alzheimer's Disease.

Further, the present invention includes an isolated globulomer comprising approximately at least 0.5-2.0 moles of sodium dodecyl sulfate (SDS) or a fatty acid per mole of amyloid peptide. Most preferably, approximately 1.0 mole of SDS is present in the globulomer. The present invention also includes an epitope of the isolated globulomer. (The epitope may be formed by a mixture of the peptide and the SDS (or fatty acid). Further, the present invention also includes an isolated antibody which binds to the epitope. This antibody may also block formation of amyloid beta peptide aggregates. Blockage may occur at the stage of a peptide dimer, a peptide trimer, a peptide tetramer, a peptide pentamer, a peptide hexamer, a peptide heptamer, a peptide octamer, a peptide nonamer, a peptide decamer, a peptide undecamer, a peptide dodecamer, a peptide tridecamer and a peptide tetradecamer.

Also, the present invention also includes an isolated globulomer comprising an amyloid beta peptide. This peptide comprises an amino acid sequence having a mutation selected from the group consisting of: the Arctic (E693G) mutation, the Dutch (E693Q) mutation, the Italian mutation (E693K), the Iowa (D694N) mutation and the Flemish (A692G) mutation. The invention also includes an epitope of this globulomer (i.e., an epitope formed by the mixture of peptide and SDS (or fatty acid) and the globulomer but is immunologically distinct from the immunoreactive epitope of a native, human amyloid beta peptide sequence.

Moreover, the present invention includes an isolated antibody (e.g., monoclonal antibody) which preferentially binds to the epitope described above compared to an epitope of the native, human amyloid peptide. Such an antibody may also be used in the treatment of a patient with familial Alzheimer's Disease.

The present invention also encompasses an isolated antibody (e.g., monoclonal antibody) which may be used in the treatment of familial forms of Alzheimer's Disease (as described above) and has preferential and selective epitope reactivity in connection with the epitope of the familial mutant (which is distinct from epitopes presented during the treatment of sporadic Alzheimer's Disease).

Additionally, the present invention includes a method of preventing or treating Alzheimer's Disease in a patient needing the prevention or treatment comprising the step of administering any one or more of the isolated antibodies described above to the patient in an amount sufficient to effect the prevention or treatment.

Further, the present invention includes an isolated globulomer comprising an amyloid beta peptide. The peptide comprises amino acids which exhibit approximately 33% or less protection or exchange based upon hydrogen-deuterium exchange behavior, wherein the amino acids are selected from the group consisting of: 2(Asp), 3(Ala), 4(Glu), 5(Phe), 7(His), 8(asp), 9(Ser), 10(Gly), 17(Lys), (Phe), 21(Phe), 22(Ala), 25(Val), 26(Gly), 29(Lys) and 30(Gly). The isolated globulomer comprises an amyloid beta peptide.

Moreover, the present invention includes an isolated globulomer comprising an amyloid beta peptide. The peptide comprises amino acids which exhibit approximately 33% to approximately 66% protection or exchange based upon hydrogen-deuterium exchange behavior, wherein said amino acids are selected from the group consisting of: 16(Gln), 31(Ala), 32(Ile), 42(Ile) and 43(Ala).

Also, the present invention encompasses an isolated globulomer comprising an amyloid beta peptide. The peptide comprises amino acids which exhibit approximately 66% or more protection or exchange based upon hydrogen-deuterium exchange behavior, wherein the amino acids are selected form the group consisting of: 12(Glu) 18(Leu), 19(Val), 24(Asp), 33(Ile), 34(Gly), 35(Leu), 36(Met) 38 (Gly), 39 (Gly) and 40 (Val).

Human Familial Mutants

Figure 27:
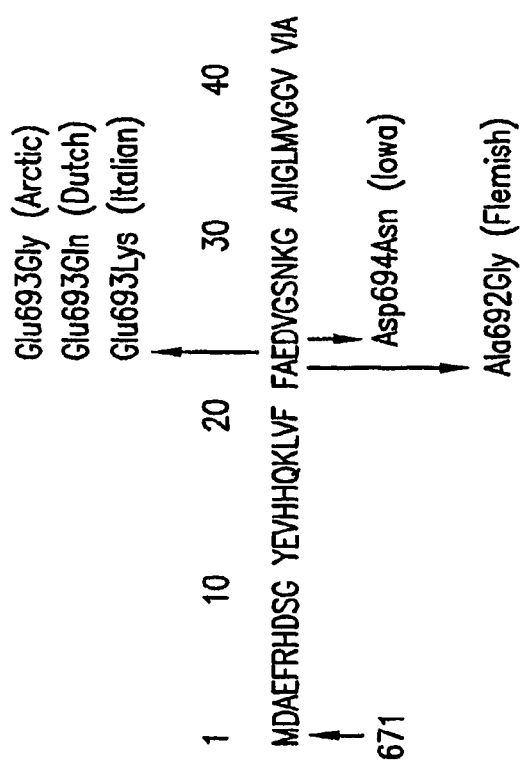
FIG. 27 illustrates the human familial mutant Alzheimer peptides expressed as their N-terminal Met forms. Figure discloses SEQ ID NO: 6.

The human familial mutant Alzheimer peptides expressed as their N-terminal Met forms as seen in FIG. 27 are envisioned to have differential (lower) reactivity with antibodies generated against the native sequence globulomer form. For example the ability to bind to antibody A, generated using the native sequence globulomer, will be reduced for the following familial mutations: Arctic (E693G), Dutch (E693Q), Italian (E693K), Iowa (D694N) and Flemish (A692G). This lessened ability to bind to the mutant globulomeric forms results from the altered sequence/structure in this region of the antibody A epitope. Use of humanized forms of antibodies in therapeutic treatment of patients suffering from familial forms of Alzheimer's Disease related to these mutations will require antibodies selectively developed to the globulomeric epitopes containing the sequences of these regions. The antibody A-like antibodies by themselves will not be therapeutically active for these familial mutants, as they will exhibit a reduced ability to recognize the familial epitope presented in the globulomers in vivo.

The present invention may be illustrated by use of the following non-limiting examples:

EXAMPLE I

Cloning of Abeta-Amyloid Peptide

The Abeta-amyloid peptide was synthetically constructed. In particular, FIG. 1 illustrates the DNA sequence encoding the peptide described herein as well as the amino acid sequence of the peptide. Primers that cover the sequence which codify Abeta-amyloid peptide and the desired restriction sites to clone it (see Table 2 below) on the vector pET29 were designed and used on an annealing reaction to generate the fragment that was used on a ligation reaction to the desired E. coli expression vector.

After annealing those oligos together, they were incorporated into pET29 NdeI XhoI sites by ligation using DNA ligase (Invitrogen, Carlsbad, Calif.) to form pET29-ABeta amyloid peptide [1-42] native form. The final construct was confirmed by DNA sequencing.

Beta amyloid peptides [1-39, 40, 42 and 43] were made by site directed mutagenesis (SDM) using as template pET29-ABeta amyloid peptide [1-42]. Pairs of primers SDMamy-39s and as, SDMamy-40s and as, SDMamy-41s and as, SDMamy-43s and as (see Table 2) were employed in independent SDM reactions using the Quick-Change kit (Stratagene, La Jolla, Calif.). The new constructs pET29-Aβ amyloid peptide [1-39], pET29-ABeta amyloid peptide [1-40], pET29-ABeta amyloid peptide [1-41] and pET29-ABeta amyloid peptide [1-43] were confirmed by DNA sequencing.

The resulting constructs were used to transform E. coli BL21 (DE3) to test expression. Expression of the peptide was performed through growths at 37° C. for 4 hr after induction with 1 mM IPTG (Isopropyl-beta-D-thiogalactopyraoside). The insoluble fraction from the test expression yielded a protein of the expected size, as visualized on a Coomassie-stained SDS protein gel.

TABLE 2

A.

| amy-1 | TATGGATGCGGAATTTCGCCATGATAGCGGCTATGAAG | (SEQ ID NO: 11) |
| --- | --- | --- |
| amy-2 | TGCATCATCAGAAACTGGTGTTTTCGCGGAAGATGTGGGCAGCAACAAA | (SEQ ID NO: 12) |
| amy-3 | GGCGCGATTA TTGGCCTGAT GGTGGGTGGT GTGGTGATTG CGTGAC | (SEQ ID NO: 13) |
| amy-4 | CACCAGTTTCTGATGATGCACTTCATAGCCGCTATCATGGCGAAATTCCGCATCCA | (SEQ ID NO NO: 14) |
| amy-5 | ATCAGGCCAATAATCGCGCCTTTGTTGCTGCCCACATCTTCCGCGAAAAA | (SEQ ID NO: 15) |
| amy-6 | TCGAGTCACGCAATCACCACACCACCCACC | (SEQ ID NO: 16) |

B.

| SDMamy-43 (+) | GGGTGGTGTGGTGATTGCGACCTGACTCGAGCACCACCACC | (SEQ ID NO: 17) |
| --- | --- | --- |
| SDMamy-43 (−) | GGTGGTGGTGCTCGAGTCAGGTCGCAATCACCACACCACCC | (SEQ ID NO: 18) |
| SDMamy-41 (+) | GGTGGGTGGTGTGGTGATTTGACTCGAGCACCACCACC | (SEQ ID NO: 19) |
| SDMamy-41 (−) | GGTGGTGGTGCTCGAGTCAAATCACCACACCACCCACC | (SEQ ID NO: 20) |
| SDMamy-40 (+) | GATGGTGGGTGGTGTGGTGTGACTCGAGCACCACCACC | (SEQ ID NO: 21) |

TABLE 2-continued

| | | |
|---|---|---|
| SDMamy-40 (−) | GGTGGTGGTGCTCGAGTCACACCACACCACCCACCATC | (SEQ ID NO: 22) |
| SDMamy-39 (+) | CCTGATGGTGGGTGGTGTGTGACTCGAGCACCACC | (SEQ ID NO: 23) |
| SDMamy-39 (−) | GGTGGTGCTCGAGTCACACACCACCCACCATCAGG | (SEQ ID NO: 24) |

Part A contains the nucleotide sequence of the primers used to synthesize Aβ amyloid peptide [1-42]. Part B contains the nucleotide sequence of the primers used on the SDM reactions to modify pET29-Aβ amyloid peptide [1-42] and made pET29-Aβ amyloid peptide [1-39], [1-40], [1-41], and [1-43].

EXAMPLE II

Fermentation and Expression of Beta-Amyloid

1) A-beta (1-39):
[Production of Unlabelled Material]

The expression plasmid was transformed into *E. coli* BL21 (DE3) and plated on LB supplemented with kanamycin (50 mg/L). After incubating at 37° C. overnight, a transformant arising on the plate was used to inoculate a 150 mL M9 preculture supplemented with kanamycin at 50 mg/L. The preculture was placed on an orbital shaker (185 rpm) and incubated at 30° C. When the culture reached an $OD_{600nm}$ of 0.468, the entire preculture was transferred to a New Brunswick Scientific (Edison, N.J.) Micros fermenter containing 18 L of media. The fermenter media consisted of (per L) 11.32 g $Na_2HPO_4$*$7H_2O$, 3 g $KH_2PO_4$, 0.5 g NaCl, 1 mL 1% DF-60 antifoam, 1.5 g $NH_4Cl$, 3.55 g glucose, 2 mL 1M $MgSO_4$, 0.1 mL 1N $CaCl_2$, 0.02 mL $FeSO_4$ (40 mg/mL), 2 mL kanamycin (25 mg/mL), and 0.633 mL trace element solution [per L in 5N HCl: 10 g $MnSO_4H_2O$; 10 g $AlCl_3H2O$; 4 g $CoCl_2$; 2 g $ZnSO_4$ $7H_2O$; 2 g $Na_2MoO_4$ $2H_2O$; 1 g $CuCl_2$ $2H_2O$; 0.5 g $H_3BO_4$]. The temperature was initially controlled at 30.0° C. Air was sparged into the fermenter at 2 vvm, and the dissolved oxygen concentration [$DO_2$] was maintained at greater than 45% air saturation through a cascaded control loop that increased the agitation speed when the $DO_2$ concentration dropped below 45%. The pH was controlled at 7.0 during the run through automatic addition of $4NH_2SO_4$ and 4N KOH. At an $OD_{600nm}$ of 2.0, the temperature set-point was changed to 41° C., and expression of A-beta was induced via addition of 1 mM IPTG. The glucose concentration was maintained above 0 g/L during the entire expression phase through feeding of a 30% glucose solution. Cells were harvested 3 h post-induction.

2) A-beta (1-40).
[Production of $^{15}$N-Labelled Material]

The expression plasmid was transformed into *E. coli* BL21 (DE3) and plated on LB supplemented with kanamycin (50 mg/L). After incubating at 37° C. overnight, a transformant arising on the plate was used to inoculate a 150 mL $^{15}$N-M9 preculture supplemented with kanamycin at 50 mg/L. The preculture was placed on an orbital shaker (185 rpm) and incubated at 30° C. When the culture reached an $OD_{600nm}$ of 0.510, 75 mL of preculture was transferred to a New Brunswick Scientific (Edison, N.J.) Micros fermenter containing 18 L of media. The fermenter media consisted of (per L): 11.32 g $Na_2HPO_4.7H_2O$, 3 g $KH_2PO_4$, 0.5 g NaCl, 1 mL 1% DF-60 antifoam, 1.5 g $^{15}$N—$NH_4Cl$, 3.55 g glucose, 2 mL 1M $MgSO_4$, 0.1 mL 1M $CaCl_2$, 0.02 mL $FeSO_4$ (40 mg/mL), 2 mL kanamycin (25 mg/mL), and 0.633 mL trace element solution [per L in 5N HCl: 10 g $MnSO_4H_2O$; 10 g $AlCl_3H_2O$; 4 g $CoCl_2$; 2 g $ZnSO_4$ $7H_2O$; 2 g $Na_2MoO_4$ $2H_2O$; 1 g $CuCl_2$ $2H_2O$; 0-5 g $H_3BO_4$]. The temperature was initially controlled at 30.0° C. Air was sparged into the fermenter at 2 vvm, and the dissolved oxygen concentration [$DO_2$] was maintained at greater than 45% air saturation through a cascaded control loop which increased the agitation speed when the $DO_2$ concentration dropped below 45%. The pH was controlled a 7.0 during the run through automatic addition of $4N H_2SO_4$ and 4N KOH. At an $OD_{600nm}$ of 1.5, the temperature set-point was changed to 41° C. and expression of A-beta was induced via addition of 1 mM IPTG. The glucose concentration was maintained above 0 g/L during the entire expression phase through feeding of a 30% glucose solution. Cells were harvested 3 h post-induction.

3) A-beta (1-41):
[Production of $^{15}$N-Labelled Material]

The expression plasmid was transformed into *E. coli* BL21 (DE3) and plated on LB supplemented with kanamycin (50 mg/L). After incubating at 37° C. overnight, a transformant arising on the plate was used to inoculate a 150 mL $^{15}$N-M9 preculture supplemented with kanamycin at 50 mg/L. The preculture was placed on an orbital shaker (185 rpm) and incubated at 30° C. When the culture reached an $OD_{600nm}$ of 0.424, the entire preculture was transferred to a New Brunswick Scientific (Edison, N.J.) Micros fermenter containing 18 L of media. The fermenter media consisted of (per L): 11.32 g $Na_2HPO_4. 7H_2O$, 3 g $KH_2PO_4$, 0.5 g NaCl, 1 mL 1% DF-60 antifoam, 1.5 g $^{15}$N—$NH_4Cl$, 3.55 g glucose, 2 mL 1M $MgSO_4$, 0.1 mL 1M $CaCl_2$, 0.02 mL $FeSO_4$ (40 mg/mL), 2 mL kanamycin (25 mg/mL), and 0.633 mL trace element solution [per L in 5N HCl: 10 g $MnSO_4H_2O$; 10 g $AlCl_3H2O$; 4 g $CoCl_2$; 2 g $ZnSO_4$ $7H_2O$; 2 g $Na_2MoO_4$ $2H_2O$; 1 g $CuCl_2$ $2H_2O$; 0.5 g $H_3BO_4$]. The temperature was initially controlled at 30.0° C. Air was sparged into the fermenter at 2 vvm, and the dissolved oxygen concentration [$DO_2$] was maintained at greater than 45% air saturation through a cascaded control loop which increased the agitation speed when the $DO_2$ concentration dropped below 45%. The pH was controlled at 7.0 during the run through automatic addition of $4N H_2SO_4$ and 4N KOH. At an $OD_{600nm}$ of 1.8, the temperature setpoint was changed to 41° C. and expression of A-beta was induced via addition of 1 mM IPTG. The glucose concentration was maintained above 0 g/L during the entire expression phase through feeding of a 30% glucose solution. Cells were harvested 3 h post-induction.

4) A-beta (1-42):
[Production of $^{15}$N-Labelled Material]

The expression plasmid was transformed into *E. coli* BL21 (DE3) and plated on LB supplemented with kanamycin (50 mg/L). After incubating at 37° C. overnight, a transformant arising on the plate was used to inoculate a 150 mL $^{15}$N-M9 preculture supplemented with kanamycin at 50 mg/L. The preculture was placed on an orbital shaker (185 rpm) and incubated at 30° C. When the culture reached an $OD_{600nm}$ of 0.520, 75 mL of preculture was transferred to a New Brunswick Scientific (Edison, N.J.) Micros fermenter containing 18 L of media. The fermenter media consisted of (per L): 11.32 g $Na_2HPO_4$*$7H_2O$, 3 g $KH_2PO_4$, 0.5 g NaCl, 1 mL 1% DF-60 antifoam, 1.5 g $N^{15}$—$NH_4Cl$, 3.55 g glucose, 2 mL 1M $MgSO_4$, 0.1 mL 1M $CaCl_2$, 0.02 mL $FeSO_4$ (40 mg/mL), 2 mL kanamycin (25 mg/mL), and 0.633 mL trace element solution [per L in 5N HCl: 10 g $MnSO_4H_2O$; 10 g $AlCl_3H_2O$; 4 g $CoCl_2$; 2 g $ZnSO_4$ $7H_2O$; 2 g $Na_2MoO_4$ $2H_2O$; 1 g $CuCl_2$ $2H_2O$; 0.5 g $H_3BO_4$]. The temperature was initially controlled at 30.0° C. Air was sparged into the fermenter at 2 vvm, and the dissolved oxygen concentration [$DO_2$] was maintained at greater than 45% air saturation through a cascaded control loop which increased the agitation speed when the $DO_2$ concentration dropped below 45%. The pH was controlled at 7.0 during the run through automatic addition of 4N $H_2SO_4$ and 4N KOH. At an $OD_{600nm}$ of 1.5, the temperature setpoint was changed to 41° C. and expression of A-beta was induced via addition of 1 mM IPTG. The glucose concentration was maintained above 0 g/L during the entire expression phase through feeding of a 30% glucose solution. Cells were harvested 3 h post-induction.

5) A-beta (1-42):
[Production of Unlabelled Material]

The expression plasmid was transformed into *B. coli* BL21 (DE3) and plated on LB supplemented with kanamycin (50 mg/L). After incubating at 37° C. overnight, transformants arising on the plate were used to inoculate six fernbach flasks containing 1 L of Terrific Broth (Sigma-Aldrich, St, Louis, Mo.) supplemented with kanamycin (50 mg/L). The flasks were transferred to an orbital shaker (185 rpm) at 30° C. When the culture $OD_{600nm}$ reached 0.45, expression of A-beta was induced by addition of 1 mM IPTG, and the flasks were transferred to an orbital shaker at 41° C. Cells were harvested 3 h post-induction.

6) A-beta (1-43):
[Production of Unlabelled Material]

The expression plasmid was transformed into *E. coli* BL21 (DE3) and plated on LB supplemented with kanamycin (50 mg/L). After incubating at 37° C. overnight, transformants arising on the plate were used to inoculate 14 fernbach flasks containing 1 L of Terrific Broth (Sigma-Aldrich, St. Louis, Mo.) supplemented with kanamycin (50 mg/L). The flasks were transferred to an orbital shaker (185 rpm) at 37° C. When the culture $OD_{600nm}$ reached 0.44, expression of A-beta was induced by addition of 1 mM IPTG, and the flasks were transferred to an orbital shaker at 41° C. Cells were harvested 3 h post-induction.

EXAMPLE III

Purification of Recombinantly Expressed Beta-Amyloids

Figure 3B:
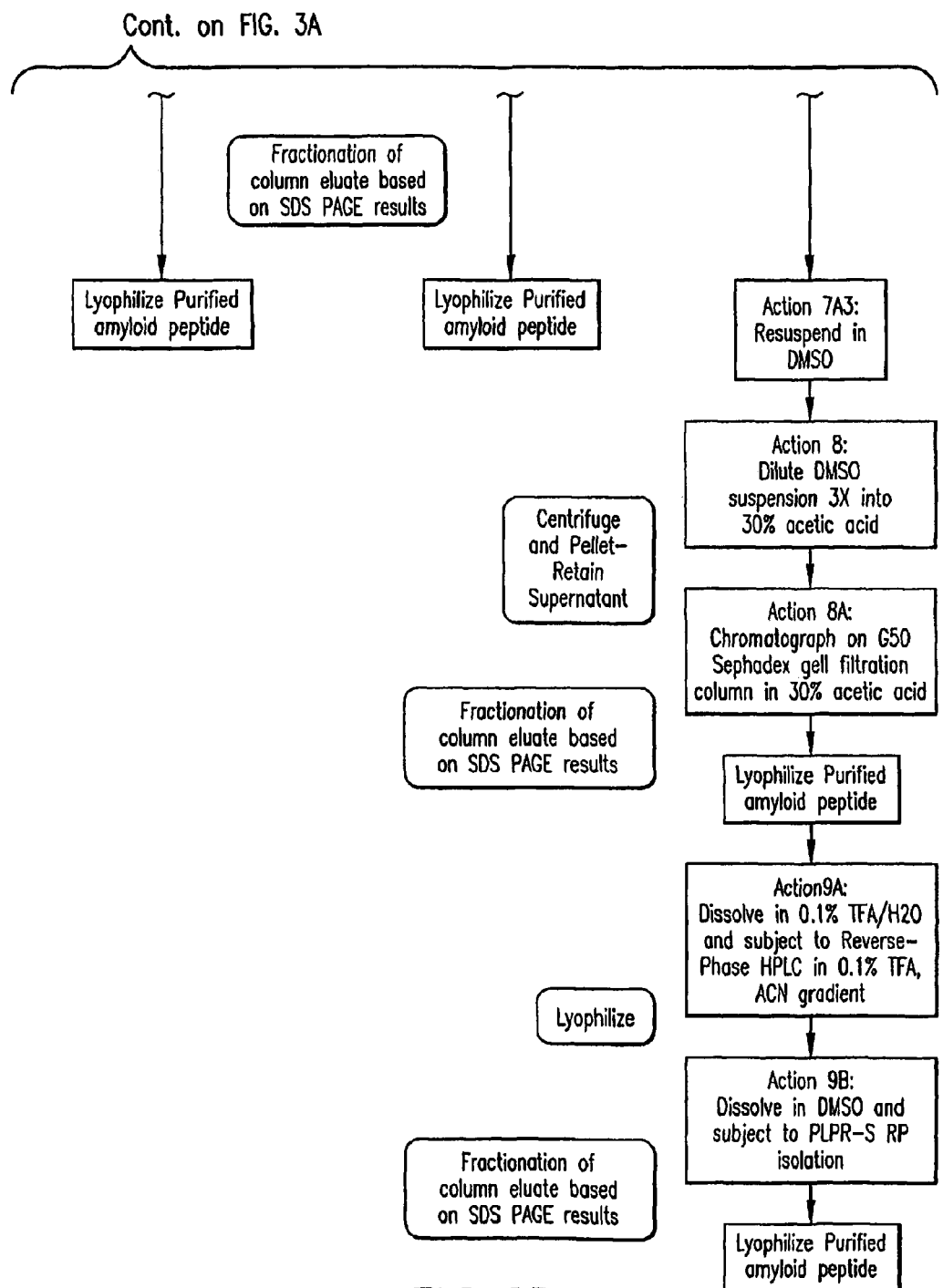

The overall schema developed for purification of the recombinant human amyloids is illustrated in FIG. 3 and described below.

Starting Samples:

The starting material for all isolated samples was cell paste frozen at −80° C. obtained from harvests of *Escherichia coli* cell cultures. The cell cultures originated from multiple 1 liter flask growths or from fermentor runs as large as 35 liters. The media may consist of rich media to produce unlabeled material or minimal media, with or without added labels used to prepare variously labeled samples of A-beta. Either flask or fermentor run may be used with the different media.

ACTION 1: Cell Lysis and Inclusion Body Preparation

Frozen cell paste was removed from the bottle and added to 5-10 volumes of cold lysis buffer in a beaker placed on a stirring plate placed at room temperature. The lysis buffer consisted of 100 mM tris final pH 7.5 to 7.8 at 4° C. For cell pastes derived from fermentor runs, 0.1% triton X100 was added to the lysis buffer. Benzonase, (EMD Biosciences, Madison, Wis.) was added to a concentration of 0.1 ul/ml of cell lysate. The frozen cell paste was allowed to stir until the pellet was uniformly resuspended. This was usually complete within 45-60 min. If needed, the suspension was briefly homogenized with a tissue homogenize to aid in the process. Cell lysis was performed using a M-110L microfluidizer (Microfluidics, Newton, Pa.), keeping the cooling coil under ice; or using a cold French Pressure cell, (SLM Aminco, Rochester, N.Y.). The lysed material at about 15° C. was placed in 250 mL nalgene (Nalge Nunc International, Rochester, N.Y.) centrifuge bottles, or in 50 ml round bottom polycarbonate centrifuge tubes and spun at 2300×G in a JLA 16.25 rotor (Beckman Instruments, Palo Alto, Calif.) for 30 min at 4° C. The supernate was decanted, sampled and then discarded.

ACTION 2: Inclusion Body and Pellet Wash

Cold 50 mM tris buffer at pH 7.5 to 7.8 was added to wash the pellets obtained above. The material was resuspended using a tissue homogenizer and spun at 23000×G in a JLA 16.25 rotor as above. A total of three such tris washes of the inclusion body material were done. Samples of the supernate were collected each time for SDS PAGE analysis ACTION 3: Water Wash Tris buffer washes were followed by one final water wash, This was done in order to remove most of the tris buffer prior to lyophilization of the sample. In this step all the material was simultaneously combined into one bottle. The resuspended sample was finally spun at 23000×G in a JLA 16.25 rotor as above. Samples of the supernate were collected for SDS PAGE analysis and then discarded.

The pellet from the centrifugation was resuspended either in water, (samples for NMR) or in water containing 0.1% trifluoroacetic acid. The latter was added to fermentor runs where large amounts of material were processed at a time. It was noted that material lyophilized from water alone was highly electrostatic and very difficult to handle in larger amounts, whereas the addition of trifluoroacetic acid made the lyophilized material much more easier and safer to handle later. The final volume of resuspended sample was adjusted so as to get a thin slurry which would spread easily on the walls of the lyophilizer flask during the freezing, (shelling) process.

ACTION 4: Lyophilization

The resuspended sample was shell frozen and put on a lyophilizer and lyophilized overnight or longer as needed for completion of the process. Small samples were lyophilized in 50 ml conical polypropylene tubes, so that they would not have to be transferred from there.

ACTION 5: Extraction

Extracting solvents Used were V-A) DMSO; V-B) Heptafluorobutyric acid, (HFBA) and V-C) trifluoroacetic acid. The pathways using fluoro acids are based on the high solubility of A-beta 1-42 or 1-40 in neat TFA [Jao, et. al., (1997), "Trifluoroacetic Pretreatment Reproducibly Disaggregates the Amyloid β-peptide" Int. J. Exp. Clin. Invest., V4, pp 240-252]. Neat TFA has been used as the first step in the preparation of A-beta for the purpose of structure. Neat TFA erases all history of prior structure from the peptide and makes it highly soluble.

ACTION 5A: DMSO Extraction

DMSO was the most commonly used solvent used to extract the peptide from the lyophilized inclusion body sample. From a fermentor run, 10-20 g of such lyophilized material was obtained depending on the amount of starting cell paste. Three hundred mL of DMSO [dimethyl sulfoxide] were warmed to 37° C. in a 600 mL glass beaker on a warm stir plate. The lyophilized material was added to the DMSO carefully without producing dust. Upon transfer, the tissue homogenizer was used to homogenize the suspension. Stirring was continued for another 15 minutes. The whole process was over within 45 minutes. The beaker was covered with a glass plate. The stirring and heat were stopped, and the material allowed to sit overnight on the bench in a fume hood. The temperature of the sample was not allowed to exceed 37° C. at any time. The total volume was about 350 mL and the next morning was spun in two 250 mL nalgene bottles at 25° C. for 30 minutes, 23000×G in a JLA16.25 rotor. The DMSO supernate was decanted into a 600 mL glass beaker. Another 50 mL DMSO was added to each bottle, homogenized and spun as before. The two samples were pooled, resulting in a total of about 400 ml. The pellets were discarded because in a previous experiment it had been shown by SDS PAGE that essentially all of the peptide had been extracted by this procedure.

NMR samples generally contained 5 to 10 gm cell paste. The lyophilized, (from water), inclusion body material was contained in a 50 ml conical polypropylene tube. 25 ml of DMSO was added to this tube and the sample briefly homogenized to bring back into suspension. It was allowed to sit on the bench at room temperature generally for about 4 hours, though sometimes an overnight incubation was done out of convenience. The resuspended pellet was transferred to a polycarbonate centrifuge tube and spun at 23000×G in a JLA 16.25 rotor at 25° C. for 30 minutes. The pellet was small in amount and discarded. The supernate was decanted in a 50 ml conical tube. Sometimes it was frozen at −20° C., awaiting chromatography when several such samples were taken up to this stage in parallel.

ACTION 6: Preparation for Chromatography

Preparation for Chromatography was done by dialysis of the DMSO into the reversed phase column equilibration eluant, 10% acetonitrile in water containing 0.1% ammonium hydroxide, (Action 6A, below).

The DMSO extract could also be directly applied, (Action 6B, below), to the reversed phase column as long as the sample volume was small compared to the volume of the column, (typically less than 10% of the column volume). This was done on an analytical scale column. For NMR samples, 25 ml of the DMSO sample was diluted to 250 ml with 0.1% ammonium hydroxide and applied to the column directly ACTION 6A: Dialysis or Dilution The DMSO extract was carefully poured into a 6000-8000 cut-off dialysis membrane, (Spectrum Laboratories, Rancho Dominguez, Calif.), long enough to hold about 1.5 L. It was dialyzed against 10 L of 15% acetonitrile to which 10 mL of concentrated ammonia (0.1% v/v) had been added. This was allowed to dialyze for four hours on the bench. Periodically, the dialysis membrane was taken out so as to redistribute the dense DMSO and accelerate the dialysis process. At the end of four hours, the membrane was placed into a fresh change of 10 L of the same buffer and the process continued for another two hours. At the end of the dialysis, the sample was removed and centrifuged at 23000×G for 30 min at 25° C. There was essentially no pellet. At the end of the dialysis the 350-400 ml DMSO extract had doubled in volume. The total sample was transferred to a 2 L cylinder and diluted two fold with 0.1% ammonia in water to a total volume as large as 2000 ml. The dilution was done to ensure that the sample would bind to the reversed phase column, (Action 6A)

Action 6A: Chromatography

A 2.2×25 cm, (95 mL) stainless column was hand packed with 15-20 micron, 300A, PLPR-S reversed phase resin from Polymer Labs (Amherst, Mass.). It had been taken through a cycle from 75% acetonitrile+0.1% ammonia, (75% B) and equilibrated to 10% B. The column was connected to a Pharmacia P500 pump (Amersham Biosciences, Piscataway, N.J.), and the 1400 mL was pumped through the column overnight on the bench at room temperature over 1000 minutes. The next morning, the column was washed with the P500 pump with about 250 mL 10% B and then connected to a Beckman HPLC (Palo Alto, Calif.). Washing was continued with 10% B until the absorbance at 280 nm came to baseline and then a gradient was initiated from 10% B to 30% B over 200 minutes (0.1% gradient). The full-scale absorbance was kept at 1 absorbance unit and the flow at 5 mL/min. The material was hand collected. About fifty fractions were collected. They varied in volume, but most were about 10 mL. At 30% B, the column was continued with the elution at 30% B and the eluant allowed to collect. This was later discarded based on the trace. 100 uL of each of the fractions were put on a speed vac, dried and 100 uL of 1× sample buffer added to the tubes. The samples were put on SDS PAGE and the fraction kept overnight at 4° C. Post SDS PAGE, a decision was made to discard the PLPRS reversed phase material instead of attempting to regenerate it since it could potentially contaminate the next run with impurities from the present run.

The next morning, the pooling was done as per the results from the gel. The material was concentrated on a 3500 cut-off membrane on an Amicon (Millipore Inc, Billerica, Calif.) stirred cell and concentrated from 350 to 50 mL in about 4 hours. The sample was all in solution. It was then lyophilized to dryness overnight. The next morning, it was carefully transferred in a weighing hood to two pre-weighed 50 mL conical polypropylene tubes. The total weight transferred was 250 mg plus 330 mg (580 mg total) of lyophilized material. This was stored at −20° C. The entire process took less than five working days. Below is a purification table referred to as Table 3.

TABLE 3

| step | ml | "mg by absorbance" | % |
| --- | --- | --- | --- |
| cell lysis | 1800 ml | 279693 | 100 |
| DMSO ext | 400 | 14400 | 5.15 |
| Load | 1400 | 13353 | 4.77 |
| pool | 350 | 518 | 0.185 |
| conc | 63 | 508 | 0.182 |
| lyophilize | powder | 580 | 0.207 |

Action 6B: Direct Application.

Figure 9:
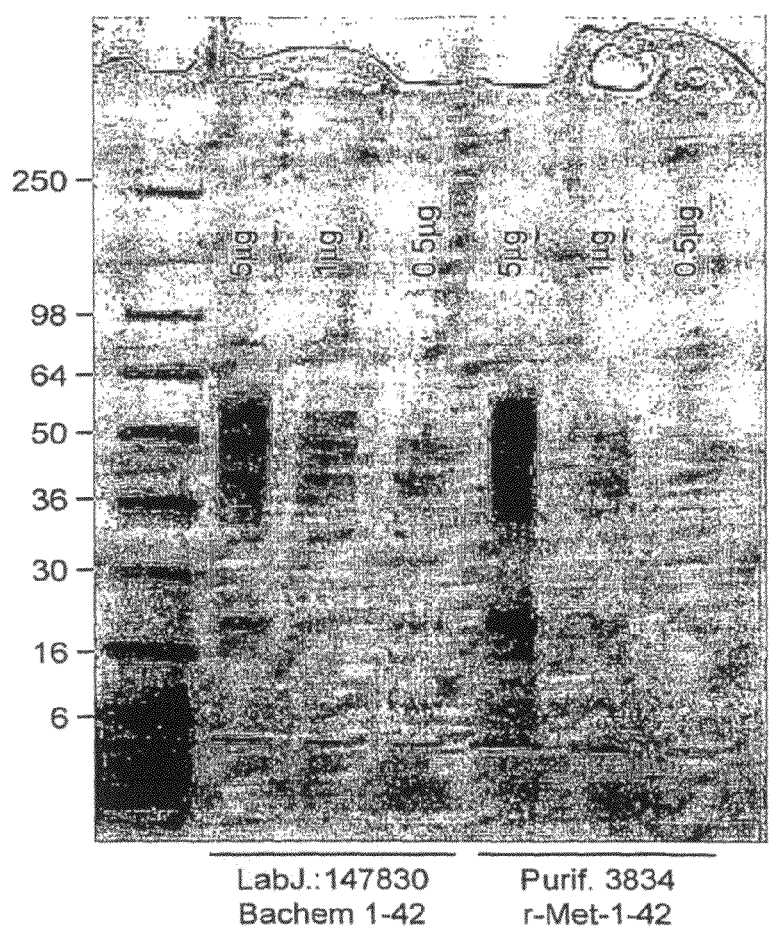
FIG. 9 depicts an SDS-PAGE gel (with molecular weight standards) of globulomers prepared either from synthetic Bachem peptide (1-42) or recombinant MetA-beta (Met1-42) at various gel loadings.

1 mL of DMSO containing 10 ul of concentrated ammonia (1% v/v) was added to 20 mg of solid. The material was briefly sonicated to resuspend the solid and then spun. 0.5/1 mL of soluble material in DMSO was applied to a 3u analytical 0.46×25 cm PLPR-S column, (step 2.1). Pure A-beta eluted around 30% B as judged by SDS PAGE. A characteristic pattern of preformed globulomers was observed on the SDS PAGE gel. The material was lyophilized and taken through the globulomer formation protocol outlined in FIG. 8, and yields the banding pattern on SDS PAGE seen in FIG. 9.

In a second attempt, a 10 mg/mL in DMSO (without addition of ammonia) was made. Half of one mL of this sample was injected directly into the analytical column. In this case, the pH change was achieved on the column. The peptide eluted at the expected % B, and the pool (as judged by SDS PAGE) was made, lyophilized and taken through the globulomer-formation procedure to make competent globulomers as before. For NMR samples, 25 ml of the DMSO sample was diluted to 250 ml with 0.1% ammonium hydroxide and applied to the column directly.

Action 5B, 5C: Acid Extraction Pathway

Extraction could also be done with Heptafluorobutyric acid, (HFBA) and trifluoroacetic acid.

Actions 7A1, 7A2, 7A3: Preparation for Chromatography 300 mL of anhydrous HFBA was placed in a 600 mL glass beaker on a warm stirring plate. The lyophilized IB sample (~10 g) was added to the HFBA in a fume hood with vigorous stirring. Any clumps formed were disaggregated with a tissue homogenizer and a probe sonicator, if necessary. The material was heated to about 40° C., allowed to cool and sit on the bench overnight in the absence of light. Next morning, the HFBA dissolved IB sample, which was mostly in solution, was put on a rotary evaporator using about 40° C. as the bath temperature to remove most of the HFBA. Care was taken not to dry the solid around walls of the flask. (When the material behaved like a viscous syrup, about 50 ml of 1,1,1,3,3,3, hexafluoro isopropanol (HFIP) was added to the flask. The syrup was induced to go into solution in the HFIP by warming, swirling around the flask, using a tissue to homogenizer and/or a sonicator probe.) When all was in solution, the HFIP was removed on the evaporator to a sample consistency of viscous syrup. Another 50 mL aliquot of HFIP was added and the process repeated. 50 mL DMSO was added to the flask when the sample had the syrup consistency. The sample was colored dark brown and went into solution into the DMSO with a little warming. This was allowed to sit at room temperature overnight. Next morning, there was a precipitate settled at the bottom, with a clear supernatant. The sample was spun and the pellet discarded.

Action 8: Addition of Extract to Acetic Acid in Water

One volume of this extract was added slowly to two volumes of 30% acetic acid in water with rapid stirring at room temperature. The stirring was continued for 30 min at room temperature and then the sample spun to remove a small amount of insoluble matter. Meanwhile, a 5×90 cm (~1800 mL) column of Sephadex G50 (Amersham Biosciences, Piscataway, N.J.) was packed in 30% acetic acid and kept ready in the cold room. 150-200 mL of the sample in 33% DMSO was applied to the G50, care being taken not to let the sample freeze. The sample was eluted with 30% acetic acid at 1.5 mL/min for about 1.2 column volumes. Three peaks were obtained. The first (i.e., void) peak was discarded. The second peak contained almost pure A-beta. The third peak contained some A-beta, but also the extraction solvents and was also discarded. The middle peak was lyophilized to dryness and taken up in the smallest amount of DMSO, −10-20 mL, with warming.

Action 9A: Acidic Reverse Phase Chromatography

The sample was spun of any insoluble material and applied to a Vydac TP214 C4 reversed phase column (Grace-Vydac, Hesperia, Calif.) equilibrated in 20% B, (20% acetonitrile containing 0.1% TFA). The A-beta eluted at about 60% B in the TFA system on a silica based C4 column. The pool was lyophilized, taken up in 10 mL DMSO.

Action 9B: Basic Reverse Phase Chromatography

The DMSO sample was then applied to the PLPR-S reversed phase system described in the Action 5A Pathway to get pure A-beta and convert it to the ammonium salt form, which was then lyophilized.

Figure 4:
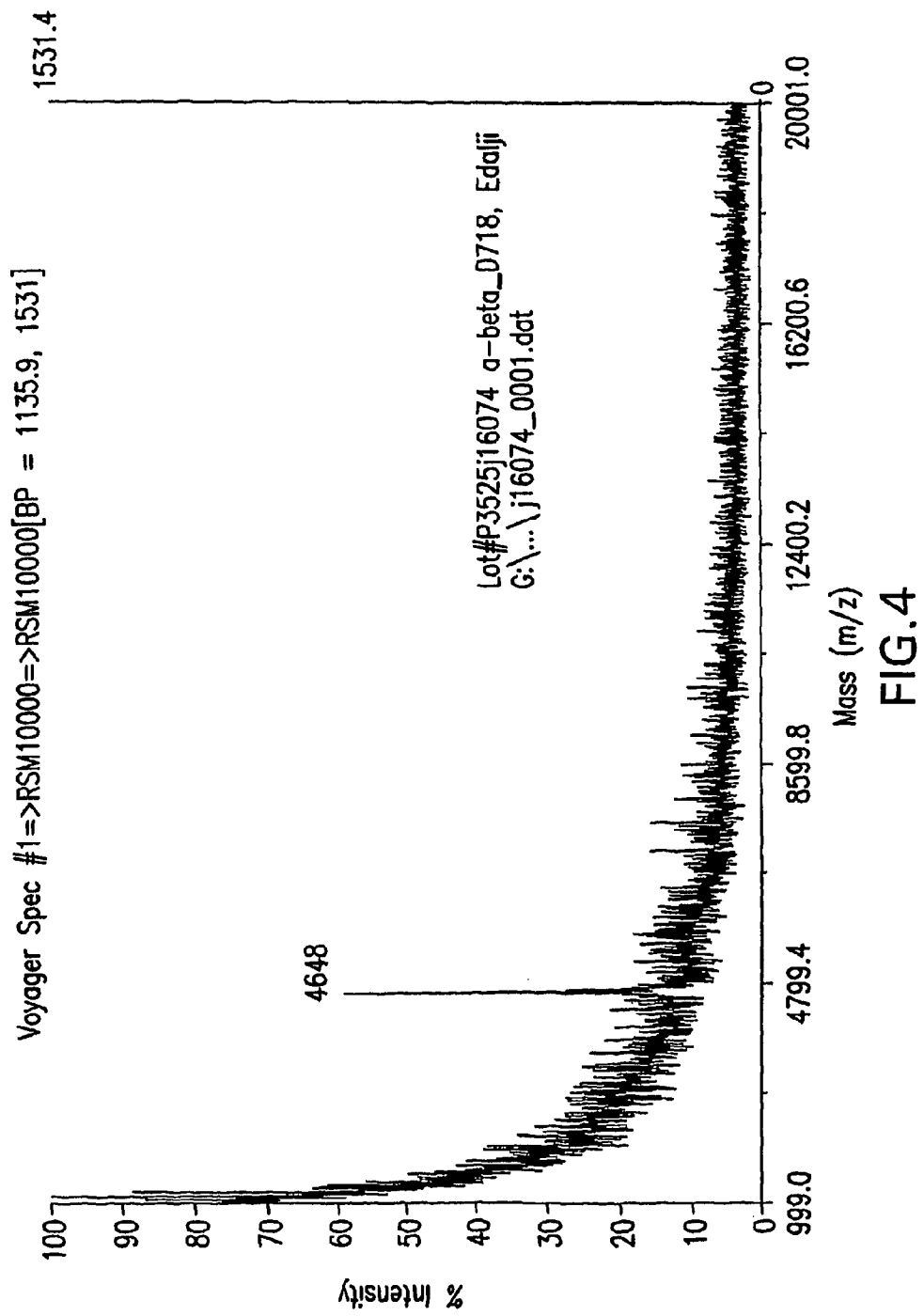
FIG. 4 represents a MALDI mass spectrogram of recombinant Met amyloid beta 1-42. The theoretical molecular weight of the peptide is 4645 Da. The observed value is 4648 Da. The 3 Da difference is within the instrument precision limits.

Proof of Final Composition:

Purified amyloid beta peptide produced by any of these methods exhibited an observed mass of 4645 to 4648 Da (FIG. 4). This was consistent with the presence of N-terminal methionine as expected from the DNA expression sequence employed. Other cloned amyloid beta forms also exhibited the expected masses based on expression the respective expression sequences used.

EXAMPLE IV

Preparation of Globulomers from Recombinant Beta-Amyloids

Standard Procedure: A multiplication factor is used when scaling up.

STEP 1: 2×3 mg human amyloid β(1-42) (Bachem Biosciences, King of Prussia, Pa.)+2×500 uL HFIP (hexafluoroisopropanol) (6 mg/mL suspension) in two 1.6 mL Eppitubes (2×500 µL portions) (Eppendorf Northamerica, Westbury, N.Y.); shaken for 15 h at 37° C. (yielding a clear solution);

STEP 2: dried in speedvac for 1.5 h;

STEP 3: resuspended dry material in 2 aliqots of 132 µL each of DMSO, sonicated in a water bath for 20 seconds, shaken gently for 10 min on a plate agitator; and STEP 4: stored at −20° C. for further use. This yields an amyloid β(1-42) stock suspension of 5 mM in DMSO

END OF DAY 1

STEP 5: filled 690 µL 20 mM NaPhosphate; 140 mM NaCl; pH7.4 buffer in 15 mL Falcon tube;

STEP 6: added 60 L 5 mM amyloid β(1-42) stock suspension in DMSO (400 µM amyloid β(1-42));

STEP 7: added 75 µl 2% SDS in water (0.2% SDS);

STEP 8: incubated 6-8 h at 37° C.; and

STEP 9: added 2475 µL water, 4 fold dilution with water, for a final volume of 3.3 mL, (132/60×3.3=7.26 mL)

STEP 10: incubated 18-20 h at 37° C.,

END OF DAY 2, night 2

STEP 11a: centrifuged 10 min at 3000×G;

STEP 11b: cross-linked post step 11a, (before conc. if intention is to cross link), otherwise;

STEP 12: concentrated supernatant to 1 mL by 30 kDa Centriprep (Millipore Inc, Billerica, Calif.);

STEP 13: dialyzed the sample overnight in PBS/4 (PBS phosphate buffered saline, 1 mM KCl, 154 mM NaCl, 4 mM phosphate, pH 7.4; PBS/4=PBS diluted 1 to 4 with distilled water, pH 7.4 final) at 4 C in a 12-15 kDa cut-off tubing, centrifuged concentrate at 10,000×G for 10 min in Eppendorff tube (clear pellet) and aliquoted in 250 uL and freeze at −20 C. Carried out a Bradford, Sup-12, SDS PAGE.

END OF DAY 3

The yield is usually high as long as sufficient peptide is handled at one time.

Alternatives/Substitutions:

STEP 12: Concentration can be performed on a stirred cell (Amicon, Millipore Inc, Billerica, Calif.)) using a YM10 membrane;

STEP 13: Dialysis can be replaced with a Sephadex G25 column equilibrated against PBS/4.

A calculated extinction is used instead of Bradford.

EXAMPLE V

Characteristics of Recombinant Beta-Amyloids and Globulomers Prepared Therefrom

ELISA Comparing Synthetic and Recombinant-derived Amyloids Using Monoclonal Antibodies Prepared at Different Research Sites.

Figure 5:
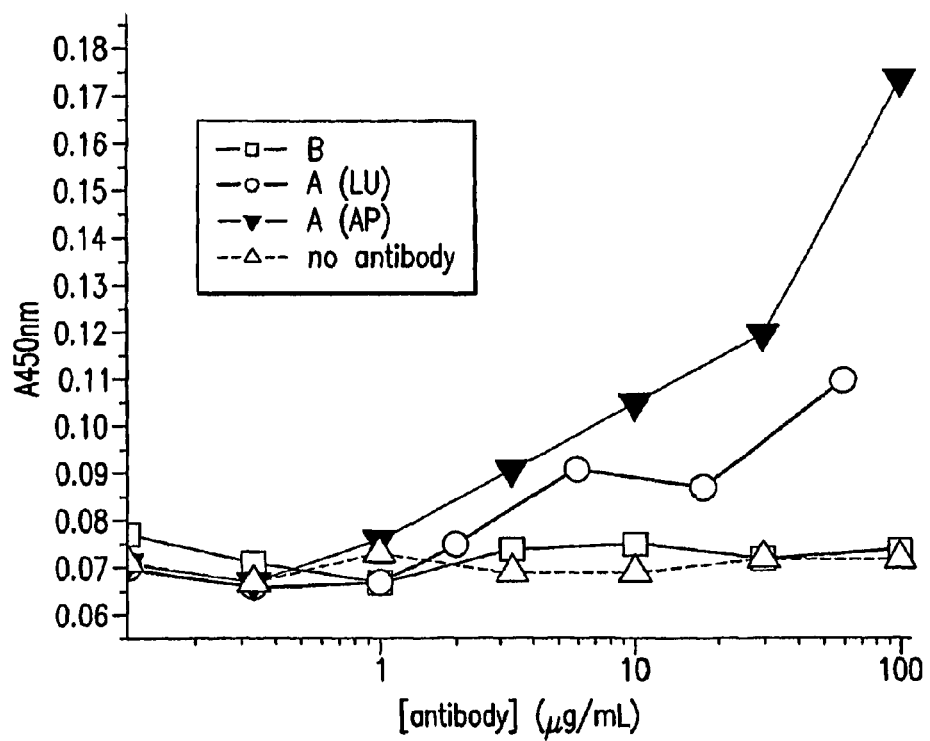
FIG. 5 illustrates the results of an ELISA demonstrating the selectivity of mouse monoclonal antibody A over mouse monoclonal antibody B for globulomers prepared from recombinant amyloid (sequence: Met-Abeta 1-42).

FIG. 5 is a direct ELISA of Aβ globulomers made using Met-Aβ 1-42 peptide produced in E. coli. Display of the globulomer epitope was demonstrated by binding of the globulomer-specific antibody A in a concentration dependent manner. Two different lots of antibody A were examined, made in separate facilities on different continents (LU=Ludwigshafen; AP=Abbott Park). Antibody B cannot recognize globulomers made with full length Aβ 1-42 peptide and does therefore not bind to the globulomers.

Figure 6:
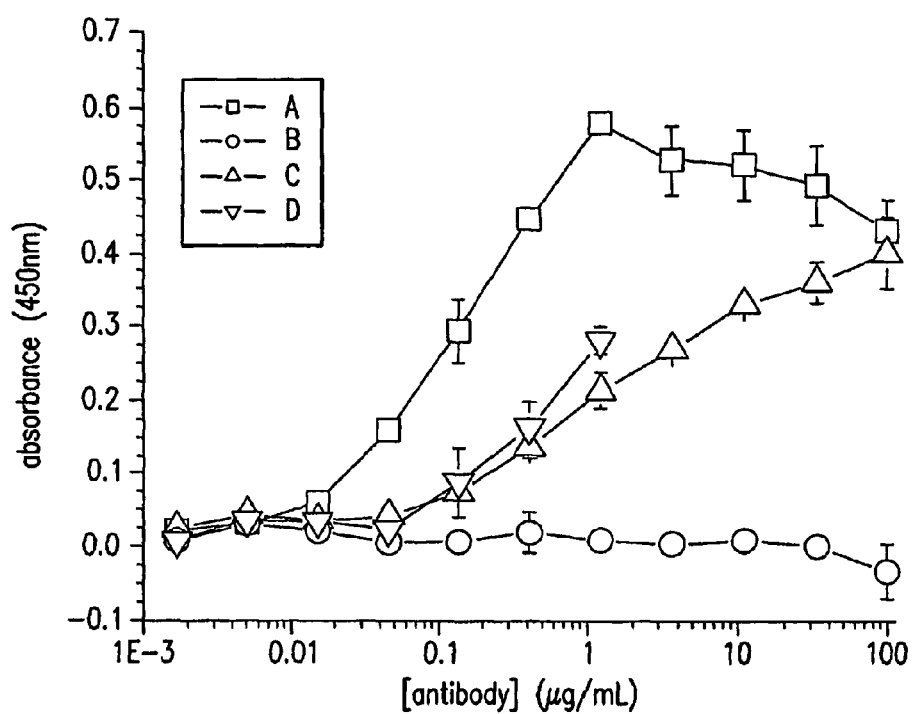
FIG. 6 illustrates the results of an ELISA assay comparing binding of mouse monoclonal antibody A, mouse monoclonal antibody B, mouse monoclonal antibody C and mouse monoclonal antibody to globulomers prepared from recombinant amyloid (sequence: Met-Abeta 1-42).
Figures 7, 8:
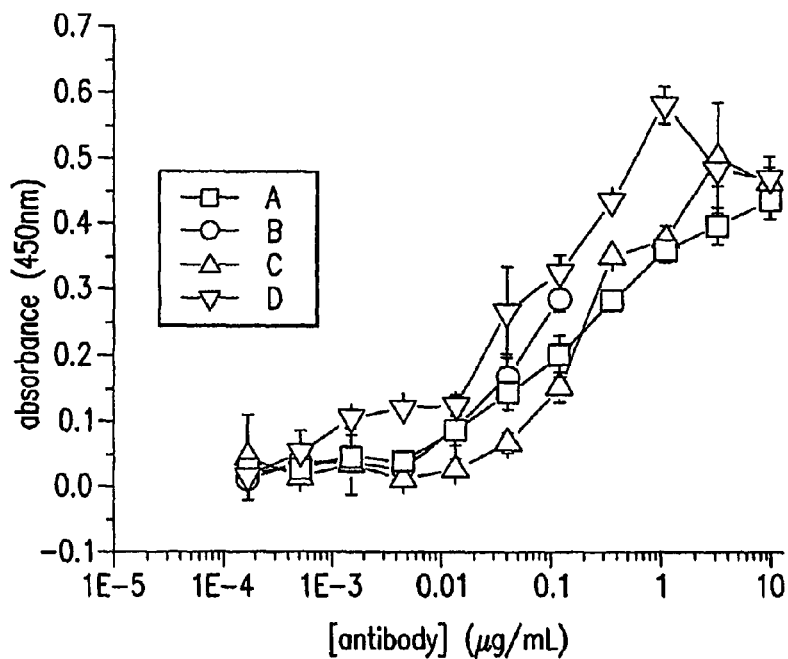
FIG. 7 illustrates the results of an ELISA assay comparing binding of mouse monoclonal antibody A, mouse monoclonal antibody B, mouse monoclonal antibody C and mouse monoclonal antibody D to globulomers truncated to sequence residues 20-42 prepared from recombinant amyloid (sequence: Met-Abeta 1-42).
FIG. 8 summarizes the steps employed to prepare globulomers using either synthetic amyloid peptide or recombinant full-length amyloid peptides.

ELISA Comparative Identification of Globulomeric Epitope(s) presented in Full-length and Truncated Recombinant Amyloid Globulomers The ELISA data presented in FIG. 6 shows the discrimination between mouse monoclonal antibodies A, C, D and B when detecting full-length globulomers comprised of recombinant human amyloid peptide Met1-42 (FIG. 2). The figure indicates antibody A recognizes these globulomers at lower concentrations (binds more tightly) than antibodies C and D, which, in turn, bind more tightly than the 10F11 monoclonal antibody. By comparison the ELISA data presented in FIG. 7 shows all antibodies recognize globulomers which have been truncated with the proteolytic enzyme thermolysin and are (primarily) comprised of the amyloid sequence from residue 20 to reside 42 (see FIG. 2). This ELISA data indicate these antibodies recognize the truncated globulomers with nearly the same affinities. Taken together FIGS. 6 and 7 show that antibody A is highly selective for the globulomeric epitope (as defined below by NMR-derived structural data). Antibodies C, D and B differentially prefer the shortened 20-42 sequence form (FIG. 2) of amyloid. The greatest difference in selectivity for truncated amyloid is shown by antibody B. Based on these differences in epitope interactions, an antibody with the epitope binding characteristics like that of antibodies C or D antibody are more preferred and an antibody with the epitope binding characteristics of antibody A is most preferred for binding to the globulomeric epitope contained within the 2042 (or 20-43) amyloid sequence range.

DotBlot analyses of a series of mAbs (A, B, C and D) against 9 different preparations of synthetic amyloid beta and APP were performed (data not shown). In addition to confirming the ELISA results depicted in FIGS. 5, 6 and 7, these dotblots together with NMR structural data presented below also form the basis for establishing the most preferred embodiment of the reactive epitope, specifically the "closed" form of the beta amyloid conformational switch (FIG. 3). In this closed form, the epitope is exposed and available for immune reaction. In the "open" form the amyloid fibrils rapidly aggregate to form larger fully parallel sheet structures and thus are no longer available as a distinct epitope. (The fibrillar form reacts nearly exclusively with monoclonal antibody C while monoclonal antibody A reacts with globulomers with or without glutardialdehyde crosslinking and the truncated amyloid 20-42. While monoclonal antibody D and B react with either thermolysin truncated or both thermolysin and EndoGluC truncated to sequence 12-42 (data not shown).

ELISA Materials: Microtiterplates were from Nunc Immuno Plate, Maxi-Sorb Surface, flat bottom, (Catalogue #439-454). The conjugate (secondary antibody) was Donkey anti-mouse HRPO conjugate from Jackson Immuno Research, (Catalogue #715-035-150). The HRPO substrate was 3,3',5',5'-Tetramethylbenzidine Liquid substrate (TMB), Sigma, (Catalogue #T4444). Non-fat Dry Milk (NFDM) was from BioRad (Catalogue #170-6404). All other chemicals were from conventional sources.

Buffers and solutions: PEST buffer: Sigma PBS made with 0.05% Tween 20 PBST with 0.5% BSA was made by dissolving 0.5 gm ESA in 100 mL PBST. Blocking solution was 3% NFDM in PBST. Conjugate diluent was 1% NFDM in PBST. The coating buffer was 100 mM NaHCO3 pH8.2. The HRPO Stop Solution was 2M $H_2SO_4$.

ELISA Plate Coating: The amyloid globulomers to be tested were diluted to 10 ug/mL in coating buffer. 100 uL was added to each well to be coated. The wells were sealed with plate sealing film and left at 4° C. overnight.

Plate Blocking: The coating solution was removed from the wells. Wells were washed 2-3× with 150 uL of PBST (optional). 300 uL of blocking solution was added (3% NFDM in PBST). The wells were then covered with plate sealing film and incubated for 2 hrs at room temperature, with agitation.

ELISA Primary Antibody: The blocking solution was removed from the wells. Washed 2-3× with 150 uL of PBST (Optional). 100 uL of primary antibody solutions were added. For the full length met+Aβ 1-42 globulomers, solutions of 0.04 to 100 ug/mL of antibody 5F7 were used. The antibody was diluted using PBST with 0.5% BSA, covered with plate sealing film and incubated for ~2 to 3 hrs at room temperature with agitation.

ELISA Secondary Antibody (HRPO Conjugate): The primary antibody solution was removed from the wells, washed 2-3× with 150 uL of PBST (mandatory), and 200 uL of secondary antibody (HRPO conjugate) solution diluted 1:5000 in PBST with 1% NFDM was added. The wells were covered with plate sealing film and incubated for ~1 hr at room temperature with agitation.

Substrate Development The conjugate solution was removed from the wells, washed 2-3× with 200 uL of PEST (mandatory). 100 uL of HRPO substrate solution was then added to each well. Color was then allowed to develop under observation (i.e., blue) (The reaction is usually done in 510 minutes at room temperature.) 50 uL of stop solution was added to each well and the color turned from blue to yellow. The wells were read at A450 nm using microtiter plate reader. It is advisable to read within 30 min of addition of the stop solution.

Thermolysin Truncation of Globulomers: To 9 mg of globulomers in approximately 20 mL was added 45 ul of 4 mg/ml thermolysin, (Calbiochem), in PBS (180 ug thermolysin or 9000 uL/180 uL equals about 1 to 50, (v/v) dilution). The reaction was left to proceed overnight at room temperature. The next morning the reaction mixture was clear to the eye. EDTA was added to 0.5 mM to stop the thermolysin reaction. To prepare the final product for analysis, it was chromatographed as follows: 1 mL of the truncated globulomer was adjusted to pH 10 with ammonium hydroxide. It was then applied to a 7 mm polymer reverse phase column to remove SDS (polymer laboratories, Amherst Mass.) and eluted with a 1%/min gradient. The major eluted fraction contained the purified truncated (20-42) globulomer.

DotBlot Materials, Procedure and Sample Preparation: A set of various synthetic amyloid beta species and alzheimers precursor protein (APP) were dotted as antigens on Nitrocellulose paper sheets (Trans-Blot Transfer Medium (Catalog 162-0113) Pure Nitrocellulose Membrane (0.45 μm, BIO-RAD Laboratories, Inc., 2000 Alfred Nobel Drive, Hercules, Calif.) in about 2-5 mm spots via Hamiltan syringe in varying concentrations (100 pmol, 10 pmol, 1 pmol and 0.1 pmol) and dried by air stream. (Lanes 1-10).

Detection-reagent: NBT/BCIP Tablets (Cat. No. 1 697 471) Roche Diagnostics GmbH, Roche Applied Science, Normenwald 2, 82372 Penzberg Germany.

Albumin, Bovine: SIGMA-ALDRICH (Catalog A-7888) (BSA) St. Louis, Mo. 63178.

Blocking: 5% Skim Milk Powder in TBS.

Buffer solutions: TBS, 25 mM Tris HCl-pH 7.5, 150 mM NaCl; TTBS, 25 mM Tris HCl pH 7.5, 150 mM NaCl, 0.05% Tween 20; PBS, 20 mM phosphate, pH 7.4, 140 mM NaCl, 0.2 mg/ml BSA Antibody I: 0.2 µg/ml Antibody (20 ml per Membrane=>4 µg Ab) in 1% Skim Milk Powder in TBS.
Antibody II: 1:5000 dilution (20 ml per Membrane=>4 µl Ab) Anti-Mouse-AP in 1% Skim Milk Powder in TBS
Procedure:
1) 1 µl Antigen dilution (1-5) dotted in a distance about 1 cm,
2) Dry 10 minutes at room temperature.
3) Blocking: Block the membrane by adding 30 ml 5% Skim Milk Powder in TBS and incubated 1.5 h by room temperature.
4) Wash: Decant the blocking solution and wash the membrane with 20 ml TTBS 10 minutes by room temperature
5) Antibody I: Dilute the primary antibody in 1% Skim Milk Powder in TBS to 0.2 µg/ml. Use 20 ml per membrane. Incubate over Night at room temperature.
6) Wash: 2 times with 20 ml TTBS for 10 minutes 1 time with 20 ml TBS for 10 minutes.
7) Antibody II: Dilute the secondary antibody in 1% Skim Milk Powder in TBS to 1:5000. Use 20 ml per membrane. Incubate 1 h at room temperature.
8) Wash: 2 times with 20 ml TTBS for 10 minutes 1 time with 20 ml TBS for 10 minutes
9) Develop: Dissolve 1 tablet NET/BCIP in 20 ml water. Decant the wash-solution and cover the membrane approx. for 10 minutes with the develop-solution.
Block up: wash with water The individual samples were prepared as follows:

Amyloid beta(1-42) globulomers were prepared according to S. Barghorn et al. JoN, 2005, 95, 834-847. Amyloid beta (1-42) in HFIP, was prepared as follows: 1 mg/ml amyloid beta (1-42) was dissolved in HFIP for 1.5 h at 37° C.; dried in speed vac; dryed material was resuspended in DMSO; diluted in PBS with 0.1% Pluronic F68, stirred 1 h at 20° C.; centrifuged for 20 min at 3000 g. The pellet was resuspended in PBS with 1% Pluronic Fe-6; sonicated 20 sec and diluted 1:6.7 in water and stir 1 h at 20° C. The sample was then centrifuged at 20 min 3000 g, supernatant decanted and stored at 80° C.

Amyloid beta (20-42) globulomer was prepared from amyloid beta (1-42) globulomer as described above.

Crosslinked amyloid beta(1-42) globulomer was prepared from amyloid beta(1-42) globulomer as follows: 1 mg/ml amyloid beta(1-42) globulomer was treated with 1 mM glutaraldehyde for 2 h at room temperature followed by 5 mM ethanolamine treatment, 30 min, RT.

ADDL's were prepared according to Lambert et al. PNAS 95, 6448-6453, 1998.

Truncated amyloid beta (12-42) globulomer was prepared as follows: amyloid beta (1-42) globulomer was treated at 1/93 (v/v) EndoGluC proteinase (Roche Biosciences, Indianapolis, Ind.) for 20 h at 20° C.; the reaction was stopped with an excess of disopropyl fluorophosphate (DIFP); it was then concentrated using a 30 kD molecular-weight cut-off centriprep and dialysed against ¼ PBS where the dialysate was adjusted to 0.1% SDS content; after dialysis it was stored at −80° C.

Amyloid beta (1-40) in HFIP, was prepared as follows: 1 mg/ml amyloid beta(1-40) was dissolved in HFIP for 1 h at 37° C.; dried in speedvac, resuspended dry material in DMSO and store at −80° C.;

Amyloid beta (1-42) in 0.1% NH4OH, was prepared as follows: 1 mg/ml amyloid beta(1-42) dissolved in 0.1% NH4OH and stored at −80° C.

Amyloid beta (1-42) fibrils were prepared as follows: 1 mg/ml amyloid beta(1-42) was dissolved in 0.1% NH4OH; diluted 1:4 in PBS; pH adjusted with HCl to pH 7.4; incubated 20 h at 37° C.; a 10 min centrifugation at 10000×G; resuspended pellet in PBS and store at −80° C.

APP (first Dot: 1 pmol) was supplied by Sigma Chemical Co., St. Louis, Mo.

Figure 10:
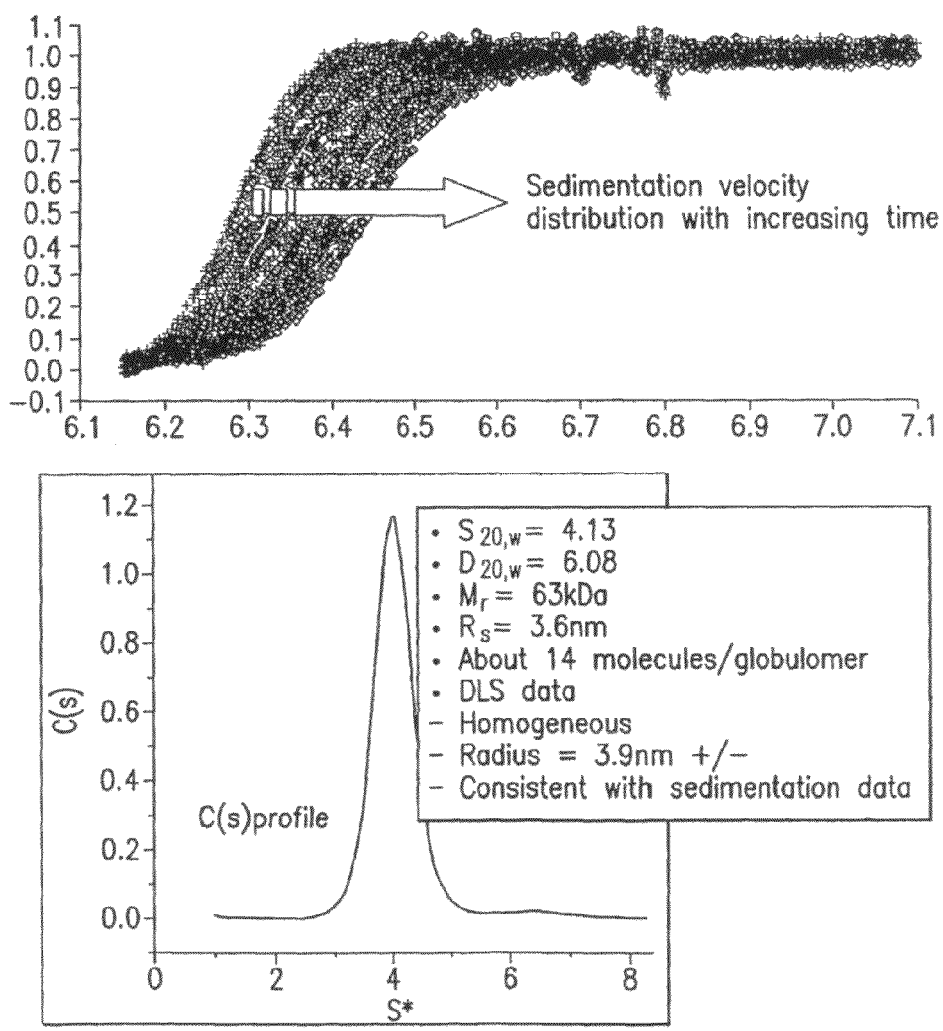
FIG. 10 depicts the results of hydrodynamic analyses (sedimentation velocity and dynamic light-scattering (DLS)) of globulomers prepared from recombinant MetA-beta 1-42
Figure 11:
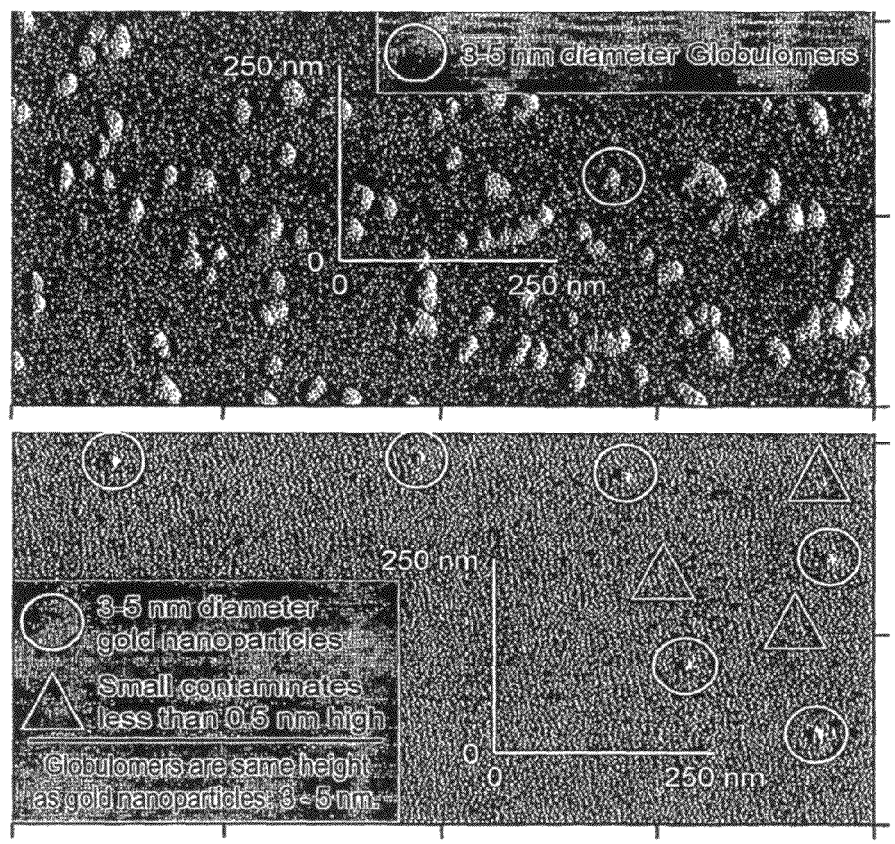
FIG. 11 depicts representative atomic force microscopy (AFM) images of globulomers prepared from recombinant MetA-beta 1-42 or gold nanospheres purchased from Sigma Chemical Co. (St. Louis, Mo.), Edge image data only, the sharpest features are lighter. The darker the image the closer a feature is to the surface of the mica chip substrate surface.

Unexpected Structural Features and Biophysical Characteristics:
a) Hydrodynamic Features FIG. 10 depicts the results of hydrodynamic analyses (sedimentation velocity and dynamic light-scattering (DLS)) of globulomers prepared from recombinant MetA-beta 1-42. The upper panel depicts a series of representative sedimentation velocity profiles for recombinant Met-Abeta globulomers prepared as described above and centrifuged in 2.5 mM sodium phosphate, 0.65 mM KCl, 34.5 mM NaCl, pH 7.4. As indicated by the arrow scan time increase towards the right, the profile comprises a series of individual S-shaped scans produced by a Beckman XLI analytical ultracentrifuge. The x-axis in the upper panel is centimeters from the center of centrifugation, and the γ-axis is relative displacement of interference fringes. The lower panel depicts the C(s) profile of the complete sedimentation distribution (upper panel) over the entire analysis time period, calculated using SEDFIT according to Schuck (Biophysical Journal, 2000, 78:1606-1619). The C(s) analyses and separate results obtained from dynamic light-scattering are summarized in the figure. They indicate the globulomers have a molecular weight of about 63 kDa corresponding to a globulomer comprising ~14 Met-A-beta monomers (14×4645)=65030 Da.

b) Experimental Protocols for Analytical Ultracentrifugation, Sedimentation Velocity Experiments:

Samples were loaded into standard two-sector cells using sapphire windows. All samples were examined using either a 4-hole or an 8-hole rotor. Conditions were as follows: temperature: 20 C, rotor speed: 42,000 rpm, interference data were collected; absorbance data were collected at 280 nm in continuous mode with a radial step size of 0.003 cm. One data point was collected per step (no signal averaging). Typically, 200 scans or less were collected over the course of no more than 9 hours.

c) Fitting the Data:

Two complementary methods were used to fit the data: A continuous S distribution analysis (C(s) analysis, FIG. 7) was done as implemented in SEDFIT v8.9 (Schuck, 2000) to understand the overall heterogeneity of the samples. Both radial and time independent noise were fit and removed from the data using a maximal entropy algorithm. The raw moving boundary profiles (FIG. 6, upper panel) were fit to a modified Fujita-MacCosham function using the program SVEDBERG (Philo, J. S., 1997, Biophysical Journal, 72:435-444). This allows determination of both sedimentation coefficient (S) and diffusion coefficient (D), thus allowing calculation of the molecular weight (Mr) of the species specified by the model. For this analysis, the scans were visually inspected, and only the appropriate scans were used. Criteria for picking scans included enough clearance from the meniscus and sufficient remaining plateau region left (i.e., not sedimented too far). Models included single species, and multiple species (up to the maximum of 3).

d) Results from Fits:

C(s) analysis: The C(s) analysis suggested mainly a single species with S-4, a slight amount of higher order aggregate was also present. This larger species peak was somewhat broad, suggesting multiple unresolved species could be present. The frictional coefficient, $f/f_o$, was globally fit (all species) to $f/f_o=1.54$, suggesting the oligomers present were not simple spheres.

SVEDBERG Analysis: While it was possible to fit the data with a single species, a better fit was obtained when additional potential species were added. An improvement in the fit was judged by less systematic variation in the residuals and a 38% reduction in the goodness of fit parameter. For the main component (92% of the material based on the species deconvolution), the fit returns values of $S_{20,w}$=4.1, and $D_{20,w}$=5.5. Using these values, a $M_r$ of ~68 kDa was obtained, indicating an oligomer of ~14 peptide units A shape factor of f/fo=1.42 was obtained, again suggesting a more prolate sphere. The minor components are represented by broad distributions of larger S value, indicating they are likely comprised of small amounts (less than 10%) of a number of unresolved higher-order aggregates A complimentary analysis approach which can make results visually clear was to force a model to fit fixed values of molecular weight—representing specific numbers of oligomers in the globulomeric assembly. The sum of the squares of the residual errors from these fits is then plotted against each possible increment of globulomer size. This analysis is presented in FIG. 21 for a two component fit (major component is globulomer, minor component is the higher-order species). In this plot the oligomeric state of major component Abeta peptide was held fixed from 10 to 18 by fixing the molecular weight of the proposed aggregate (as an increment of Mr=4645), and fits were performed in SVEDBERG. The resultant goodness-of-fit parameters (sum of squares) were plotted versus the number of peptides per globulomer for each forced fit. The minimum value (lowest fitting error) occurs with an oligomeric state of about 14 peptides per globulomer.

Figure 14:
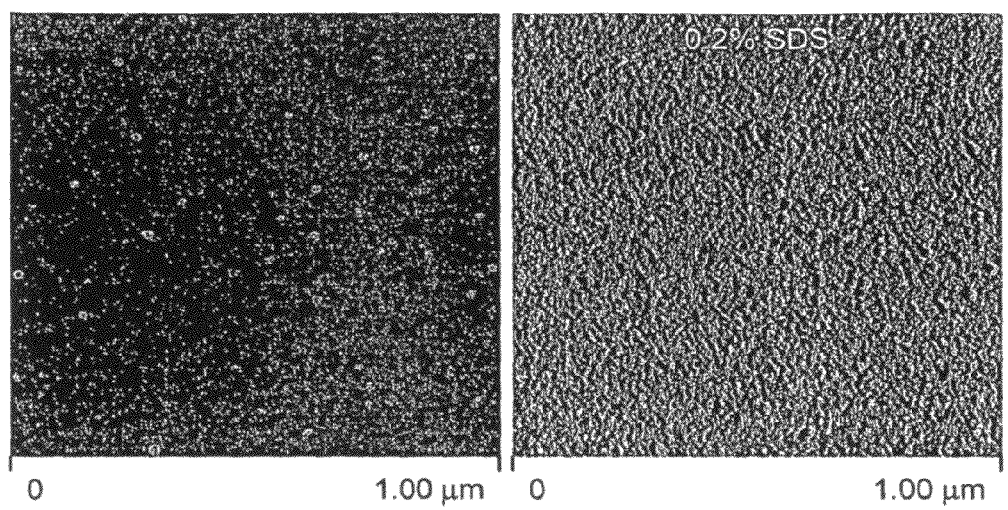

Overall, sedimentation analysis suggests a sphere-equivalent radius of about 3.6 nm, while DLS suggests a value of about 3.9 nm. DLS studies were performed using a laser light scattering system (ALV Instruments, Germany) equipped with APD detector. The laser wavelength is the 647 nm line of a krypton ion laser (Coherent Instruments, CA), and scattering angles were chosen between 40 and 150 degrees Samples were measured at a bath-controlled temperature of 20 C. Analysis of correlation functions for multiple components were performed using a regularization (Laplace inversion algorithm (see, e.g., SPIE Proceedings Vol. 1430 "Photon Correlation Spectroscopy Multicomponent Systems" Ed. K. S. Schmitz, ISBN: 0-8194-0520-5, 266 pages). Additional DLS measurements were performed using a DLS Plate Reader DynaPro (Protein Solution, Wyatt Instruments, CA) with a backscattering APD detection using a scattering angle 158 degrees. The diode laser has a 819.7 nm emission; the temperature is monitored but not controlled (T~25C).

e) Atomic Force Microscopy of Globulomers:

FIG. 14 depicts representative AFM scans of globulomers (upper panel) and gold nanospheres (lower panel). The X and Y axis dimensions are equivalent and markers of 250 nm in length are indicated for each. Each sample was scanned under identical setup conditions and in each case the globlomers and the nanospheres appear to extend 3 to 5 nm in height (Z axis). Absolute calibration of the Z-axis was performed using a NIST (National Institute of Standards and Technology) 3D reference standard, with grooves 20 nm deep. The standard was obtained from Nanodevices, Inc, a division of Veeco Instruments, Woodbury N.Y. Repeated height measurements from this standard (N=10) revealed an average height of 19.909 nm with standard deviation of 0.228 nm. Veeco/Digital Instruments warrants height measurement calibration to be linear in the range from zero to 20 nm. To determine the performance of the AFM in the height range of globulomers, and to estimate the lateral distortion of the AFM tip to measurements in the X and Y dimensions, colloidal gold nanospheres (averaging 5 nm in diameter) were measured by AFM. The gold nanospheres were purchased from Sigma (St. Louis, Mo., catalog #G-1402, lot 103K91851), and technical experts at Sigma stated that the particles should exhibit a size range of 3.5 to 6.5 nm. Gold nanospheres were used since, at the forces typically used in tapping mode AFM, these nanospheres are not compressible by the tip of the AFM imaging tool. By comparison amyloid aggregates have been previously shown to distort slightly when imaged by AFM (Stine et. al., 1996). The manufacturer (Veeco/Digital Instruments) specifies the radius of curvature of the AFM tip is 10 nm (Veeco model # TESP, tips actually manufactured by NanoWorld AG, Neuchatel, Switzerland; type:NCH-W, Unit No.: 12543L320, spring constant 28-54 N/m). Based on image measurements, the gold nanospheres (3-5 nm actual) appeared to be about 15 nm in diameter, indicating a lateral image distortion factor of 4 to 7. Single imaged globulomers in the upper figure measured about 23 nm or about 3.2 to 4.2 nm with lateral distortion removed. These dimensions corresponded with the sphere-equivalent radii determined from hydrodynamic and light scattering analyses (above).

Samples were diluted to a concentration of 0.029 mg/ml using water from a Barnstead NANOpure water system (APS Water Services Corp., Van Nuys, Calif.). Conductivity of the water was monitored prior to use, and all water used had a minimum conductivity of 18.0 MD-cm. Samples were centrifuged on an Eppendorf 5415C Microfuge (Eppendorf AG, Hamburg, Germany) for 10 minutes at 14000 rpm prior to deposition. Twenty microliters of sample were deposited on ½" diameter freshly cleaved Mica discs (Ruby Red Mica Sheets, Cat. #71850, Electron Microscopy Sciences, Ft. Washington, Pa.). Each sample was placed in a closed Petri dish with a damp paper towel and allowed to incubate for 7 minutes. Each sample was then rinsed with 1 ml of NANOpure water (5-200 ul aliquots) and allowed to dry under a stream of gently flowing air. Atomic force microscopy (AFM) was performed on a Veeco/Digital Instruments Nanoscope IIIa (Veeco, Santa Barbara, Calif.) Tapping mode AFM was performed utilizing TESP tips ($f_o$~280 kHz). Images were collected at 4 nm, 2 nm, and 1 nm in both height and amplitude mode. The height of individual globulomers was determined using section analysis of the 'height mode' image (see Stine et al., 1996, J. Prot. Chem., 15, 193-203).

Figure 12:
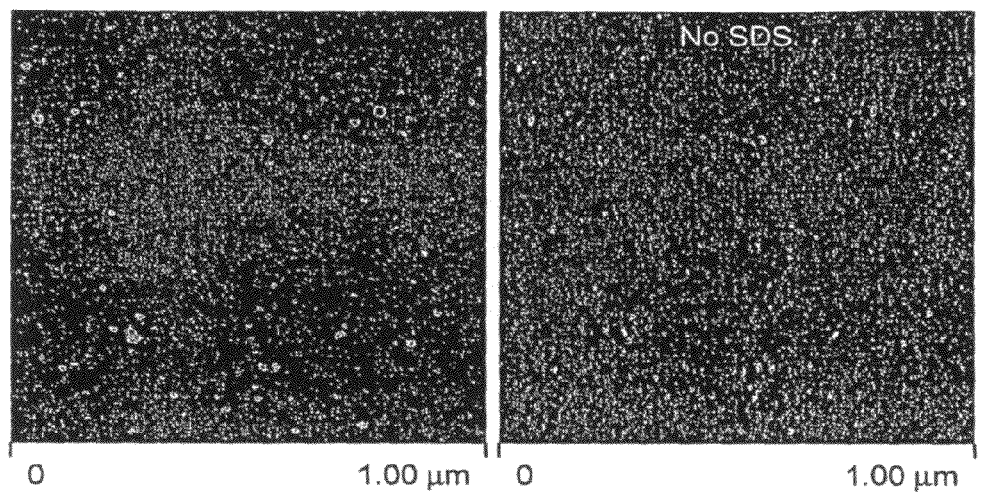
FIGS. 12 to 14 depict representative AFM images of globulomers (30 microgram/mL monomer amyloid concentration) as visualized in no SDS (FIG. 15), 0.05% SDS (FIG. 16) and 0.2% SDS (FIG. 17). In each figure, left: height image, right: edge image. The highest (left) and sharpest (right) features (respectively) are lighter in each image. The darker the image the closer a feature is to the surface of the mica chip substrate surface.
Figure 13:
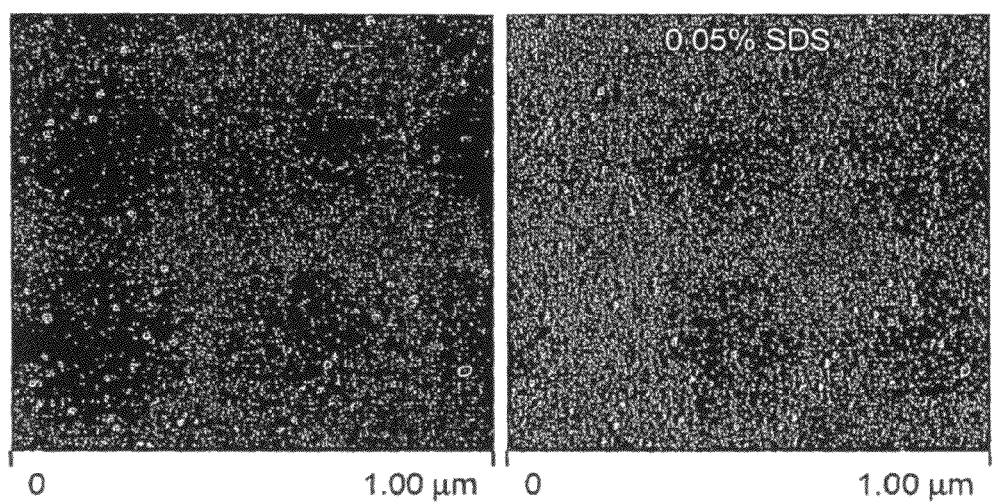

FIGS. 12, 13 and 14 depict representative AFM images of globulomers as visualized in no SDS (FIG. 12), 0.05% SDS (FIG. 13) and 0.2% SDS (FIG. 14). At these concentrations of the Met-Abeta peptide (30 ug/ml monomer concentration or greater), in the presence of SDS, the tendency of the peptide to form rapidly (tens of minutes) large dense fibrillar aggregates is much reduced and the peptide is stabilized by the SDS against the formation of these higher-order fibrillar aggregates Overall, creating the globulomers through SDS treatment stabilizes them against rapid aggregation to larger fibrillar forms. It is believed that the sulfate moiety on the dodecyl sulfate chain of SDS acts to block aggregation to larger species by charge-charge repulsion between the negatively charged sulfate groups bound to the globulomeric assemblies of peptide. As the SDS concentration is reduced in the process of preparing the globulomers (FIG. 9) only residual amounts remain after dialysis. The unique structures/conformations of the globulomeric assemblies of peptides obtained by this procedure (FIGS. 20-24) are (by virtue of their inherent conformations) thereby prevented from undergoing rapid aggregation to form large fibrillar aggregates with molecular weights of hundreds of thousands or many millions of daltons. These stabilized globulomers present unique epitopic regions (distinct from epitopes on amyloid fibrils) which react with both human auto-antibodies and mouse monoclonal antibodies (FIGS. 5-7). Biologically, the generation in vivo of the amyloid peptide occurs in the natural environment of a cellular membrane (FIG. 23). In this setting the amyloid peptide always exposed to—and even embedded in—the cellular membrane. It is common biological knowledge that this membrane is composed of a dual-layer of amphipathic biological lipids. It is expected, therefore, that the SDS used to create the globulomers mimics the natural amphipatic environment of the cellular lipid membrane. In this amphipatic environment the amyloid self-assembles into globulomeric structures which present (expose) the aforementioned epitopic regions.

Figure 15:
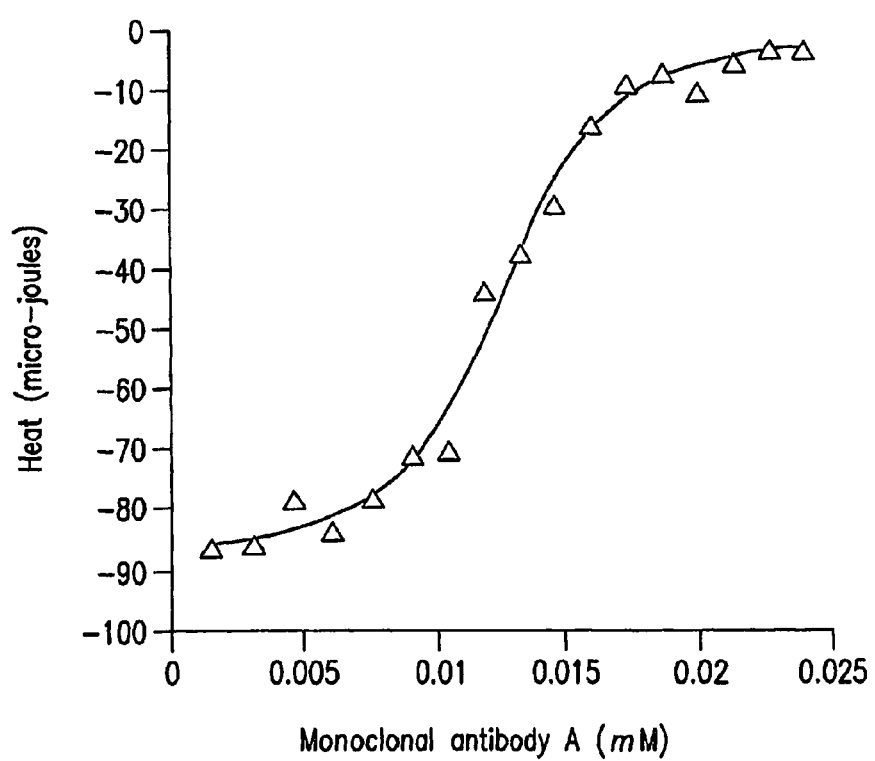
FIG. 15 illustrates the results from the binding of the monoclonal antibody A to globulomers prepared from recombinant MetA-beta 1-42. The binding was directly measured by isothermal titration calorimetry (ITC). In this example the calorimeter cell contained amyloid beta at a concentration of 86 micromolar (based on a monomer unit). It was titrated with the A antibody at 132 micromolar. Both were in a 5 mM sodium phosphate buffer with 35 mM NaCl at pH 7.4. The fitted dissociation constant (Kd of binding) was 490 nanomolar (or 0.46 uM), the observed enthalpy of binding was −47.5 kilojoules/mole and the apparent stoichiometry of binding was 6.3 amyloid beta molecules per antibody molecule. Together with the hydrodynamic analyses, this suggests about two combining sites for full-length antibody per globulomeric unit.

The globulomers obtained by this process in vitro have utility in determining the peptide secondary-structures presented as epitopes (FIGS. 17-24) for use in selection and design of appropriate therapeutic (blocking) monoclonal antibodies. These globulomers also have uses in creating potential vaccines for active immunization against Alzheimer's disease. Additionally, these globulomers also have utility as tool-molecules for the discovery of small molecule agents (drugs) that can block globulomer formation or alter globulomer interactions with other cellular entities and thereby reduce or eliminate disease progression. Additionally, the stabilized globulomers may also be employed for the creation of diagnostic testing methods to predict disease tendency or to monitor efficacy of therapeutic agents It is expected that amphipathic agents beyond SDS, singly or in combination, such as naturally known fatty acids or detergents will also be useful in preparing globulomers in vitro. A partial list of chemical agents expected to be useful in preparing globulomers includes one or more of the following species:

octanoic acid, nonanoic acid, decanoic acid, undecanoic acid, dodecanoic acid, tetradecanoic acid, 11,14-Eicosadienoic Acid, 13-Docosenamide, 13-epi-12-oxo Phytodienoic Acid, 13(Z)-Docosenoic Acid, 17-Octadecynoic Acid, 1-Arachidonoyl Glycerol, 1-Arachidonoyl Glycerol-d5, 2-Arachidonoyl Glycerol, 2-Arachidonoyl Glycerol-d5, 2-Arachidonyl Glycerol ether, 2-Fluoropalmitic Acid, 2-Hydroxymyristic Acid, 2-Linoleoyl Glycerol, 3-Thiatetradecanoic Acid, 4,5-dehydro Docosahexaenoic Acid, 5,6-dehydro Arachidonic Acid, 7,7-dimethyl-5,8-Eicosadienoic Acid, 8,11-Eicosadiynoic Acid, 9,12-Octadecadiynoic Acid, 9-Octadecenamide Adrenic Acid, α-Linoleic Acid, α-Linolenoyl Ethanolamide Arachidonic Acid, Arachidonic Acid-d8, Arachidonic Acid methyl ester Arachidonic Acid (peroxide free), Arachidonic Acid (sodium salt), Arachidonoyl Ethanolamide, Arachidonoyl Ethanolamide-d8, Arachidonoyl Glycine, Arachidonoyl m-Nitroaniline, Arachidonoyl p-Nitroaniline, Arachidonyl Trifluoromethyl Ketone, cis-Parinaric Acid, Conjugated Linoleic Acid (10E,12Z), Conjugated Linoleic Acid (9E,11E)
Conjugated Linoleic Acid (9Z,11E), Decanoyl m-Nitroaniline,
Decanoyl p-Nitroaniline, Dihomo-γ-Linolenic Acid, Dihomo-γ-Linolenic Acid ethyl ester, Dihomo-γ-Linolenic Acid methyl ester, Dihomo-γ-Linolenoyl Ethanolamide, Docosahexaenoic Acid, Docosahexaenoic Acid-d5, Docosapentaenoic Acid, Docosatetraenoyl Ethanolamide, Docosatrienoic Acid, Eicosapentaenoic Acid, Eicosapentaenoic Acid (peroxide free), Eicosatetraynoic Acid, Eicosatrienoic Acid (11Z,14Z,17Z), Eicosatrienoic Acid (5Z,8Z,11Z), Eicosatriynoic Acid, Elaidic Acid, γ-Linolenic Acid
Lauric Acid, Linoelaidic Acid, Linoleic Acid, Linoleic Acid-d4, Linoleic Acid (peroxide free), Linoleoyl Ethanolamide, Mead Acid Ethanolamide, Methyl α-Linolenyl Fluorophosphonate, Methyl Arachidonyl Fluorophosphonate, Methyl γ-Linolenate, Methyl γ-Linolenyl Fluorophosphonate, N-Oleoylglycine, N-Oleoyl Taurine, N-Palmitoyl Taurine, N-Stearoyl Taurine, Oleic Acid, Oleic Acid-2,6-diisopropyl Anilide, Oleoyl Ethanolamide, oleyl Anilide, Oleyl Trifluoromethyl Ketone, ω-3 Arachidonic Acid, ω-3 Arachidonic Acid-d8, Palmitic Acid, Palmitoyl Ethanolamide, Palmityl Trifluoromethyl Ketone, Phytanic Acid, Stearidonic Acid, Stearidonic Acid methyl ester, Stearoyl Ethanolamide, Traumatic Acid, Umbelliferyl Arachidonate, Sodium 1-butanesulfonate, Sodium pentanesulfonate, Sodium 1-heptanesulfonate, sodium octyl sulfate, Sodium decyl sulfate, (Sodium dodecyl sulfate) Lithium dodecyl sulfate, Sodium 1-dodecanesulfonate, Sodium tetradecyl sulfate, Sodium hexadecyl sulfate, Sodium hexanesulfonate, Sodium octadecyl sulfate, sodium lauryl ether sulfate, 2-HYDROXY-3-SULFOPROPYL DODECANOATE, N-lauryl sarcosine dioctyl sulfosuccinate, DOSS, di-2 ethylhexyl sulfosuccinate and sodium salt, f) Isothermal Titration Calorimetry of Globulomers:

FIG. 15 depicts the results from the binding of the monoclonal antibody A to globulomers prepared from recombinant MetA-beta 1-42. The binding was directly measured by isothermal titration calorimetry (ITC). In this example the calorimeter cell contained amyloid beta at a concentration of 86 micromolar (based on a monomer unit). It was titrated with antibody A at 132 micromolar. Both were in a 5 mM sodium phosphate buffer with 35 mM NaCl at pH7.4. The fitted dissociation constant (Kd of binding) was 490 nanomolar (or 0.46 uM), the observed enthalpy of binding was −47.5 kilojoules per mole and the apparent stoichiometry of binding was 6.3 amyloid beta molecules per antibody molecule. Together with the hydrodynamic analyses (FIGS. 13 and 21) this suggests about two antigenic combining sites per globulomeric unit.

g) NMR Features:

Sample Preparation: Isotopes were purchased from Cambridge Isotope Laboratories and Isotec. Minimal Media [Sambrook, et al., Molecular Cloning: A Laboratory Manual, Cold Spring Harbor Laboratory Press, New York, 1989] were used for all the labeled samples prepared for NMR studies. N-Met 1-42 peptide was cloned into pET29a vector and expressed in E. coli strain BL21 (DE3). The cells were grown at 36° C. in shake flasks until OD reached 1.0 and then expressed at 42° C. for 2 hours. Uniformly [$^{15}$N]-labeled samples were grown with 1 g/L $^{15}$NH$_4$Cl and 3 g/L glucose in H$_2$O medium. Uniformly [$^{15}$N,$^{2}$H]-labeled sample was grown with 1 g/L $^{15}$NH$_4$Cl and 3 g/L D-glucose-d$_{12}$ in D$_2$O medium. Uniformly [$^{14}$N,$^{2}$H]-labeled sample was grown with 1 g/L $^{14}$NH$_4$Cl and 3 g/L D-glucose-d$_{12}$ in D$_2$O medium. Uniformly [$^{15}$N,$^{2}$H, $^{13}$C]-labeled sample was grown with 1 g/L $^{14}$NH$_4$CL and 3 g/L [$^{13}$C,$^{2}$H]-glucose-d$_{12}$ in 100% D$_2$O medium. Uniformly [$^{15}$N]-labeled sample with selectively $^{13}$C-labeled protonated methyl groups of Ile, Val, Leu residues in a 2H background was prepared by growing cells in media that contained 100% D$_2$O, D-glucose-d$_{12}$ (3 g/L), and $^{15}$NH$_4$Cl (1 g/L) and by supplementing media with 3-$^{13}$C-α-ketobutyrate (50 mg/L for labeling isoleucine methyl groups) and 3,3-$^{13}$C$_2$-α-ketoisovalerate (100 mg/L, for labeling valine and leucine methyl groups simultaneously). The expressed peptide was purified as described above in Example III. By using the published protocol of Barghorn et al. (J. Neurochem. 2005 95, 834-847), the NMR sample was prepared and concentrated to final concentration of 16 mg/ml in a buffer containing −1.5% SDS-d$_{25}$ and 1× phosphate buffered saline at pH 7.4 (GIBCO). For preparation of mixed samples, the purified peptides with different labeling schemes were mixed at 1:1 ratio before subject onto the protocol for sample preparation.

NMR Spectroscopy: The NMR spectra were collected at 25° C. on a Bruker DRX800 or DRX800 NMR spectrometer. The $^1$H, $^{15}$N, and $^{13}$C resonances of the backbone were assigned using triple resonance experiments (HNCA, HN(CO)CA, HN(CA)CB, HN(COCA)CB) [T. Yamazaki, et al., J. Am. Chem. Soc. 116, 11655-11666, (1994)] using the uniformly [$^{15}$N,$^2$H,$^{13}$C]-labeled sample. $^1$H$_\alpha$ and side chain signal resonances were assigned from is N-edited NOESY spectra [S. W. Fesik, et al., J. Magn. Reson. 78, 588-593, (1988); G. M. Clore, et al., Meths. Enzymol. 239, 349-363, (1994)] using a uniformly $^{15}$N-labeled sample. Backbone amide NH—NH NOEs were assigned from the 3D $^{15}$N-resolved NOESY experiment by using a uniformly [$^{15}$N]-labeled sample with selectively $^{13}$C-labeled protonated methyl groups of Ile, val, Leu residues in a $^2$H background. $^{15}$N-filtered and $^{15}$N-edited 3D NOESY experiment was conducted as previously described [M. Ikura, et al., J. Am. Chem. Soc. 114, 2433-2440, (1992); G. W. Vuister, et al., J. Am. Chem. Soc. 116, 9206-9210, (1994)] by using a mixed sample in which [U-$^{15}$N,$^2$H]-labeled and [U-$^{14}$N,$^2$H]-labeled samples were mixed at 1:1 ratio. A separate mixed sample in which a [U-15N,2H]-labeled peptide was mixed at 1:1 ratio with a [U-14N,2H]-labeled peptide that contains selectively 13C-labeled protonated methyl groups of IVL residues was used in 15N-filtered and 15N-edited 3D NOESY experiments. NOESY mixing times used in these experiments ranged from 80 to 400 msec.

Structure Calculations: Structures of the repeating unit of the s-amyloid peptide N-met 1-42 were calculated using a simulated annealing protocol [M. Nilges, et al., FEBS Lett, 229, 317-324, (1988)] with the program CNX [A. T. Brunger, et al., Acta Crystallogr. D54 (Pt 5), 905-21, (1998)]. A total of 178 distance restraints derived from the analysis of the NMR data were included in the structure calculation. In addition, 44 φ angular restraints in the β-sheet regions were included in the structural calculations based on the analysis of $C_\alpha$ and $C_\beta$ chemical shifts [G. Cornilescu, et al., J. Biomol. NMR 13, 289-302, (1999)].

Figure 16A:
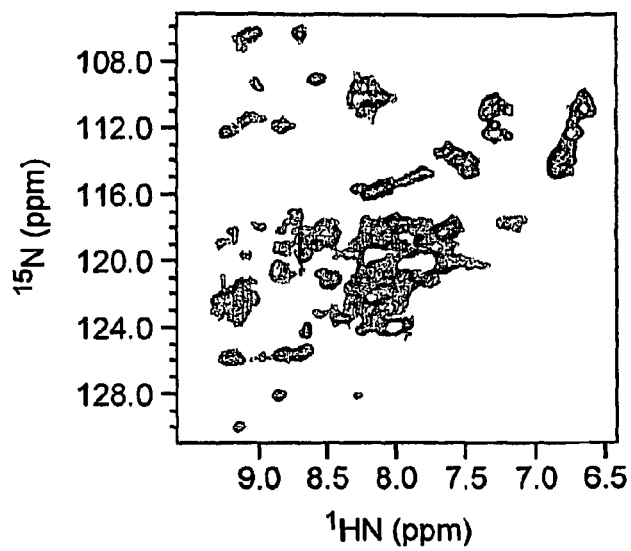
FIG. 16 depicts $^{15}N/^{1}H$ heteronuclear single quantum correlation spectroscopy (HSQC) spectrum of the $^{15}N$-labeled N-Met Aβ1-42 in 90% $H_2O$/10% $D_2O$ solution (panel A) and one day after exchange into 100% $D_2O$ solution (panel B).
Figure 16B:
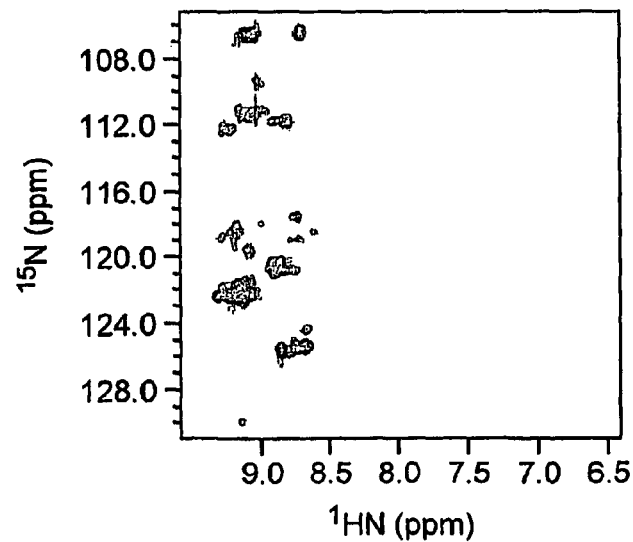

In conclusion, the soluble globulomers of amyloid β peptide N-Met 1-42 (called Aβ1-42) were prepared and studied by NMR. The $^{15}$N/$^1$H heteronuclear single quantum correlation spectroscopy (HSQC) spectrum of the $^{15}$N-labeled Aβ1-42 in 90% $H_2O$/10% $D_2O$ solution (FIG. 23A) clearly shows that the cross peaks in the spectrum are well dispersed and highly shifted downfield relative to the chemical shifts of the unfolded peptide in solution. After exchange into 100% $D_2O$ solution, the downfield shifted amides are still clearly observed after one day in $D_2O$ (FIG. 16B), indicating that these amide protons are shielded from solvent and possibly hydrogen-bonded. These results indicate that the observable form of Aβ1-42 is highly structured in solution.

Figures 17A, 17B:
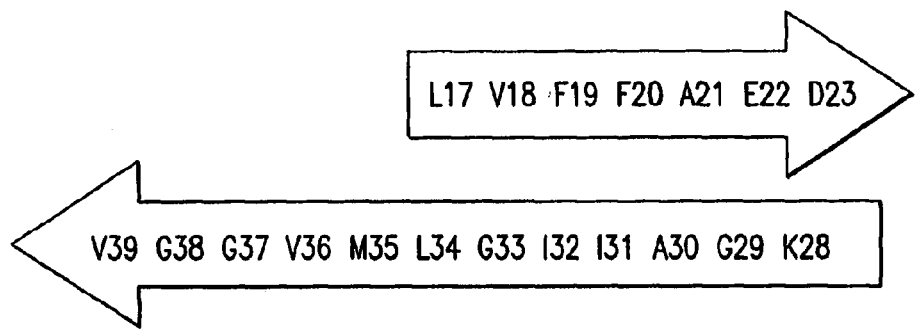
FIG. 17(A) represents the sequence of the N-met amyloid beta peptide 1-42. The two beta-strands identified by NMR are boxed (SEQ ID NO:8).
FIG. 17(B) represents the anti-parallel beta-sheet of Abeta1-42 identified from the analysis of the inter-stand NOEs of the NMR data ((SEQ ID NO:9) (aas 28-39); SEQ ID NO:10 (aas 17-23)).

Further, a suite of NMR triple resonance backbone experiments were collected for the uniformly $^2$H, $^{15}$N, and $^{13}$C-labeled forms of Aβ1-42. Most of the shifted cross peaks in the $^{15}$N/$^1$H HSQC spectrum have been assigned to the individual backbone amides. Based on the assigned chemical shifts of Cα and Cβ resonances, two β-strands were found to be present for the residues 17-23 and 28-39 of N-Met Aβ1-42 (FIGS. 17 and 20). By using different isotope-labeled samples, the observed intra- vs. inter-molecular NOEs were differentiated in $^{15}$N-filtered and $^{15}$N-edited 3D NOESY experiments. Data analyses and structure calculations indicate that the structure of the observable N-Met Aβ1-42 contains mixed parallel/antiparallel beta-sheets (FIGS. 20, 21 and 24). These solution NMR studies on N-Met Aβ1-42 suggest that the peptide folding in the globulomer pathway exhibits a structure that is distinct from the fibrilomer structure of the fibril pathway, as described by Sciarretta et al. (*Biochemistry* 2005, 44, 6003-6014). The minimum repeating intra and interchain interactions are those observed and described herein.

EXAMPLE VI

Example of Development of a Hybridoma Cell Line

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The particular protocol used to produce one monoclonal antibody described herein (e.g., monoclonal antibody A) is as follows:

Immunization of mice: Balb/c and A/J mice (6-8 week old) were immunized subcutaneously with 50 ug of antigen in CFA. Animals were boosted every three weeks with 50 ug of antigen in Immuneasy™ (Qiagen) for a total of three boosts, Four days prior to fusion, mice were boosted with 10 ug of antigen intravenously.

Cell fusion and hybridoma screening: Spleen cells from immunized animals were fused with SP2/0-Ag14 myeloma cells at a ratio of 5:1 using standard techniques. Seven to ten days post fusion, when macroscopic colonies were observed, SN were tested by ELISA for antibody to Abeta 20-42. Cells from ELISA positive wells were scaled up and cloned by limiting dilution.

Antibody isotype determination: The isotype of the anti-Abeta 20-42 Mabs was determined using the Zymed EIA isotyping kit.

Scale up and purification of monoclonal antibodies: Hybridomas were expanded into media containing 5% Low IgG. Fetal bovine serum (Hyclone). Supernatant was harvested and concentrated. Mab was purified using Protein A chromatography and dialyzed into PBS.

Serum titers. Ten mice were immunized with the Abeta 20-42. All mice seroconverted with ELISA titers (½ Max OD 450 nm) of 1:5000-10,000.

Monoclonal antibody A, B and D described herein were producing using the non-Met form of amyloid beta protein. Monoclonal antibody C described herein was produced using the non-Met 1-42 form of amyloid beta protein.

EXAMPLE VII

Figure 26:
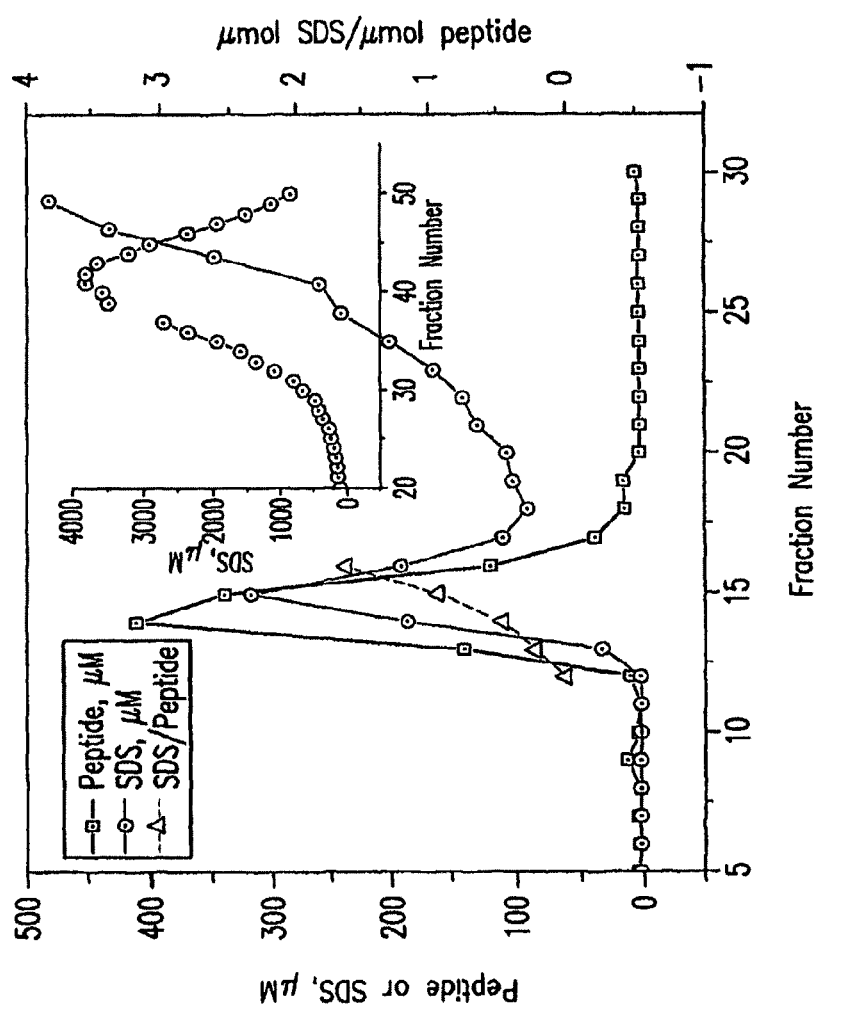
FIG. 26 illustrates the binding of SDS to Abeta globulomers using $C^{14}$-SDS.

Binding of SDS to Abeta Globulomers Using $C^{14}$-SDS 13.5 mL of the Abeta globulomers at the 0.05% SDS stage were concentrated to 0.62 mL. 0.3 mL of this concentrated material was applied to the 10 mL EconoPac DG10 column. 0.25 mL fractions were collected by hand. The inset of Figure X shows the region where free, monomer, SDS elutes, with expanded γ-axis. The concentration of peptide (solid squares) and SDS (solid circles), as well as the ratio of SDS to peptide (open triangles) is presented. The ratio of SDS to peptide across the globulomer peak (fractions 14 and 15) is between about 0.5 to about 1.5 molecules of SDS per molecule of peptide. The chromatographic separation indicates the SDS is separating with the Abeta peptide upon being subjected to size-exclusion chromatography. The results are shown in FIG. 26.

The measurement of the amount of detergent bound in a protein-detergent aggregate using radio-labeled detergent and size exclusion chromatography is well established in the literature Tanford and co-workers have made use of this in the study of a variety of proteins, including bovine serum albumin (Makino et al., (1973), *J. Biol. Chem.*, 248:4926-4932), several proteins in SDS (Tanford et al., (1974), *Biochemistry*, 13:2369-2376); and is cited as a general method for the characterization of membrane proteins in detergent solution (Tanford and Reynolds, (1976), *BBA*, 457: 133-170). Moller and colleagues have also made a survey of detergent binding to membrane proteins using this method (Moller and leMaire, (1993), J. Biol. Chem. 2658: 18659-18672). LeMaire and colleagues have also made extensive use of this methodology, especially with $Ca^{2+}$-dependent ATPase (Rivas et al., (1982), *Anal. Biochem.*, 123:194-200). Based primarily on early work on the study of protein-ligand interactions first described by Hummel and Dryer ((1962), *BBA*, 63: 530-532), Helenius and Simmons modified the method specifically to examine protein detergent interactions ((1972), *J. Biol. Chem.*, 247: 3656-3661)). The co-migration of a detergent with a protein on size exclusion chromatography column is a proof of physical interaction between the protein and the detergent. According to Helenius and Simmons (ibid), "The amount of detergents bound to the proteins could be measured from the amount of radioactive detergent that co-eluted with the protein."

This technique is based, in part, on the requirement that the chromatographic gel efficiently excludes the protein while including the ligand (SDS in this case of globulomers) (Andreu, (1985), *Methods in Enzymology*, 117: 346-354). In these experiments we are working below the CMC (critical micelle concentration) of the SDS, so the detergent molecules behave in solution as monomers. As monomers they will partition into the pores of a desalting resin such as the DG10 employed, while the Abeta globulomers will be excluded. Thus the resin can efficiently separate free SDS from Abeta globulomers and any SDS bound to them. SDS found to co-migrate with the Abeta globulomers can be described as bound. In the classic utilization of this method, the size exclusion columns are equilibrated in a background level of SDS. Binding of SDS to a protein is then observed as a rise in detergent levels above this background level if concomitant with protein elution.

Herein, an examination was made of SDS binding in the absence of any competing detergent in the buffer. This method affords a more stringent probe of bound SDS, as there is no ready supply of free SDS to replace any that may partition away from the Abeta globulomers during the chromatography. However, it does lead to the change in apparent stoichiometric ratio of peptide to SDS across the eluting globulomer peak because SDS that partitions (into the gel chromatography matrix) during the chromatography was not completely separated from the eluting Abeta globulomers (because it bound to the globulomers).

EXAMPLE VIII

Comparison of Backbone Amide Protection of the Globulomer and Fibril Forms of the Amyloid Beta Peptide Globulomer Backbone Amide Exchange Experiments:

Globulomer samples in aqueous buffer were flash-frozen in liquid nitrogen and lyophilized overnight. Some of these lyophilized samples are stored at −70° C. and serve as the reference samples (never in $D_2O$). The rest of lyophilized samples were then dissolved in $D_2O$. After various periods of time at 4° C. during which exchangeable H/D exchanges occur, these samples are flash-frozen in liquid nitrogen to quench the H/D exchanges and lyophilized. One-dimensional and two-dimensional $^{15}N/^1H$ HSQC spectra were then collected within 3 minutes after dissolving these exchanged samples as well as the unexchanged (reference) samples in 480 ul DMSO-$d_6$ (Cambridge Isotope Laboratories Inc., Andover, Mass.) that contains 0.07% deteurated dichloroacetic acid (Cambridge Isotope Laboratories Inc., Andover, Mass.). Upon dissolving the globulomer in the acidified DMSO-$d_6$, the multimeric globulomer is converted into monomer. The $^{15}N/^1H$ HSQC spectrum of this monomeric form of the amyloid β peptide in this acidified DMSO-$d_6$ solvent is assigned by collecting a suite of backbone experiments (T. Yamazaki et al., (1994) *J. Am. Chem. Soc.* 116, 11655-11666) with a [U-$^{15}N$,$^{13}C$]-labeled sample. With these assignments, the peak intensities of the individual residues of the amyloid β peptide are analyzed and their backbone amide protection factors are obtained. The protection factor is defined as the ratio of the observed cross peak intensity of the sample after exchange in $D_2O$ over the intensity of the sample that has not subjected to $D_2O$ exchange. A monomeric concentration of 0.5 mM was used in these exchange experiments. The peak intensity used in the protection factor calculation was calibrated based upon the aliphatic $CH_3$ region intensity of the 1D NMR spectra.

Preglobulomer (Early Preparation Step Peptide) Backbone Amide Exchange Experiments: After lyophilizing a $^{15}N$-labeled sample in a buffer containing ~1.5% SDS-$d_{25}$ and 1× phosphate buffered saline at pH 7.4 (GIBCO/Invitrogen, Carlsbad, Calif.), the dried sample was then dissolved in $D_2O$ and a series of $^{15}N/^1H$ HSQC spectra were collected. Slowly exchange amides were detected in these experiments.

The experiments were performed with the Met-amyloid beta but for ease of graphical comparison with literature data (see below) the N-terminal Met residue is left out of the figure panels (see FIG. 26). The protection factor is defined as the ratio of the observed cross peak intensity in the $^{15}N/^1H$ HSQC spectra for the sample after exchange in $D_2O$ over the intensity of the sample that has not subjected to $D_2O$ exchange. For the globulomer, duplicate data sets for the backbone amide protection experiments were collected and used to report their average and standard deviations Residues D1, D7, S8, and H14 in the globulomer were excluded since they exhibited intrinsically fast back exchange rates in the DMSO/acid solvent used in the current experiments. Due to spectral overlap for the residue pairs (E11 and D23), (V1 and V36), and (I32 and I41) (as indicated by stars in the panel B), only average protection factors for these pairs of backbone amides can be reported. As a result, the uncertainties shown for these overlapped residues were derived by estimating the highest and lowest protection factors that the individual residue could exhibit (assuming a maximum protection factor of 80%) and by using the standard deviation of these limits. The amide protection of the globulomer shown in panel B is for the sample that has been subjected to exchange for 5 days in $D_2O$. The fibril backbone amide protection in panel C was taken from Olofsson et al. ((2006), *JBC* 281, 477-483) after 20 min (dark bars) and 120 min (light gray bars) of incubation in $D_2O$. In addition, panel A shows the backbone assignment and amide exchange data for the preglobulomer. The assigned and non-assigned residues are indicated by + and − signs, respectively. The backbone amides of the peptide characteristic of the early preparation step (preglobulomer) that exhibited slow, moderate, and fast exchange rates are indicated by filled, semi-filled, and open circles, respectively, below the sequence. In contrast to the fibrillar form, in which slow amide exchange rates were observed for both the central and C-terminal residues (panel C of FIG. 25), slow exchange rates are mainly observed for the C-terminal 12 residues in the preglobulomer (panel A of FIG. 25) and globulomer (panel B of FIG. 25). Thus, this comparison demonstrates that the preglobulomer (panel A of FIG. 25) and globulomer (panel B of FIG. 25) forms of the amyloid β peptide exhibit very similar amide exchange rates, consistent with both forms adopting a similar core structure. In contrast, both the preglobulomer and globulomer forms exhibit distinctly different NH/ND exchange rates from the central region of the peptide of the fibrilliar form, suggesting that they have a different structural core than that of the fibrillar form.

Designations of Deposited Antigens

Deposited A-Beta Clones:

| Protein Form | D# | ATCC Deposit Designations |
|---|---|---|
| M-[A-beta (1-39)] | 880 | PTA-7245 |
| M-[A-beta (1-40)] | 879 | PTA-7246 |
| M-[A-beta (1-41)] | 878 | PTA-7243 |
| M-[A-beta (1-42)] | 718 | PTA-7244 |
| M-[A-beta (1-43)] | 881 | PTA-7248 |
| M-[A-beta (12-42)] | 1065 | PTA-7250 |
| M-[A-beta (1-42), N27A] | 1084 | PTA-7247 |
| M-[A-beta (1-42), A21G] | 1088 | PTA-7249 |
| M-[A-beta (1-42), E22G] | 1089 | PTA-7251 |

The "D" numbers represent internal designations of Abbott Laboratories.

The above-deposits were made under the terms of the Budapest Treaty and were received by the American Type Culture Collection, 10801 University Boulevard, Manassas Va. 20110-2209 on Dec. 1, 2005

What is claimed is:

1. A purified beta-amyloid protein consisting of an amino acid sequence at least 70% identical to the amino acid sequence of native beta-amyloid protein, and consists of a sequence represented by the formula [X+Y], wherein
    "X" consists of one or more amino acids located at the amino terminus of the purified protein selected from the group consisting of methionine, valine, and leucine, and
    "Y" comprises all or a portion of the amino acid sequence of beta amyloid protein, and contains a mutation selected from the group consisting of A2T, H6R, D7N, A21G, E22G, E22Q, E22K, D23N, A42T, and A42V, the numbers being relative to the N-terminus of the native beta-amyloid protein.

2. The purified beta-amyloid protein of claim 1, wherein "X" is methionine.

3. A purified globulomer comprising at least two of the purified beta-amyloid proteins of claim 1.

4. A vaccine comprising the purified beta-amyloid protein of claim 1 or the globulomer of claim 3, and further comprising a pharmaceutically acceptable adjuvant.

5. A method of treating Alzheimer's Disease in a patient in need of treatment comprising the step of administering said vaccine of claim 4 to said patient in an amount sufficient to effect said treatment.

6. An isolated nucleic acid encoding the purified beta-amyloid protein of claim 1.

7. A vector comprising said isolated nucleic acid molecule of claim 6.

8. A host cell comprising said vector of claim 7.

9. A method of producing the purified beta-amyloid protein of claim 1, comprising the steps of:
    (a) inserting a nucleic acid molecule encoding the purified beta-amyloid protein of claim 1 into a vector; and
    (b) transforming the vector containing the nucleic acid molecule encoding the purified beta-amyloid protein of claim 1 into a host cell for a time and under conditions sufficient for expression of the beta-amyloid protein by the host cell.

10. The method of claim 9 wherein said host cell is prokaryotic or eukaryotic.

11. The method of claim 10 wherein said prokaryotic host cell is selected from the group consisting of *Escherichia coli, Bacillus* sp., *Streptococcus* sp, and *Lactobacillus* sp.

12. The method of claim 10 wherein said eukaryotic cell is selected from the group consisting of an insect cell, a yeast cell and a mammalian cell.

13. A method of diagnosing Alzheimer's Disease in a patient suspected of having this disease comprising the steps of:
    (a) isolating a biological sample from said patient;
    (b) contacting said biological sample with the globulomer of claim 3 for a time and under conditions sufficient for the formation of complexes comprising the globulomer and antibodies against the globulomer which may be present in the sample;

(c) adding a conjugate to the resulting antibody/globulomer complexes for a time and under conditions sufficient to allow said conjugate to bind to the complexes, wherein said conjugate comprises antibodies that bind to the anti-globulomer antibodies and comprises a compound capable of generating a detectable signal; and (d) detecting the presence of antibodies that bind to the globulomers which may be present in the biological sample by detecting a signal generated by the compound, said signal indicating a diagnosis of Alzheimer's disease in said patient.

14. A method of diagnosing Alzheimer's Disease in a patient suspected of having Alzheimer's Disease comprising the steps of:

(a) isolating a biological sample from said patient;

(b) contacting said biological sample with the globulomer of claim 3 for a time and under conditions sufficient for the formation of complexes comprising the globulomer and antibodies against the globulomer which may be present in the sample;

(c) detecting the presence of said complexes in the sample, the presence of said complexes indicating a diagnosis of Alzheimer's Disease in said patient.

\* \* \* \* \*